US006252047B1

(12) United States Patent
Billing-Medel et al.

(10) Patent No.: US 6,252,047 B1
(45) Date of Patent: Jun. 26, 2001

(54) REAGENTS AND METHODS USEFUL FOR DETECTING DISEASES OF THE PROSTATE

(75) Inventors: Patricia A. Billing-Medel, Gurnee; Maurice Cohen, Highland Park; Tracey L. Colpitts, Round Lake; Paula N. Friedman, Deerfield; Julian Gordon, Lake Bluff; Edward N. Granados, Vernon Hills; Steven C. Hodges, Buffalo Grove; Michael R. Klass, Libertyville, all of IL (US); Jon D. Kratochvil, Kenosha, WI (US); Lisa Roberts-Rapp, Gurnee, IL (US); John C. Russell, Pleasant Prairie, WI (US); Stephen D. Stroupe, Libertyville; Hong Yu, Buffalo Grove, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/525,397

(22) Filed: Mar. 15, 2000

Related U.S. Application Data

(60) Division of application No. 09/071,710, filed on May 1, 1998, now Pat. No. 6,130,043, which is a continuation-in-part of application No. 08/850,713, filed on May 2, 1997, now abandoned.

(51) Int. Cl.[7] .............................. C07K 13/00; C07K 15/28
(52) U.S. Cl. .................... 530/350; 530/387.1; 530/388.1
(58) Field of Search ................................ 530/350, 387.1, 530/388.1

(56) References Cited

U.S. PATENT DOCUMENTS 6,027,945 * 2/2000 Smith et al. ........................ 436/526

FOREIGN PATENT DOCUMENTS 9520681   8/1995   (WO).
9736535   10/1997  (WO).

OTHER PUBLICATIONS

Lee et al, Gov. Rep. Announce. Index (U.S.) 89(14) Abstr. No. 939,035, Abstract Only, 1989.*

Gingrich et al, "Identification, characterization and molecular cloning of a novel transporter like protein localized to the central nervous system", Febs Lett 312(2–3):115–122, Nov. 1992.*

Abstract XP 00611577–Blok, et al., "Isolation cDNAs That Are Differentially Expressed Between Androgen–Dependent and Androgen–Indepedent Prostate Carcinoma Cells Using Differential Display PCR", *The Prostate*, 26(4):213–224 (1995).

Abstract XP 002019344–Robson, et al., "Identification of Prostatic Androgen Regulated Genes Using the Differential Display Technique", *Proc. Of the American Assoc. For Cancer Research*, 36:266 (1995).

Abstract XP 002075062–Williamson, et al., "WashU–Merck EST PROJECT", (1996).

Abstract XP 002075063–Hillier, et al., "WashU–Merck EST PROJECT, " (1996).

Abstract XP 002075064–Emmert–Buck, "National Cancer Institute, Cancer Genome Anatomy Project," (1997).

Hanks, et al., "Cancer of the Prostate", *Cancer Principles & Practice of Oncology*, 1:4th Ed., 1073–1113 (1993).

Jacobs, et al., "Clinical Use of Tumor Markers in Oncology", *Curr. Prob. Cancer*, 299–350 (1991).

Pantel, et al., "Methods for Detection of Micrometastatic Carcinoma Cells in Bone Marrow, Blood and Lymph Nodes", *Onkologie*, 18:394–401 (1995).

Schwartz, M.K., "Cancer Markers", *Principles & Practice Oncology*, 1(4th Ed.):531–542 (1993).

Karet, et al., "Quantification of mRNA in human tissue using fluorescent nested reverse–transcriptase polymerase chain reaction", *Anal. Biochem.*, 220:384–390 (1994).

Hillier, et al., Genbank Locus N95796, Aug. 20, 1996.

Hillier, et al., Genbank Locus AA112573, Nov. 8, 1996.

Dynal Technical Handbook, Biomagnetic techniques in molecular biology, 120–127, 139, 153–155 (1995).

* cited by examiner

*Primary Examiner*—Jeffrey Fredman
(74) *Attorney, Agent, or Firm*—Mimi C. Goller

(57) ABSTRACT

A set of contiguous and partially overlapping cDNA sequences and polypeptides encoded thereby, designated as PS108 and transcribed from prostate tissue, is described. These sequences are useful for the detecting, diagnosing, staging, monitoring, prognosticating, in vivo imaging, preventing or treating, or determining the predisposition of an individual to diseases and conditions of the prostate, such as prostate cancer. Also provided are antibodies which specifically bind to PS108-encoded polypeptide or protein, and agonists or inhibitors which prevent action of the tissue-specific PS108 polypeptide, which molecules are useful for the therapeutic treatment of prostate diseases, tumors or metastases.

8 Claims, 9 Drawing Sheets

```
>1864683    GGGGCTGTAC CAGGGCGTGC CCAGAGCTGA GCCGGGCACC GAGGCCCGGA
>1711346          AC CAGGGCGTGC CCAGAGCTGA GCCGGGCACC GAGGCCCGGA
>1711346IH        AC CAGGGCGTGC CCAGAGCTGA GCCGGGCACC GAGGCCCGGA
Consensus   GGGGCTGTAC CAGGGCGTGC CCAGAGCTGA GCCGGGCACC GAGGCCCGGA >1864683    GACACTATGA TGAAGGCGTT CGGATGGGCA GCCTGGGGCT GTTCCTGCAG
>1711346    GACACTATGA TGAAGGCGTT CGGATGGGCA GCCTGGGGCT GTTCCTGCAG
>1711346IH  GACACTATGA TGAAGGCGTT CGGATGGGCA GCCTGGGGCT GTTCCTGCAG
Consensus   GACACTATGA TGAAGGCGTT CGGATGGGCA GCCTGGGGCT GTTCCTGCAG >1864683    TGCGCCATCT CCCTGGTCTT CTCTCTGGTC ATGGACCGGC TGGTGCAGCG
>1711346    TGCGCCATCT CCCTGGTCTT CTCTCTGGTC ATGGACCGGC TGGTGCAGCG
>1711346IH  TGCGCCATCT CCCTGGTCTT CTCTCTGGTC ATGGACCGGC TGGTGCAGCG
Consensus   TGCGCCATCT CCCTGGTCTT CTCTCTGGTC ATGGACCGGC TGGTGCAGCG >1864683    ATTCGGCACT CGAGCAGTCT ATTTGGCCAG TGTGGCAGCT TTCCCTGTGG
>1711346    ATTCGGCACT CGAGCAGTCT ATTTGGCCAG TGTGGCAGCT TTCCCTGTGG
>1711346IH  ATTCGGCACT CGAGCAGTCT ATTTGGCCAG TGTGGCAGCT TTCCCTGTGG
Consensus   ATTCGGCACT CGAGCAGTCT ATTTGGCCAG TGTGGCAGCT TTCCCTGTGG >1864683    CTGCCGGTGC CACATGCCTG TCCCACAGTG TGGCCGTGGT GACAGCTTCA
>1711346    CTGCCGGTGC CACATGCCTG TCCCA
>1711346IH  CTGCCGGTGC CACATGCCTG TCCCACAGTG TGGCCGTGGT GACAGCTTCA
>1913982                                                GACAGCTTCA
Consensus   CTGCCGGTGC CACATGCCTG TCCCACAGTG TGGCCGTGGT GACAGCTTCA >1864683    GCCGCCTT
>1711346IH  GCCGCCCTCA CCGGGTTCAC CTTCTCAGCC CTGCAGATCC TGCCCTACAC
>1913982    GCCGCCCTCA CCGGGTTCAC CTTCTCAGCC CTGCAGATCC TGCCCTACAC
Consensus   GCCGCCCTCA CCGGGTTCAC CTTCTCAGCC CTGCAGATCC TGCCCTACAC >1711346IH  ACTGGCCTCC CTCTACCACC GGGAGAAGCA GGTGTTCCTG CCCAAATACC
>1913982    ACTGGCCTCC CTCTACCACC GGGAGAAGCA GGTGTTCCTG CCCAAATACC
Consensus   ACTGGCCTCC CTCTACCACC GGGAGAAGCA GGTGTTCCTG CCCAAATACC >1711346IH  GAGGGGACAC TGGAGGTGCT AGCAGTGAGG ACAGCCTGAT GACCAGCTTC
>1913982    GAGGGGACAC TGGAGGTGCT AGCAGTGAGG ACAGCCTGAT GACCAGCTTC
Consensus   GAGGGGACAC TGGAGGTGCT AGCAGTGAGG ACAGCCTGAT GACCAGCTTC >1711346IH  CTGCCAGGCC CTAAGCCTGG AGCTCCCTTC CCTAATGGAC ACGTGGGTGC
>1913982    CTGCCAGGCC CTAAGCCTGG AGCTCCCTTC CCTAATGGAC ACGTGGGTGC
>825779                                 GCTCCCTTC CCTAATGGAC ACGTGGGTGC
Consensus   CTGCCAGGCC CTAAGCCTGG AGCTCCCTTC CCTAATGGAC ACGTGGGTGC >1711346IH  TGGAGGCAGT GGCCTGCTCC CACCTCCACC CGCGCTCTGC GGGGCCTCTG
>1913982    TGGANGCAGT GGCCTGCTCC CACCTCCACC CGCGCTCTGC GGGGC
>825779     TGGAGGCAGT GGCCTGCTCC CACCTCCACC CGCGCTCTGC GGGGCCTCTG
Consensus   TGGAGGCAGT GGCCTGCTCC CACCTCCACC CGCGCTCTGC GGGGCCTCTG
```

FIG. 1A

```
>1711346IH  CCTGTGATGT CTCCGTACGT GTGGTGGTGG GTGAGCCCAC CGAGGCCAGG
>825779     CCTGTGATGT CTCCGTACGT GTGGTGGTGG GTGAGCCCAC CGAGGCCAGG
Consensus   CCTGTGATGT CTCCGTACGT GTGGTGGTGG GTGAGCCCAC CGAGGCCAGG >1711346IH  GTGGTTCCGG GCCGGGGCAT CTGCCTGGAC CTCGCCATCC TGGATAGTGC
>825779     GTGGTTCCGG GCCGGGGCAT CTGCCTGGAC CTCGCCATCC TGGATAGTGC
>2626650                                                TGGATAGTGC
Consensus   GTGGTTCCGG GCCGGGGCAT CTGCCTGGAC CTCGCCATCC TGGATAGTGC >1711346IH  CTTCCTGCTG TCCCAGGTGG CCCCATCCCT GTTTATGGGC TCCATTGTCC
>825779     CTTCCTGCTG TCCCAGGTGG CCCCATCCCT GTTTATGGGC TCCATTGTCC
>2626650    CTTCCTGCTG TCCCAGGTGG CCCCATCCCT GTTTATGGGC TCCATTGTCC
Consensus   CTTCCTGCTG TCCCAGGTGG CCCCATCCCT GTTTATGGGC TCCATTGTCC >1711346IH  AGCTCAGCCA GTCTGTCACT GCCTATATGG TGTCTGCCGC AGGCCTGGGT
>825779     AGCTCAGCCA GTCTGTCA
>2626650    AGCTCAGCCA GTCTGTCACT GCCTATATGG TGTCTGCCGC AGGC:TGGGT
Consensus   AGCTCAGCCA GTCTGTCACT GCCTATATGG TGTCTGCCGC AGGCCTGGGT >1711346IH  CTGGTCGCCA TTTACTTTGC TACACAGGTA GTATTTGACA AGAGCGACTT
>2626650    CTGGTCGCCA TTTACTTTGC TACACAGGTA GTATTTGACA AGAGCGACTT
>1808389                                                       CTT
Consensus   CTGGTCGCCA TTTACTTTGC TACACAGGTA GTATTTGACA AGAGCGACTT >1711346IH  GGCCAAATAC TCAGCGTAGA AAACTTCCAG CACATTGGGG TGGAGGGCCT
>2626650    GGCCAAATAC TCAGCGTAGA AAACTTCCAG CACATTGGGG TGGAGGGCCT
>1808389    GGCCAAATAC TCAGCGTAGA AAACTTCCAG CACATTGGGG TGGAGGGCCT
Consensus   GGCCAAATAC TCAGCGTAGA AAACTTCCAG CACATTGGGG TGGAGGGCCT >1711346IH  GCCTCACTGG GTCCCAGCTC CCCGCTCCTG TTAGCCCCAT GGGGCTGCCG
>2626650    GCCTCACTGG GTCCCAGCTC CC
>1808389    GCCTCACTGG GTCCCAGCTC CCCGCTCCTG TTAGCCCCAT GGGGCTGCCG
Consensus   GCCTCACTGG GTCCCAGCTC CCCGCTCCTG TTAGCCCCAT GGGGCTGCCG >1711346IH  GGCTGGCCGC CAGTTTCTGT TGCTGCCAAA GTAATGTGGC TCTCTGCTGC
>1808389    GGCTGGCCGC CAGTTTCTGT TGCTGCCAAA GTAATGTGGC TCTCTGCTGC
>1651121            GC CAGTTTCTGT TGCTGCCAAA GTAATGTGGC TCTCTGCTGC
Consensus   GGCTGGCCGC CAGTTTCTGT TGCTGCCAAA GTAATGTGGC TCTCTGCTGC >1711346IH  CACCCTGTGC TGCTGAGGTG CGTAGCTGCA CAGCTGGGGG CTGGGGCGTC
>1808389    CACCCTGTGC TGCTGAGGTG CGTAN:TGCA CAGCTGGGGG CTG
>1651121    CACCCTGTGC TGCTGAGGTG CGTAN:TGCA CAGCTGGGGG CTGGGGCGTC
Consensus   CACCCTGTGC TGCTGAGGTG CGTAG:TGCA CAGCTGGGGG CTGGGGCGTC >1711346IH  CCTCTCCTCT CTCCCCAGTC TCTAGGGCTG CCTGACTGGA GGCCTTCCAA
>1651121    CCTCTCCTCT CTCCCCAGTC TCTAGGGCTG CCTGACTGGA GGCCTTCCAA
Consensus   CCTCTCCTCT CTCCCCAGTC TCTAGGGCTG CCTGACTGGA GGCCTTCCAA
```

FIG.1B

```
>1711346IH  GGGGGTTTCA GTCTGGACTT ATACAGGGAG GCCAGAAGGG CTCCATGCAC
>1651121    GGGGGTTTCA GTCTGGACTT ATACAGGGAG GCCAGAAGGG CTCCATGCAC
>3520833                                     GCCAGAAGGG CTCCATGCAC
Consensus   GGGGGTTTCA GTCTGGACTT ATACAGGGAG GCCAGAAGGG CTCCATGCAC >1711346IH  TGGAATGCGG GGACTCTGCA GGTGGATTAC CCAGGCTCAG GGTTAACAGC
>1651121    TGGAATGCGG GGACTCTGCA GGTGGATTAC NC
>3520833    TGGAATGCGG GGACTCTGCA GGTGGATTAC CCAGGCTCAG GGTTAACAGC
Consensus   TGGAATGCGG GGACTCTGCA GGTGGATTAC CCAGGCTCAG GGTTAACAGC >1711346IH  TAGCCTCCTA GTTGAGACAC ACCTAGAGAA GGGTTTTTGG GAGCTGAATA
>3520833    TAGCCTCCTA GTTGAGACAC ACCTAGAGAA GGGTTTTTGG GAGCTGAATA
Consensus   TAGCCTCCTA GTTGAGACAC ACCTAGAGAA GGGTTTTTGG GAGCTGAATA >1711346IH  AACTCAGTCA CCTGGTTTCC CATCTCTAAG CCCCTTAACC TGCAGCTTCG
>3520833    AACTCAGTCA CCTGGTTTCC CATCTCTAAG CCCCTTAACC TGCAGCTTCG
Consensus   AACTCAGTCA CCTGGTTTCC CATCTCTAAG CCCCTTAACC TGCAGCTTCG >1711346IH  TTTAATGTAG CTCTTGCATG GGAGTTTCTA GGATGAAACA CTCCTCCATG
>3520833    TTTAATGTAG CTCTTGCATG GGAGTTTCTA GGATGAAACA CTCCTCCATG
Consensus   TTTAATGTAG CTCTTGCATG GGAGTTTCTA GGATGAAACA CTCCTCCATG >1711346IH  GGATTTGAAC ATATGAAAGT TATTTGTAGG GGAAGAGTCC TGAGGGGCAA
>3520833    GGATTTGAAC ATATGAAAGT TATTTGTAGG GGAAGAGTCC TGAGGGGCAA
>2188949                                 GG GGAAGAGTCC TGAGGGGCAA
Consensus   GGATTTGAAC ATATGAAAGT TATTTGTAGG GGAAGAGTCC TGAGGGGCAA >1711346IH  CACACAAGAA CCAGGTCCCC TCAGCCCACA GCACTGTCTT TTTGCTGATC
>3520833    CACACAAGAA CCAGGTCCCC TCAGCCCACA GCACTGTCTT TTTGCTGATC
>2188949    CACACAAGAA CCAGGTCCCC TCAGCCCACA GCACTGTCTT TTTGCTGATC
Consensus   CACACAAGAA CCAGGTCCCC TCAGCCCACA GCACTGTCTT TTTGCTGATC >1711346IH  CACCCCCCTC TTACCTTTTA TCAGGATGTG GCCTGTTGGT CCTTCTGTTG
>3520833    CANCCCCCTC TTAC:TTTTA TCA
>2188949    CACCCCCCTC TTACCTTTTA TCAGGATGTG GCCTGTTGGT CCTTCTGTTG
>3497504           CTC TTACCTTTTA TCAGGATGTG GCCTGTTGGT CCTTCTGTTG
Consensus   CACCCCCCTC TTACCTTTTA TCAGGATGTG GCCTGTTGGT CCTTCTGTTG >1711346IH  CCATCACAGA GACACAGGCA TTTAAATATT TAACTTATTT ATTTAACAAA
>2188949    CCATCACAGA GACACAGGCA TTTAAATATT TAACTTATTT ATTTAACAAA
>3497504    CCATCACAGA GACACAGGCA TTTAAATATT TAACTTATTT ATTTAACAAA
Consensus   CCATCACAGA GACACAGGCA TTTAAATATT TAACTTATTT ATTTAACAAA >1711346IH  GTAGAAGGGA ATCCATTGCT AGCTTTTCTG TGTTGGTGTC TAATATTTGG
>2188949    GTAGAAGGGA ATCCATTGCT AGCTTTTCTG TGTTGGTGTC TAATATTTGG
>3497504    GTAGAAGGGA ATCCATTGCT AGCTTTTCTG TGTTGGTGTC TAATATTTGG
Consensus   GTAGAAGGGA ATCCATTGCT AGCTTTTCTG TGTTGGTGTC TAATATTTGG
```

FIG. 1C

```
>1711346IH  GTAGGGTGGG GGATCCCCAA CAATCAGGTC CCCTGAGATA GCTGGTCATT
>2188949    GTAGGGTGGG GGATCCCCAA CAATCAGGTC CCCTGAGATA GCT
>3497504    GTANGGTGGG GGATCCCCAA CAATCAGGTC CCCTGAGATA GCTGGTCATT
Consensus   GTAGGGTGGG GGATCCCCAA CAATCAGGTC CCCTGAGATA GCTGGTCATT >1711346IH  GGGCTGATCA TTGCCAGAAT CTTCTTCTCC TGGGGTCTGG CCCCCCAAAA
>3497504    GGGCTGATCA TTGCCAGAAT CTTCTTCTCC TGGGGTCTGG CCCCCCAAAA
Consensus   GGGCTGATCA TTGCCAGAAT CTTCTTCTCC TGGGGTCTGG CCCCCCAAAA >1711346IH  TGCCTAACCC AGGACCTTGG AAATTCTACT CATCCCAAAT GATAATTCCA
>3497504    TGCCTAACCC AGGACCTTGG AAATTCTACT CATCCCAAAT GATAA
>3964174                          AAATTCTACT CATCCCAAAT GATAATTCCA
Consensus   TGCCTAACCC AGGACCTTGG AAATTCTACT CATCCCAAAT GATAATTCCA >1711346IH  AATGCTGTTA CCCAAGGTTA GGGTGTTGAA GGAAGGTAGA GGGTGGGGCT
>3964174    AATGCTGTTA CCCAAGGTTA GGGTGTTGAA GGAAGGTAGA GGGTGGGGCT
Consensus   AATGCTGTTA CCCAAGGTTA GGGTGTTGAA GGAAGGTAGA GGGTGGGGCT >1711346IH  TCAGGTCTCA ACGGCTTCCC TAACCACCCC TCTTCTCTTG GCCCAGCCTG
>3964174    TCAGGTCTCA ACGGCTTCCC TAACCACCCC TCTTCTCTTG GCCCAGCCTG
Consensus   TCAGGTCTCA ACGGCTTCCC TAACCACCCC TCTTCTCTTG GCCCAGCCTG >1711346IH  GTTCCCCCCA CTTCCACTCC CCTCTACTCT CTCTAGGACT GGGCTGATGA
>3964174    GTTCCCCCCA CTTCCACTCC CCTCTACTCT CTCTAGGACT GGGCTGATGA
>3705332                                                        A
Consensus   GTTCCCCCCA CTTCCACTCC CCTCTACTCT CTCTAGGACT GGGCTGATGA >1711346IH  AGGCACTGCC CAAAATTTCC CCTACCCCCA ACTTTCCCCT ACCCCCAACT
>3964174    AGGCACTGCC CAAAATTTCC CCTACCCCCA ACTTTNCCCT ACCCCCAACT
>3705332    AGGCACTGCC CAAAATNNCC CCTACCCCCA ACTTTCCCCT ACCCCCAACT
Consensus   AGGCACTGCC CAAAATTTCC CCTACCCCCA ACTTTCCCCT ACCCCCAACT >1711346IH  TTCCCCACCA GCTCCACAAC CCTGTTTGGA GCTACTGCAG GACCAGAAGC
>3964174    TTCCCCACCA GCTCCACAAC CCTGTTTGGA GCTACTGCAG GT
>3705332    TTCCCCACCA GCTCCACAAC CCTGTTTGGA GCTACTGCAG GACCAGAAGC
>2270646               CTCCACAAC CCTGTTTGGA GCTACTGCAG GACCAGAAGC
Consensus   TTCCCCACCA GCTCCACAAC CCTGTTTGGA GCTACTGCAG GACCAGAAGC >1711346IH  ACAAAGTGCG GTTTCCCAAG CCTTTGTCCA TCTCAGCCCC CAGAGTATAT
>3705332    ACAAAGTGCG GTTTCCCAAG CCTTTGTCCA TCTCAGCCCC CAGAGTATAT
>2270646    ACAAAGTGCG GTTTCCCAAG CCTTTGTCCA TCTCAGCCCC CAGAGTATAT
>1810610                                                CC CAGAGTATAT
Consensus   ACAAAGTGCG GTTTCCCAAG CCTTTGTCCA TCTCAGCCCC CAGAGTATAT >1711346IH  CTGTGCTTGG GGAATCTCAC ACAGAAACTC AGGAGCACCC CCTGCCTGAG
>3705332    CTGTGCTTGG GGAATCTCAC ACAGAAACTC AGGAGCACCC CCTGCNTGAG
>2270646    CTGTGCTTGG GGAATCTCAC ACANAAACTC AGGAGCACCC CCTGCCTGAG
>1810610    CTGTGCTTGG GGAATCTCAC ACAGAAACTC AGGAGCACCC CCTGCCTGAG
Consensus   CTGTGCTTGG GGAATCTCAC ACAGAAACTC AGGAGCACCC CCTGCCTGAG
```

FIG. 1D

```
>1711346IH  CTAAGGGAGG TCTTATCTCT CAGGGGGGGT TTAAGTGCCG TTTGCAATAA
 >3705332   CTAAGGGAGG TCTTATCTCT CAGGGGGGGT TTAAGTGCCG TTTGCAATAA
 >2270646   CTAAGGGNGG TC
 >1810610   CTAAGGGAGG TCTTATCTCT CAGGGGGGGT TTAAGTGCCG TTTGCAATAA
 Consensus  CTAAGGGAGG TCTTATCTCT CAGGGGGGGT TTAAGTGCCG TTTGCAATAA >1711346IH  TGTCGTCTTA TTTTTTTAGC GGGGTGAATA TTTTATACTG TAAGTGAGCA
 >3705332   TGTCGTCTTA TTTATTTAGC GGGGTGAATA TTTTATACTG TAA
 >1810610   TGTCGTCTTA TTTATTTAGC GGGGTGAATA TTTTATACTG TAAGTGAGCA
 Consensus  TGTCGTCTTA TTTATTTAGC GGGGTGAATA TTTTATACTG TAAGTGAGCA >1711346IH  ATCAGAGTAT AATGTTTATG GTGACAAAAT TAAAGGCTTT CTTATATGTT
 >1810610   ATCAGAGTAT AATGTTTATG GTGACAAAAT TAAAGGCTTT CTTATATGTT
 Consensus  ATCAGAGTAT AATGTTTATG GTGACAAAAT TAAAGGCTTT CTTATATGTT >1711346IH  TA
 >1810610   T
 Consensus  TA
```

FIG. 1E

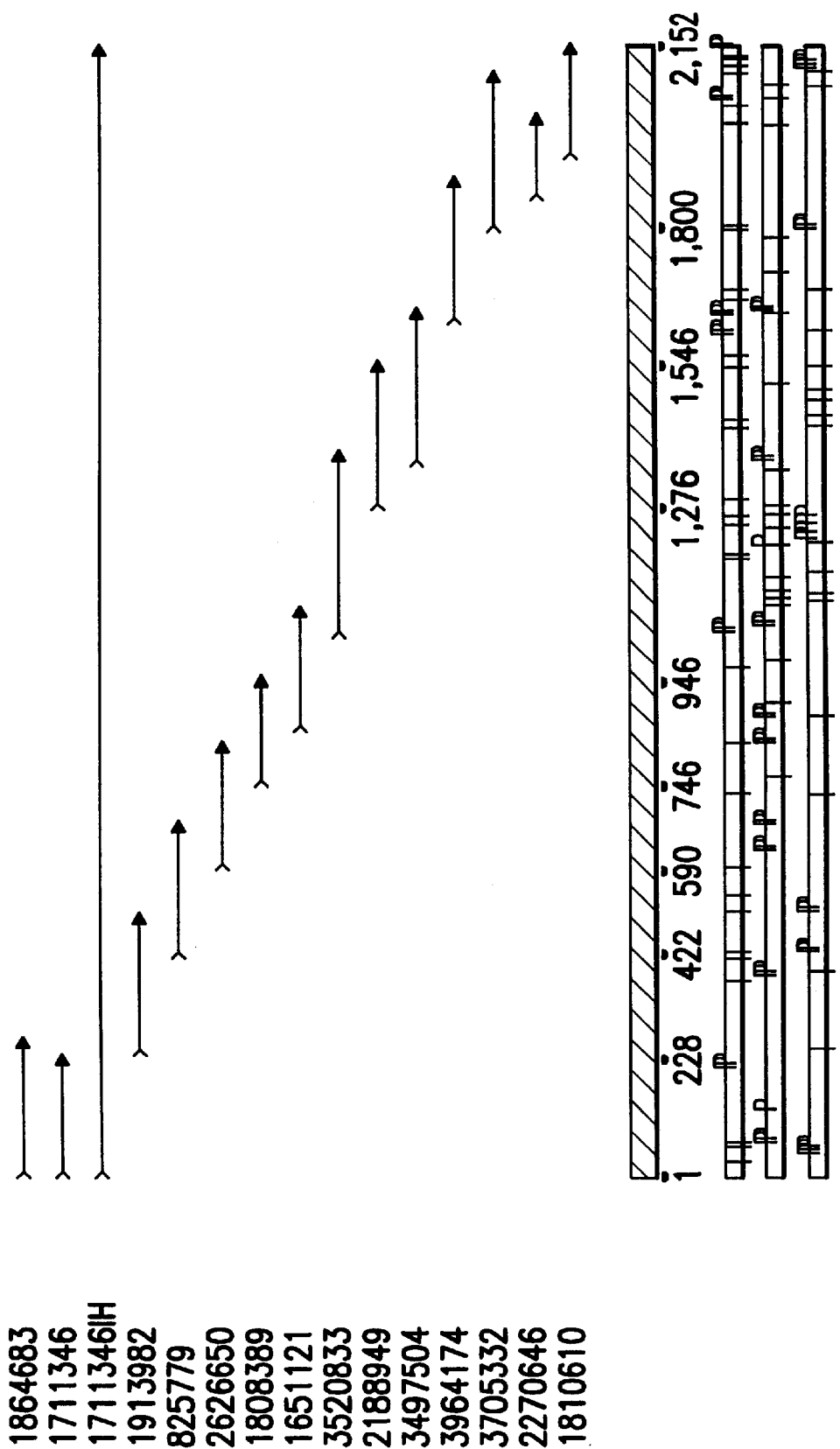

| Lane | Tissue | Lane | Tissue |
|---|---|---|---|
| 1 | 100 bp DNA Marker | 8 | Breast Cancer |
| 2 | Placental DNA | 9 | Breast Cancer |
| 3 | Prostate BPH | 10 | Normal Breast |
| 4 | Prostate Cancer | 11 | Normal Lung |
| 5 | Colon Cancer | 12 | Normal Lung |
| 6 | Colon Cancer | 13 | Lung Cancer |
| 7 | Normal Colon | | |

| Lane | Tissue | Lane | Tissue |
|---|---|---|---|
| 1 | Colon Cancer | 6 | Normal Lung |
| 2 | BPH | 7 | Normal Lung |
| 3 | BPH | 8 | Breast Cancer |
| 4 | BPH | 9 | Breast Cancer |
| 5 | Prostate Cancer | 10 | Mol Wt Markers |

REAGENTS AND METHODS USEFUL FOR DETECTING DISEASES OF THE PROSTATE

This APPLN is a DIVISION of U.S. Ser. No. 09/071,710 filed May 1, 1998 U.S. Pat. No. 6,130,043 which is a CIP of U.S. Ser. No. 08/850,713 filed May 2, 1997 ABN.

CROSS-REFERENCE TO RELATED APPLICATION

This application is a continuation-in-part of U.S. application Ser. No. 08/850,713, filed May 2, 1997, from which priority is claimed pursuant to 35 U.S.C. §120 and which is incorporated herein by reference in its entirety.

BACKGROUND OF THE INVENTION

This invention relates generally to detecting diseases of the prostate. Furthermore, the invention also relates to reagents and methods for detecting diseases of the prostate. More particularly, the present invention relates to reagents such as polynucleotide sequences and the polypeptide sequences encoded thereby, as well as methods which utilize these sequences. The polynucleotide and polypeptide sequences are useful for detecting, diagnosing, staging, monitoring, prognosticating, in vivo imaging, preventing or treating, or determining predisposition to diseases or conditions of the prostate such as prostate cancer.

Prostate cancer is the most common form of cancer occurring in males in the U.S., with projections of 184,500 new cases diagnosed and 39,200 related deaths to occur during 1998 (American Cancer Society). Prostate cancer also has shown the largest increase in incidence as compared to other types of cancer, increasing 142% from 1992 to 1996.

Procedures used for detecting, diagnosing, staging, monitoring, prognosticating, in vivo imaging, preventing or treating, or determining predisposition to diseases or conditions of the prostate such as prostate cancer are of critical importance to the outcome of the patient. For example, patients diagnosed with localized prostate cancer have greater than a 90% five-year survival rate compared to a rate of 25 to 31% for patients diagnosed with distant metastasis. (American Cancer Society statistics). A diagnostic procedure for early detection of prostate cancer should, therefore, specifically detect this disease and be capable of detecting the presence of prostate cancer before symptoms appear.

Such procedures could include assays based upon the appearance of various disease markers in test samples such as blood, plasma, serum, or urine obtained by minimally invasive procedures which are detectable by immunological methods. These procedures would provide information to aid the physician in managing the patient with disease of the prostate and at low cost to the patient. Markers such as the prostate specific antigen (PSA) exist and are used clinically for screening patients for prostate cancer. Elevated levels of PSA protein in serum can be used as a marker in the early detection of prostate cancer in asymptomatic men. G. E. Hanks, et al., In: *Cancer: Principles and Practice of Oncology*, Vol. 1, Fourth Edition, pp. 1073–1113, Philadelphia, Pa.: J.B. Lippincott Co. (1993.). PSA normally is secreted by the prostate at high levels into the seminal fluid, but is present in very low levels in the blood of men with normal prostates. However, in patients with diseases of the prostate including benign prostatic hyperplasia (BPH) and adenocarcinoma of the prostate, the level of PSA can be markedly elevated in the blood and thus be useful as an indicator of prostate disease. PSA, however, cannot differentiate between BPH and prostate cancer, which reduces its specificity as a marker for prostate cancer. M. K. Schwartz, et al., In: *Cancer: Principlcs and Practice of Oncology*, Vol. 1, Fourth Edition, pp. 531–542, Philadelphia, Pa.: J.B. Lippincott Co. 1993. New markers which are more specific for prostate cancer thus would be beneficial in the initial detection of this disease.

A critical step in managing patients with prostate cancer is the presurgical staging of the cancer to provide prognostic value and criteria for designing optimal therapy. Improved procedures for accurately staging prostate cancer prior to surgery are needed. One study demonstrated that current methods of staging prostate cancer prior to surgery were incorrect approximately fifty percent (50%) of the time. F. Labrie, et al., *Urology* 44 (Symposium Issue): 29–37 (1994). Prostate cancer management also could be improved by utilizing new markers found in an inappropriate body compartment. Such markers could be mRNA or protein markers expressed by cells originating from the primary prostate tumor but residing in blood, bone marrow or lymph nodes and could be sensitive indicators for metastasis to these distal organs. For example, in patients with metastatic prostate cancer, PSA protein has been detected by immunohistochemical techniques in bone marrow, and PSA mRNA has been detected by RT-PCR in cells of blood, lymph nodes and bone marrow. K. Pantel, et al., *Onkologie* 18: 394–401 (1995).

New markers which could predict the biologic behavior of early prostate cancers would also be of significant value. Early prostate cancers that threaten or will threaten the life of the patient are more clinically important than those that do not or will not be a threat. G. E. Hanks, supra. A need therefore exists for new markers which can differentiate between the clinically important and unimportant prostate cancers. Such markers would allow the clinician to accurately identify and effectively treat early cancers localized to the prostate which could otherwise metastasize and kill the patient. Further, if one could show that such a marker characteristic of aggressive cancer was absent, the patient could be spared expensive and non-beneficial treatment.

It also would be beneficial to find a prostate associated marker which is more sensitive in detecting recurrence of prostate cancer than PSA and which is not affected by androgens. To date, PSA has proven to be the most sensitive marker for detecting recurrent disease. However, in some cases tumor progression occurs without PSA elevation due to hormonal therapy utilized for treating the cancer. Although the decrease in androgen results in a concomitant decrease in PSA, it does not necessarily reflect a decrease in tumor metastasis. This complication is the result of androgen-stimulated PSA expression. Part of the decline in PSA observed after androgen ablation is due not to tumor cell death but to diminished PSA expression. G. E. Hanks, supra.

It therefore would be advantageous to provide specific methods and reagents for detecting, diagnosing, staging, monitoring, prognosticating, in vivo imaging, preventing or treating, or determining predisposition to diseases and conditions of the prostate, or to indicate possible predisposition to these conditions. Such methods would include assaying a test sample for products of a gene which are overexpressed in prostate diseases and conditions such as cancer. Such methods may also include assaying a test sample for products of a gene alteration associated with prostate disease or condition. Such methods may further include assaying a test sample for products of a gene whose distribution among the various tissues and compartments of the body have been altered by a prostate-associated disease or condition such as cancer. Useful reagents include polynucleotide(s), or fragment(s) thereof which may be used in diagnostic methods such as reverse transcriptase-polymerase chain reaction (RT-PCR), PCR, or hybridization assays of mRNA extracted from biopsied tissue, blood or other test samples; polypeptides or proteins which are the translation products of such mRNAs; or antibodies directed against these polypeptides or proteins. Drug treatment or gene therapy for diseases or conditions of the prostate can then be based on these identified gene sequences or their expressed proteins and efficacy of any particular therapy can be monitored. Furthermore, it would be advantageous to have available alternative, non-surgical diagnostic methods capable of detecting early stage prostate disease such as cancer.

SUMMARY OF THE INVENTION

The present invention provides a method of detecting a target PS108 polynucleotide in a test sample, which method comprises contacting the test sample with at least one PS108-specific polynucleotide and detecting the presence of the target PS108 polynucleotide in the test sample. The PS108-specific polynucleotide has at least 50% identity with a polynucleotide selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8, SEQUENCE ID NO 9, SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 16 ("SEQUENCE ID NOS 1–16"), and fragments or complements thereof. Also, the PS108-specific polynucleotide may be attached to a solid phase prior to performing the method.

The present invention also provides a method for detecting PS108 mRNA in a test sample, which comprises performing reverse transcription (RT) with at least one primer in order to produce cDNA, amplifying the cDNA so obtained using PS108 oligonucleotides as sense and anti-sense primers to obtain PS108 amplicon, and detecting the presence of the PS108 amplicon as an indication of the presence of PS108 mRNA in the test sample, wherein the PS108 oligonucleotides have at least 50% identity to a sequence selected from the group consisting of SEQUENCE ID NOS 1–16, and fragments or complements thereof. Amplification can be performed by the polymerase chain reaction. Also, the test sample can be reacted with a solid phase prior to performing the method, prior to amplification or prior to detection. This reaction can be a direct or an indirect reaction. Further, the detection step can comprise utilizing a detectable label capable of generating a measurable signal. The detectable label can be attached to a solid phase.

The present invention further provides a method of detecting a target PS108 polynucleotide in a test sample suspected of containing target PS108 polynucleotides, which comprises (a) contacting the test sample with at least one PS108 oligonucleotide as a sense primer and at least one PS108 oligonucleotide as an anti-sense primer, and amplifying same to obtain a first stage reaction product; (b) contacting the first stage reaction product with at least one other PS108 oligonucleotide to obtain a second stage reaction product, with the proviso that the other PS108 oligonucleotide is located 3' to the PS108 oligonucleotides utilized in step (a) and is complementary to the first stage reaction product; and (c) detecting the second stage reaction product as an indication of the presence of a target PS108 polynucleotide in the test sample. The PS108 oligonucleotides selected as reagents in the method have at least 50% identity with a sequence selected from the group consisting of SEQUENCE ID NOS 1–16, and fragments or complements thereof. Amplification may be performed by the polymerase chain reaction. The test sample can be reacted either directly or indirectly with a solid phase prior to performing the method, or prior to amplification, or prior to detection. The detection step also comprises utilizing a detectable label capable of generating a measurable signal; further, the detectable label can be attached to a solid phase. Test kits useful for detecting target PS108 polynucleotides in a test sample are also provided which comprise a container containing at least one PS108-specific polynucleotide selected from the group consisting of SEQUENCE ID NOS 1–16, and fragments or complements thereof. These test kits further comprise containers with tools useful for collecting test samples (such as, for example, blood, urine, saliva and stool). Such tools include lancets and absorbent paper or cloth for collecting and stabilizing blood; swabs for collecting and stabilizing saliva; and cups for collecting and stabilizing urine or stool samples. Collection materials, such as papers, cloths, swabs, cups, and the like, may optionally be treated to avoid denaturation or irreversible adsorption of the sample. The collection materials also may be treated with or contain preservatives, stabilizers or antimicrobial agents to help maintain the integrity of the specimens.

The present invention also provides a purified polynucleotide or fragment thereof derived from a PS108 gene. The purified polynucleotide is capable of selectively hybridizing to the nucleic acid of the PS108 gene, or a complement thereof. The polynucleotide has at least 50% identity with a polynucleotide selected from the group consisting of SEQUENCE ID NOS 1–16, and fragments or complements thereof. Further, the purified polynucleotide can be produced by recombinant and/or synthetic techniques. The purified recombinant polynucleotide can be contained within a recombinant vector. The invention further comprises a host cell transfected with the recombinant vector.

The present invention further provides a recombinant expression system comprising a nucleic acid sequence that includes an open reading frame derived from PS108. The nucleic acid sequence has at least 50% identity with a sequence selected from the group consisting of SEQUENCE ID NOS 1–16, and fragments or complements thereof. The nucleic acid sequence is operably linked to a control sequence compatible with a desired host. Also provided is a cell transfected with this recombinant expression system.

The present invention also provides a polypeptide encoded by PS108. The polypeptide can be produced by recombinant technology, provided in purified form, or produced by synthetic techniques. The polypeptide comprises an amino acid sequence which has at least 50% identity with an amino acid sequence selected from At the group consisting of SEQUENCE ID NO 36, SEQUENCE ID NO 37, SEQUENCE ID NO 38, SEQUENCE ID NO 39, and fragments thereof.

Also provided is an antibody which specifically binds to at least one PS108 epitope. The antibody can be a polyclonal or monoclonal antibody. The epitope is derived from an amino acid sequence selected from the group consisting of SEQUENCE ID NO 36, SEQUENCE ID NO 37, SEQUENCE ID NO 38, SEQUENCE ID NO 39, and fragments thereof. Assay kits for determining the presence of PS108 antigen or anti-PS108 antibody in a test sample are also included. In one embodiment, the assay kits comprise a container containing at least one PS108 polypeptide having at least 50% identity with an amino acid sequence selected from the group consisting of SEQUENCE ID NO 36, SEQUENCE ID NO 37, SEQUENCE ID NO 38, SEQUENCE ID NO 39, and fragments thereof. Further, the test kit can comprise a container with tools useful for collecting test samples (such as blood, urine, saliva, and stool). Such tools include lancets and absorbent paper or cloth for collecting and stabilizing blood; swabs for collecting and stabilizing saliva; and cups for collecting and stabilizing urine or stool samples. Collection materials such as papers, cloths, swabs, cups, and the like, may optionally be treated to avoid denaturation or irreversible adsorption of the sample. These collection materials also may be treated with or contain preservatives, stabilizers or antimicrobial agents to help maintain the integrity of the specimens. Also, the polypeptide can be attached to a solid phase.

In another embodiment of the invention, antibodies or fragments thereof against the PS108 antigen can be used to detect or image localization of the antigen in a patient for the purpose of detecting or diagnosing a disease or condition. Such antibodies can be polyclonal or monoclonal, or made by molecular biology techniques, and can be labeled with a variety of detectable labels, including but not limited to radioisotopes and paramagnetic metals. Furthermore, antibodies or fragments thereof, whether monoclonal, polyclonal, or made by molecular biology techniques, can be used as therapeutic agents for the treatment of diseases characterized by expression of the PS108 antigen. In the case of therapeutic applications, the antibody may be used without derivitization, or it may be derivitized with a cytotoxic agent such as a radioisotope, enzyme, toxin, drug, prodrug, or the like.

Another assay kit for determining the presence of PS108 antigen or anti-PS108 antibody in a test sample comprises a container containing an antibody which specifically binds to a PS108 antigen, wherein the PS108 antigen comprises at least one PS108-encoded epitope. The PS108 antigen has at least about 60% sequence similarity to a sequence of a PS108-encoded antigen selected from the group consisting of SEQUENCE ID NO 36, SEQUENCE ID NO 37, SEQUENCE ID NO 38, SEQUENCE ID NO 39, and fragments thereof. These test kits can further comprise containers with tools useful for collecting test samples (such as blood, urine, saliva, and stool). Such tools include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. These collection materials also may be treated with, or contain, preservatives, stabilizers or antimicrobial agents to help maintain the integrity of the specimens. The antibody can be attached to a solid phase.

A method for producing a polypeptide which contains at least one epitope of PS108 is provided, which method comprises incubating host cells transfected with an expression vector. This vector comprises a polynucleotide sequence encoding a polypeptide, wherein the polypeptide comprises an amino acid sequence having at least 50% identity with a PS108 amino acid sequence selected from the group consisting of SEQUENCE ID NO 36, SEQUENCE ID NO 37, SEQUENCE ID NO 38, SEQUENCE ID NO 39, and fragments thereof.

A method for detecting PS108 antigen in a test sample suspected of containing PS108 antigen also is provided. The method comprises contacting the test sample with an antibody or fragment thereof which specifically binds to at least one epitope of PS108 antigen, for a time and under conditions sufficient for the formation of antibody/antigen complexes; and detecting the presence of such complexes containing the antibody as an indication of the presence of PS108 antigen in the test sample. The antibody can be attached to a solid phase and may be either a monoclonal or polyclonal antibody. Furthermore, the antibody specifically binds to at least one PS108 antigen selected from the group consisting of SEQUENCE ID NO 36, SEQUENCE ID NO 37, SEQUENCE ID NO 38, SEQUENCE ID NO 39, and fragments thereof.

Another method is provided which detects antibodies which specifically bind to PS108 antigen in a test sample suspected of containing these antibodies. The method comprises contacting the test sample with a polypeptide which contains at least one PS108 epitope, wherein the PS108 epitope comprises an amino acid sequence having at least 50% identity with an amino acid sequence encoded by a PS108 polynucleotide, or a fragment thereof. Contacting is carried out for a time and under conditions sufficient to allow antigen/antibody complexes to form. The method further entails detecting complexes which contain the polypeptide. The polypeptide can be attached to a solid phase. Further, the polypeptide can be a recombinant protein or a synthetic peptide having at least 50% identity with an amino acid sequence selected from the group consisting of SEQUENCE ID NO 36, SEQUENCE ID NO 37, SEQUENCE ID NO 38, SEQUENCE ID NO 39, and fragments thereof.

The present invention provides a cell transfected with a PS108 nucleic acid sequence that encodes at least one epitope of a PS108 antigen, or fragment thereof. The nucleic acid sequence is selected from the group consisting of SEQUENCE ID NOS 1–16, and fragments or complements thereof.

A method for producing antibodies to PS108 antigen also is provided, which method comprises administering to an individual an isolated immunogenic polypeptide or fragment thereof, wherein the isolated immunogenic polypeptide comprises at least one PS108 epitope. The immunogenic polypeptide is administered in an amount sufficient to produce an immune response. The isolated, immunogenic polypeptide comprises an amino acid sequence selected from the group consisting of SEQUENCE ID NO 36, SEQUENCE ID NO 37, SEQUENCE ID NO 38, SEQUENCE ID NO 39, and fragments thereof.

Another method for producing antibodies which specifically bind to PS108 antigen is disclosed, which method comprises administering to an individual a plasmid comprising a nucleic acid sequence which encodes at least one PS108 epitope derived from an amino acid sequence selected from the group consisting of SEQUENCE ID NO 36, SEQUENCE ID NO 37, SEQUENCE ID NO 38, SEQUENCE ID NO 39, and fragments thereof. The plasmid is administered in an amount such that the plasmid is taken up by cells in the individual and expressed at levels sufficient to produce an immune response.

Also provided is a composition of matter that comprises a PS108 polynucleotide of at least about 10–12 nucleotides having at least 50% identity with a polynucleotide selected from the group consisting of SEQUENCE ID NOS 1–16, and fragments or complements thereof. The PS108 polynucleotide encodes an amino acid sequence having at least one PS108 epitope. Another composition of matter provided by the present invention comprises a polypeptide with at least one PS108 epitope of about 8–10 amino acids. The polypeptide comprises an amino acid sequence having at least 50% identity with an amino acid sequence selected from the group consisting of SEQUENCE ID NO 36, SEQUENCE ID NO 37, SEQUENCE ID NO 38, SEQUENCE ID NO 39, and fragments thereof. Also provided is a gene, or fragment thereof, coding for a PS108 polypeptide which has at least 50% identity to SEQUENCE ID NO 36; and a gene, or a fragment thereof, comprising DNA having at least 50% identity with SEQUENCE ID NO 15 or SEQUENCE ID NO 16.

BRIEF DESCRIPTION OF THE DRAWINGS

FIGS. 1A–1E show the nucleotide alignment of clones 1864683 (SEQUENCE ID NO 1), 1711346 (SEQUENCE ID NO 2), 1913982 (SEQUENCE ID NO 3), 825779 (SEQUENCE ID NO 4), 2626650 (SEQUENCE ID NO 5), 1808389 (SEQUENCE ID NO 6), 1651121 (SEQUENCE ID NO 7), 3520833 (SEQUENCE ID NO 8), 2188949 (SEQUENCE ID NO 9), 3497504 (SEQUENCE ID NO 10), 3964174 (SEQUENCE ID NO 11), 3705332 (SEQUENCE ID NO 12), 2270646 (SEQUENCE ID NO 13), 1810610 (SEQUENCE ID NO 14), the full-length sequence of clone 1711346 (designated as clone 1711346IH (SEQUENCE ID NO 15)), and the consensus sequence (SEQUENCE ID NO 16) derived therefrom.

FIG. 2 shows the contig map depicting the formation of the consensus nucleotide sequence (SEQUENCE ID NO 16) from the nucleotide alignment of overlapping clones 1864683 (SEQUENCE ID NO 1), 1711346 (SEQUENCE ID NO 2), 1913982 (SEQUENCE ID NO 3), 825779 (SEQUENCE ID NO 4), 2626650 (SEQUENCE ID NO 5), 1808389 (SEQUENCE ID NO 6), 1651121 (SEQUENCE ID NO 7), 3520833 (SEQUENCE ID NO 8), 2188949 (SEQUENCE ID NO 9),3497504 (SEQUENCE ID NO 10), 3964174 (SEQUENCE ID NO 11), 3705332 (SEQUENCE ID NO 12), 2270646 (SEQUENCE ID NO 13), 1810610 (SEQUENCE ID NO 14), and 1711346IH (SEQUENCE ID NO 15).

DETAILED DESCRIPTION OF THE INVENTION

Figure 3A:
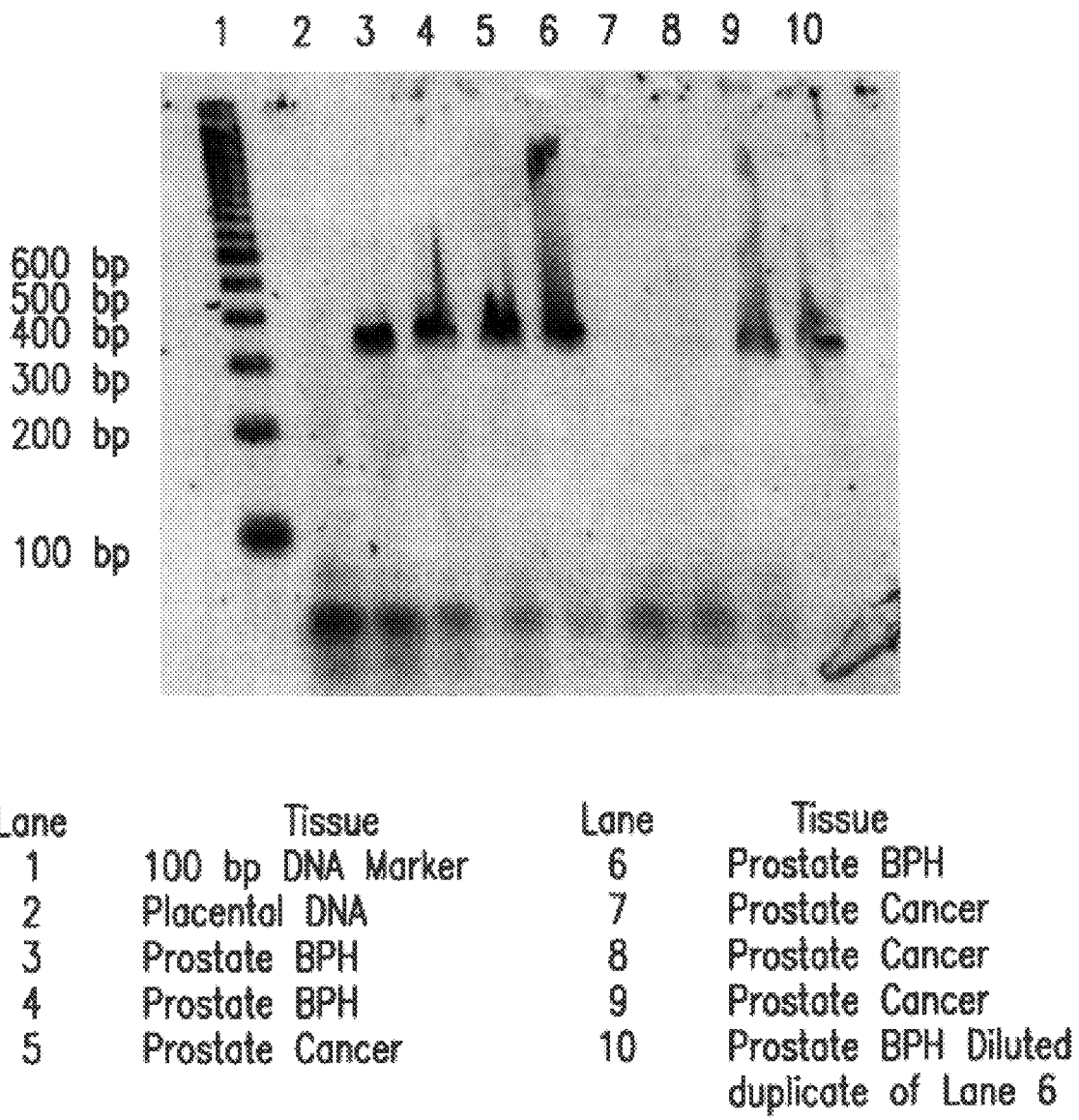
FIG. 3A is a scan of a SYBR® Green-stained agarose gel of PS108 RNA-specific RT-PCR amplification products from prostate tissue RNAs.

The present invention provides a gene, or a fragment thereof, which codes for a PS108 polypeptide having at least about 50% identity to SEQUENCE ID NO 36. The present invention further encompasses a PS108 gene, or a fragment thereof, comprising DNA which has at least about 50% identity with SEQUENCE ID NO 15 or SEQUENCE ID NO 16.

The present invention also provides methods for assaying a test sample for products of a prostate tissue gene designated as PS108, which comprises making cDNA from mRNA in the test sample, and detecting the cDNA as an indication of the presence of prostate tissue gene PS108. The method may include an amplification step, wherein one or more portions of the mRNA from PS108 corresponding to the gene or fragments thereof, is amplified. Methods also are provided for assaying for the translation products of PS108.

Test samples which may be assayed by the methods provided herein include tissues, cells, body fluids and secretions. The present invention also provides reagents such as oligonucleotide primers and polypeptides which are useful in performing these methods.

Portions of the nucleic acid sequences disclosed herein are useful as primers for the reverse transcription of RNA or for the amplification of cDNA; or as probes to determine the presence of certain mRNA sequences in test samples. Also disclosed are nucleic acid sequences which permit the production of encoded polypeptide sequences which are useful as standards or reagents in diagnostic immunoassays, as targets for pharmaceutical screening assays and/or as components or as target sites for various therapies. Monoclonal and polyclonal antibodies directed against at least one epitope contained within these polypeptide sequences are useful as delivery agents for therapeutic agents as well as for diagnostic tests and for screening for diseases or conditions associated with PS108, especially prostate cancer. Isolation of sequences of other portions of the gene of interest can be accomplished utilizing probes or PCR primers derived from these nucleic acid sequences. This allows additional probes of the mRNA or cDNA of interest to be established, as well as corresponding encoded polypeptide sequences. These additional molecules are useful in detecting, diagnosing, staging, monitoring, prognosticating, in vivo imaging, preventing or treating, or determining the predisposition to diseases and conditions of the prostate, such as prostate cancer, characterized by PS108, as disclosed herein.

Techniques for determining amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity." Two or more amino acid sequences likewise can be compared by determining their "percent identity." The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known in the art.

The compositions and methods described herein will enable the identification of certain markers as indicative of a prostate tissue disease or condition; the information obtained therefrom will aid in the detecting, diagnosing, staging, monitoring, prognosticating, in vivo imaging, preventing or treating, or determining diseases or conditions associated with PS108, especially prostate cancer. Test methods include, for example, probe assays which utilize the sequencers) provided herein and which also may utilize nucleic acid amplification methods such as the polymerase chain reaction (PCR), the ligase chain reaction (LCR), and hybridization. In addition, the nucleotide sequences provided herein contain open reading frames from which an immunogenic epitope may be found. This epitope is believed to be unique to the disease state or condition associated with PS108. It also is thought that the polynucleotides or polypeptides and protein encoded by the PS108 gene are useful as a marker. This marker is either elevated in disease such as prostate cancer, altered in disease such as prostate cancer, or present as a normal protein but appearing in an inappropriate body compartment. The uniqueness of the epitope may be determined by (i) its immunological reactivity and specificity with antibodies directed against proteins and polypeptides encoded by the PS108 gene, and (ii) its nonreactivity with any other tissue markers. Methods for determining immunological reactivity are well-known and include, but are not limited to, for example, radioimmunoassay (RIA), enzyme-linked immunoabsorbent assay (ELISA), hemagglutination (HA), fluorescence polarization immunoassay (FPIA), chemiluminescent immunoassay (CLIA) and others. Several examples of suitable methods are described herein.

Unless otherwise stated, the following terms shall have the following meanings:

A polynucleotide "derived from" or "specific for" a designated sequence refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the designated nucleotide sequence. The sequence may be complementary or identical to a sequence which is unique to a particular polynucleotide sequence as determined by techniques known in the art. Comparisons to sequences in databanks, for example, can be used as a method to determine the uniqueness of a designated sequence. Regions from which sequences may be derived, include but are not limited to, regions encoding specific epitopes, as well as non-translated and/or non-transcribed regions.

The derived polynucleotide will not necessarily be derived physically from the nucleotide sequence of interest under study, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified in ways known in the art to be consistent with the intended use.

A "fragment" of a specified polynucleotide refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the specified nucleotide sequence.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., PNA as defined hereinbelow) which can be used to identify a specific polynucleotide present in samples bearing the complementary sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence. Thus, a "polypeptide," "protein," or "amino acid" sequence has at least about 50% identity, preferably about 60% identity, more preferably about 75–85% identity, and most preferably about 90–95% or mote identity to a PS108 amino acid sequence. Further, the PS108 "polypeptide," "protein," or "amino acid" sequence may have at least about 60% similarity, preferably at least about 75% similarity, more preferably about 85% similarity, and most preferably about 95% or more similarity to a polypeptide or amino acid sequence of PS108. This amino acid sequence can be selected from the group consisting of SEQUENCE ID NO 36, SEQUENCE ID NO 37, SEQUENCE ID NO 38, SEQUENCE ID NO 39, and fragments thereof.

A "recombinant polypeptide," "recombinant protein," or "a polypeptide produced by recombinant techniques," which terms may be used interchangeably herein, describes a polypeptide which by virtue of its origin or manipulation is not associated with all or a portion of the polypeptide with which it is associated in nature and/or is linked to a polypeptide other than that to which it is linked in nature. A recombinant or encoded polypeptide or protein is not necessarily translated from a designated nucleic acid sequence. It also may be generated in any manner, including chemical synthesis or expression of a recombinant expression system.

The term "synthetic peptide" as used herein means a polymeric form of amino acids of any length, which may be chemically synthesized by methods well-known to the routineer. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as methylation or capping and unmodified forms of the polynucleotide. The terms "polynucleotide," "oligomer," "oligonucleotide," and "oligo" are used interchangeably herein.

"A sequence corresponding to a cDNA" means that the sequence contains a polynucleotide sequence that is identical or complementary to a sequence in the designated DNA. The degree (or "percent") of identity or complementarity to the cDNA will be approximately 50% or greater, preferably at least about 70% or greater, and more preferably at least about 90% or greater. The sequence that corresponds to the identified cDNA will be at least about 50 nucleotides in length, preferably at least about 60 nucleotides in length, and more preferably at least about 70 nucleotides in length. The correspondence between the gene or gene fragment of interest and the cDNA can be determined by methods known in the art and include, for example, a direct comparison of the sequenced material with the cDNAs described, or hybridization and digestion with single strand nucleases, followed by size determination of the digested fragments.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

"Purified polypeptide" or "purified protein" means a polypeptide of interest or fragment thereof which is essentially free of, e.g., contains less than about 50%, preferably less than about 70%, and more preferably less than about 90%, cellular components with which the polypeptide of interest is naturally associated. Methods for purifying polypeptides of interest are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" and "protein" are used interchangeably herein and indicate at least one molecular chain of amino acids linked through covalent and/or non-covalent bonds. The terms do not refer to a specific length of the product. Thus peptides, oligopeptides and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

A "fragment" of a specified polypeptide refers to an amino acid sequence which comprises at least about 3–5 amino acids, more preferably at least about 8–10 amino acids, and even more preferably at least about 15–20 amino acids derived from the specified polypeptide.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to a polynucleotide sequence which is necessary to effect the expression of a coding sequence to which it is ligated. The nature of such control sequences differs depending upon the host organism. In prokaryotes, such control sequences generally include a promoter, a ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

The term "open reading frame" or "ORF" refers to a region of a polynucleotide sequence which encodes a polypeptide. This region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be determined by computer searches of known data banks, such as GenBank, for the polynucleotide sequence which encodes the epitope and by amino acid sequence comparisons with other known proteins.

As used herein, "epitope" means an antigenic determinant of a polypeptide or protein. Conceivably, an epitope can comprise three amino acids in a spatial conformation which is unique to the epitope. Generally, an epitope consists of at least five such amino acids and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of a specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly, by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The term "transfection" refers to the introduction of an exogenous polynucleotide into a prokaryotic or eucaryotic host cell, irrespective of the method used for the introduction. The term "transfection" refers to both stable and transient introduction of the polynucleotide, and encompasses direct uptake of polynucleotides, transformation, transduction, and f-mating. Once introduced into the host cell, the exogenous polynucleotide may be maintained as a non-integrated replicon, for example, a plasmid, or alternatively, may be integrated into the host genome.

"Treatment" refers to prophylaxis and/or therapy.

The term "individual" as used herein refers to vertebrates, particularly members of the mammalian species and includes, but is not limited to, domestic animals, sports animals, primates and humans; more particularly, the term refers to humans.

The term "sense strand" or "plus strand" (or "+") as used herein denotes a nucleic acid that contains the sequence that encodes the polypeptide. The term "antisense strand" or "minus strand" (or "−") denotes a nucleic acid that contains a sequence that is complementary to that of the "plus" strand.

The term "test sample" refers to a component of an individual's body which is the source of the analyte (such as antibodies of interest or antigens of interest). These components are well known in the art. A test sample is typically anything suspected of containing a target sequence. Test samples can be prepared using methodologies well known in the art such as by obtaining a specimen from an individual and, if necessary, disrupting any cells contained thereby to release target nucleic acids. These test samples include biological samples which can be tested by the methods of the present invention described herein and include human and animal body fluids such as whole blood, serum, plasma, cerebrospinal fluid, sputum, bronchial washing, bronchial aspirates, urine, lymph fluids, and various external secretions of the respiratory, intestinal and genitourinary tracts, tears, saliva, milk, white blood cells, myelomas and the like; biological fluids such as cell culture supernatants; tissue specimens which may be fixed; and cell specimens which may be fixed.

"Purified product" refers to a preparation of the product which has been isolated from the cellular constituents with which the product is normally associated and from other types of cells which may be present in the sample of interest.

"PNA" denotes a "peptide nucleic acid analog" which may be utilized in a procedure such as an assay described herein to determine the presence of a target. "MA" denotes a "morpholino analog" which may be utilized in a procedure such as an assay described herein to determine the presence of a target. See, for example, U.S. Pat. No. 5,378,841, which is incorporated herein by reference. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with ("attached to") such signal generating compounds as fluorescein, radionucleotides, chemiluminescent compounds and the like. PNAs or other nucleic acid analogs such as MAs thus can be used in assay methods in place of DNA or RNA. Although assays are described herein utilizing DNA probes, it is within the scope of the routineer that PNAs or MAs can be substituted for RNA or DNA with appropriate changes if and as needed in assay reagents.

"Analyte," as used herein, is the substance to be detected which may be present in the test sample. The analyte can be any substance for which there exists a naturally occurring specific binding member (such as an antibody), or for which a specific binding member can be prepared. Thus, an analyte is a substance that can bind to one or more specific binding members in an assay. "Analyte" also includes any antigenic substances, haptens, antibodies and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a polypeptide, an amino acid, a nucleotide target and the like. The analyte can be soluble in a body fluid such as blood, blood plasma or serum, urine or the like. The analyte can be in a tissue, either on a cell surface or within a cell. The analyte can be on or in a cell dispersed in a body fluid such as blood, urine, breast aspirate, or obtained as a biopsy sample.

The terms "diseases of the prostate," "prostate disease," and "condition of the prostate" are used interchangeably herein to refer to any disease or condition of the prostate including, but not limited to, benign prostatic hyperplasia (BPH), prostatitis, prostatic intraepithelial neoplasia (PIN) and cancer.

"Prostate cancer," as used herein, refers to any malignant disease of the prostate including, but not limited to, adenocarcinoma, small cell undifferentiated carcinoma and mucinous (colloid) cancer.

An "Expressed Sequence Tag" or "EST" refers to the partial sequence of a cDNA insert which has been made by reverse transcription of mRNA extracted from a tissue followed by insertion into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal and complexes thereof, including those formed by recombinant DNA molecules.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme and the like. An immunoreactive specific binding member can be an antibody, an antigen, or an antibody/antigen complex that is capable of binding either to the polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazole or adamantane.

The various "signal-generating compounds" (labels) contemplated include chromagens, catalysts such as enzymes, luminescent compounds such as fluorescein and rhodamine, chemiluminescent compounds such as dioxetanes, acridiniums, phenanthridiniums and luminol, radioactive elements and direct visual labels. Examples of enzymes include alkaline phosphatase, horseradish peroxidase, beta-galactosidase and the like. The selection of a particular label is not critical, but it must be capable of producing a signal either by itself or in conjunction with one or more additional substances.

"Solid phases" ("solid supports") are known to those in the art and include the walls of wells of a reaction tray, test tubes, polystyrene beads, magnetic or non-magnetic beads, nitrocellulose strips, membranes, microparticles such as latex particles, sheep (or other animal) red blood cells and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase," as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent.

As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structures generally are preferred, but materials with a gel structure in the hydrated state may be used as well. Such useful solid supports include, but are not limited to, nitrocellulose and nylon. It is contemplated that such porous solid supports described herein preferably are in the form of sheets of thickness from about 0.01 to 0.5 mm, preferably about 0.1 mm. The pore size may vary within wide limits and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

Reagents.

The present invention provides reagents such as polynucleotide sequences derived from a prostate tissue of interest and designated as PS108, polypeptides encoded thereby and antibodies specific for these polypeptides. The present invention also provides reagents such as oligonucleotide fragments derived from the disclosed polynucleotides and nucleic acid sequences complementary to these polynucleotides. The polynucleotides, polypeptides, or antibodies of the present invention may be used to provide information leading to the detecting, diagnosing, staging, monitoring, prognosticating, in vivo imaging, preventing or treating of, or determining the predisposition to, diseases and conditions of the prostate, such as prostate cancer. The sequences disclosed herein represent unique polynucleotides which can be used in assays or for producing a specific profile of gene transcription activity. Such assays are disclosed in European Patent Number 0373203B1 and International Publication No. WO 95/11995, which are hereby incorporated by reference.

Selected PS108-derived polynucleotides can be used in the methods described herein for the detection of normal or altered gene expression. Such methods may employ PS108 polynucleotides or oligonucleotides, fragments or derivatives thereof, or nucleic acid sequences complementary thereto.

The polynucleotides disclosed herein, their complementary sequences, or fragments of either, can be used in assays to detect, amplify or quantify genes, nucleic acids, cDNAs or mRNAs relating to prostate tissue disease and conditions associated therewith. They also can be used to identify an entire or partial coding region of a PS108 polypeptide. They further can be provided in individual containers in the form of a kit for assays, or provided as individual compositions. If provided in a kit for assays, other suitable reagents such as buffers, conjugates and the like may be included.

The polynucleotide may be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (anti-sense) strand. The coding sequence which encodes the polypeptide may be identical to the coding sequence provided herein or may be a different coding sequence which coding sequence, as a result of the redundancy or degeneracy of the genetic code, encodes the same polypeptide as the DNA provided herein.

This polynucleotide may include only the coding sequence for the polypeptide, or the coding sequence for the polypeptide and an additional coding sequence such as a leader or secretory sequence or a proprotein sequence, or the coding sequence for the polypeptide (and optionally an additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence which is a naturally occurring allelic variant of the coding sequence provided herein.

In addition, the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the polypeptide. The polynucleotides may also encode for a proprotein which is the protein plus additional 5' amino acid residues. A protein having a prosequence is a proprotein and may, in some cases, be an inactive form of the protein. Once the prosequence is cleaved, an active protein remains. Thus, the polynucleotide of the present invention may encode for a protein, or for a protein having a prosequence, or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the polypeptide fused to the marker in the case of a bacterial host, or, for example, the marker sequence may be a hemagglutinin (HA) tag when a mammalian host, e.g. a COS-7 cell line, is fused. The HA tag corresponds to an epitope derived from the influenza hemagglutinin protein. See, for example, I. Wilson et al., Cell 37:767 (1984).

It is contemplated that polynucleotides will be considered to hybridize to the sequences provided herein if there is at least 50%, preferably at least 70%, and more preferably at least 90% identity between the polynucleotide and the sequence.

The present invention also provides an antibody produced by using a purified PS108 polypeptide of which at least a portion of the polypeptide is encoded by a PS108 polynucleotide selected from the polynucleotides provided herein.

These antibodies may be used in the methods provided herein for the detection of PS108 antigen in test samples. The presence of PS108 antigen in the test samples is indicative of the presence of a prostate disease or condition. The antibody also may be used for therapeutic purposes, for example, in neutralizing the activity of PS108 polypeptide in conditions associated with altered or abnormal expression.

The present invention further relates to a PS108 polypeptide which has the deduced amino acid sequence as provided herein, as well as fragments, analogs and derivatives of such polypeptide. The polypeptide of the present invention may be a recombinant polypeptide, a natural purified polypeptide or a synthetic polypeptide. The fragment, derivative or analog of the PS108 polypeptide may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence which is employed for purification of the polypeptide or a proprotein sequence. Such fragments, derivatives and analogs are within the scope of the present invention. The polypeptides and polynucleotides of the present invention are provided preferably in an isolated form and preferably purified.

Thus, a polypeptide of the present invention may have an amino acid sequence that is identical to that of the naturally occurring polypeptide or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine. In contrast, variations may include nonconservative changes, e.g., replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

Probes constructed according to the polynucleotide sequences of the present invention can be used in various assay methods to provide various types of analysis. For example, such probes can be used in fluorescent in situ hybridization (FISH) technology to perform chromosomal analysis, and used to identify cancer-specific structural alterations in the chromosomes, such as deletions or translocations that are visible from chromosome spreads or detectable using PCR-generated and/or allele specific oligonucleotides probes, allele specific amplification or by direct sequencing. Probes also can be labeled with radioisotopes, directly- or indirectly-detectable haptens, or fluorescent molecules, and utilized for in situ hybridization studies to evaluate the mRNA expression of the gene comprising the polynucleotide in tissue specimens or cells.

This invention also provides teachings as to the production of the polynucleotides and polypeptides provided herein.

Probe Assays

The sequences provided herein may be used to produce probes which can be used in assays for the detection of nucleic acids in test samples. The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multi-gene family or in related species like mouse and man.

The polymerase chain reaction (PCR) is a technique for amplifying a desired nucleic acid sequence (target) contained in a nucleic acid or mixture thereof. In PCR, a pair of primers are employed in excess to hybridize to the complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to target The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al, published Jul. 31, 1991, both of which are incorporated herein by reference.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall et al., *PCR Methods and Applications* 4: 80–84 (1994), which also is incorporated herein by reference.

Other known amplification methods which can be utilized herein include but are not limited to the so-called "NASBA" or "3SR" technique described by J. C. Guatelli et al., *PNAS U.S.A.* 87:1874–1878 (1990) and also described by J. Compton, *Nature* 350 (No. 6313):91–92 (1991); Q-beta amplification as described in published European Patent Application (EPA) No. 4544610; strand displacement amplification (as described in G. T. Walker et al., *Clin. Chem.* 42:9–13 [1996]) and European Patent Application No. 684315; and target mediated amplification, as described in International Publication No. WO 93/22461.

Detection of PS108 may be accomplished using any suitable detection method, including those detection methods which are currently well known in the art, as well as detection strategies which may evolve later. Examples of the foregoing presently known detection methods are hereby incorporated herein by reference. See, for example, Caskey et al., U.S. Pat. No. 5,582,989, Gelfand et al., U.S. Pat. No. 5,210,015. Examples of such detection methods include target amplification methods as well as signal amplification technologies. An example of presently known detection methods would include the nucleic acid amplification technologies referred to as PCR, LCR, NASBA, SDA, RCR and TMA. See, for example, Caskey et al., U.S. Pat. No. 5,582,989, Gelfand et al., U.S. Pat. No. 5,210,015. All of the foregoing are hereby incorporated by reference. Detection may also be accomplished using signal amplification such as that disclosed in Snitman et al., U.S. Pat. No. 5,273,882. While the amplification of target or signal is preferred at present, it is contemplated and within the scope of the present invention that ultrasensitive detection methods which do not require amplification can be utilized herein.

Detection, both amplified and non-amplified, may be (combined) carried out using a variety of heterogeneous and homogeneous detection formats. Examples of heterogeneous detection formats are disclosed in Snitman et al., U.S. Pat. No. 5,273,882, Albarella et al in EP-84114441.9, Urdea et al., U.S. Pat. No. 5,124,246, Ullman et al. U.S. Pat. No. 5,185,243 and Kourilsky et al., U.S. Pat. No. 4,581,333. All of the foregoing are hereby incorporated by reference. Examples of homogeneous detection formats are. disclosed in, Caskey et al., U.S. Pat. No. 5,582,989, Gelfand et al., U.S. Pat. No. 5,210,015, which are incorporated herein by reference. Also contemplated and within the scope of the present invention is the use of multiple probes in the hybridization assay, which use improves sensitivity and amplification of the PS108 signal. See, for example, Caskey et al., U.S. Pat. No. 5,582,989, Gelfand et al., U.S. Pat. No. 5,210,015, which are incorporated herein by reference.

In one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method provided herein are labeled with capture and detection labels, wherein probes are labeled with one type of label and primers are labeled with another type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon then is thermally denatured to produce single stranded amplicon members. Upon formation of the single stranded amplicon members, the mixture is cooled to allow the formation of complexes between the probes and single stranded amplicon members.

As the single stranded amplicon sequences and probe sequences are cooled, the probe sequences preferentially bind the single stranded amplicon members. This finding is counterintuitive given that the probe sequences generally are selected to be shorter than the primer sequences and therefore have a lower melt temperature than the primers. Accordingly, the melt temperature of the amplicon produced by the primers should also have a higher melt temperature than the probes. Thus, as the mixture cools, the re-formation of the double stranded amplicon would be expected. As previously stated, however, this is not the case. The probes are found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate, which generally comprises a binding member attached to a directly detectable label. The conjugate becomes bound to the complexes and the conjugate's presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

Although the target sequence is described as single stranded, it also is contemplated to include the case where the target sequence is actually double stranded but is merely separated from its complement prior to hybridization with the amplification primer sequences. In the case where PCR is employed in this method, the ends of the target sequences are usually known. In cases where LCR or a modification thereof is employed in the preferred method, the entire target sequence is usually known. Typically, the target sequence is a nucleic acid sequence such as, for example, RNA or DNA.

The method provided herein can be used in well-known amplification reactions that include thermal cycle reaction mixtures, particularly in PCR and gap LCR (GLCR). Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated, they are separated from the target sequence, for example, by heating the reaction mixture to a "melt temperature" which is one in which complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filling the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the target's complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as, for example, deoxyadenine triphosphate, deoxyguanine triphosphate, deoxycytosine triphosphate and deoxythymine triphosphate.

While the amplification primers initiate amplification of the target sequence, the detection (or hybridization) probe is not involved in amplification. Detection probes are generally nucleic acid sequences or uncharged nucleic acid analogs such as, for example, peptide nucleic acids which are disclosed in International Publication No. WO 92/20702; morpholino analogs which are described in U.S. Pat. Nos 5,185,444, 5,034,506 and 5,142,047; and the like. Depending upon the type of label carried by the probe, the probe is employed to capture or detect the amplicon generated by the amplification reaction. The probe is not involved in amplification of the target sequence and therefore may have to be rendered "non-extendible" in that additional dNTPs cannot be added to the probe. In and of themselves, analogs usually are non-extendible and nucleic acid probes can be rendered non-extendible by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No. 07/049,061 filed Apr. 19, 1993 and incorporated herein by reference describes modifications which can be used to render a probe non-extendible.

The ratio of primers to probes is not important. Thus, either the probes or primers can be added to the reaction mixture in excess whereby the concentration of one would be greater than the concentration of the other. Alternatively, primers and probes can be employed in equivalent concentrations. Preferably, however, the primers are added to the reaction mixture in excess of the probes. Thus, primer to probe ratios of, for example, 5:1 and 20:1, are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), DuPont (Wilmington, Del.), or Milligen (Bedford Mass.). Many methods have been described for labeling oligonucleotides such as the primers or probes of the present invention. Enzo Biochemical (New York, N.Y.) and Clontech (Palo Alto, Calif.) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. Nos. 625,566, filed Dec. 11, 1990 and 630,908, filed Dec. 20, 1990, which are each incorporated herein by reference, teach methods for labeling probes at their 5' and 3' termini, respectively. International Publication Nos WO 92/10505, published Jun. 25, 1992, and WO 92/11388, published Jul. 9, 1992, teach methods for labeling probes at their 5' and 3' ends, respectively. According to one known method for labeling an oligonucleotide, a label-phosphoramidite reagent is prepared and used to add the label to the oligonucleotide during its synthesis. See, for example, N. T. Thuong et al., *Tet. Letters* 29(46):5905–5908 (1988); or J. S. Cohen et al., published U.S. patent application Ser. No. 07/246,688 (NTIS ORDER No. PAT-APPL-7-246,688) (1989). Preferably, probes are labeled at their 3' and 5' ends.

A capture label is attached to the primers or probes and can be a specific binding member which forms a binding pair with the solid phase reagent's specific binding member. It will be understood that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Generally, probe/single stranded amplicon member complexes can be detected using techniques commonly employed to perform heterogeneous immunoassays. Preferably, in this embodiment, detection is performed according to the protocols used by the commercially available Abbott LCx® instrumentation (Abbott Laboratories, Abbott Park, Ill.).

The primers and probes disclosed herein are useful in typical PCR assays, wherein the test sample is contacted with a pair of primers, amplification is performed, the hybridization probe is added, and detection is performed.

Another method provided by the present invention comprises contacting a test sample with a plurality of polynucleotides, wherein at least one polynucleotide is a PS108 molecule as described herein, hybridizing the test sample with the plurality of polynucleotides and detecting hybridization complexes. Hybridization complexes are identified and quantitated to compile a profile which is indicative of prostate tissue disease, such as prostate cancer. Expressed RNA sequences may further be detected by reverse transcription and amplification of the DNA product by procedures well-known in the art, including polymerase chain reaction (PCR).

Drug Screening and Gene Therapy.

The present invention also encompasses the use of gene therapy methods for the introduction of anti-sense PS108 derived molecules, such as polynucleotides or oligonucleotides of the present invention, into patients with conditions associated with abnormal expression of polynucleotides related to a prostate tissue disease or condition especially prostate cancer. These molecules, including antisense RNA and DNA fragments and ribozymes, are designed to inhibit the translation of PS108 mRNA, and may be used therapeutically in the treatment of conditions associated with altered or abnormal expression of PS108 polynucleotide.

Alternatively, the oligonucleotides described above can be delivered to cells by procedures known in the art such that the anti-sense RNA or DNA may be expressed in vivo to inhibit production of a PS108 polypeptide in the manner described above. Antisense constructs to a PS108 polynucleotide, therefore, reverse the action of PS108 transcripts and may be used for treating prostate tissue disease conditions, such as prostate cancer. These antisense constructs may also be used to treat tumor metastases.

The present invention also provides a method of screening a plurality of compounds for specific binding to PS108 polypeptide(s), or any fragment thereof, to identify at least one compound which specifically binds the PS108 polypeptide. Such a method comprises the steps of providing at least one compound; combining the PS108 polypeptide with each compound under suitable conditions for a time sufficient to allow binding; and detecting the PS108 polypeptide binding to each compound.

The polypeptide or peptide fragment employed in such a test may either be free in solution, affixed to a solid support, borne on a cell surface or located intracellularly. One method of screening utilizes eukaryotic or prokaryotic host cells which are stably transfected with recombinant nucleic acids which can express the polypeptide or peptide fragment. A drug, compound, or any other agent may be screened against such transfected cells in competitive binding assays. For example, the formation of complexes between a polypeptide and the agent being tested can be measured in either viable or fixed cells.

The present invention thus provides methods of screening for drugs, compounds, or any other agent which can be used to treat diseases associated with PS108. These methods comprise contacting the agent with a polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is used as a measure of the ability of the particular agent to bind to the polypeptide or to interfere with the polypeptide/cell complex.

The present invention also encompasses the use of competitive screening assays in which neutralizing antibodies capable of binding polypeptide specifically compete with a test agent for binding to the polypeptide or fragment thereof. In this manner, the antibodies can be used to detect the presence of any polypeptide in the test sample which shares one or more antigenic determinants with a PS108 polypeptide as provided herein.

Another technique for screening provides high throughput screening for compounds having suitable binding affinity to at least one polypeptide of PS108 disclosed herein. Briefly, large numbers of different small peptide test compounds are synthesized on a solid phase, such as plastic pins or some other surface. The peptide test compounds are reacted with polypeptide and washed. Polypeptide thus bound to the solid phase is detected by methods well-known in the art. Purified polypeptide can also be coated directly onto plates for use in the screening techniques described herein. In addition, non-neutralizing antibodies can be used to capture the polypeptide and immobilize it on the solid support. See, for example, EP 84/03564, published on Sep. 13, 1984, which is incorporated herein by reference.

The goal of rational drug design is to produce structural analogs of biologically active polypeptides of interest or of the small molecules including agonists, antagonists, or inhibitors with which they interact. Such structural analogs can be used to design drugs which are more active or stable forms of the polypeptide or which enhance or interfere with the function of a polypeptide in vivo. J. Hodgson, *Bio/Technology* 9:19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-like molecules or to identify efficient inhibitors Useful examples of rational drug design may include molecules which have improved activity or stability as shown by S. Braxton et al., *Biochemistry* 31:7796–7801 (1992), or which act as inhibitors, agonists, or antagonists of native peptides as shown by S. B. P. Athauda et al., *J Biochem.* (*Tokyo*) 113 (6):742–746 (1993), incorporated herein by reference.

It also is possible to isolate a target-specific antibody selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then can be used to identify and isolate peptides from banks of chemically or biologically produced peptides. The isolated peptides then can act as the pharmacophore (that is, a prototype pharmaceutical drug).

A sufficient amount of a recombinant polypeptide of the present invention may be made available to perform analytical studies such as X-ray crystallography. In addition, knowledge of the polypeptide amino acid sequence which is derivable from the nucleic acid sequence provided herein will provide guidance to those employing computer modeling techniques in place of, or in addition to, x-ray crystallography.

Antibodies specific to a PS108 polypeptide (e.g., anti-PS108 antibodies) further may be used to inhibit the biological action of the polypeptide by binding to the polypeptide. In this manner, the antibodies may be used in therapy, for example, to treat prostate tissue diseases including prostate cancer and its metastases.

Further, such antibodies can detect the presence or absence of a PS108 polypeptide in a test sample and, therefore, are useful as diagnostic markers for the diagnosis of a prostate tissue disease or condition especially prostate cancer. Such antibodies may also function as a diagnostic marker for prostate tissue disease conditions, such as prostate cancer.

The present invention also is directed to antagonists and inhibitors of the polypeptides of the present invention. The antagonists and inhibitors are those which inhibit or eliminate the function of the polypeptide. Thus, for example, an antagonist may bind to a polypeptide of the present invention and inhibit or eliminate its function. The antagonist, for example, could be an antibody against the polypeptide which eliminates the activity of a PS108 polypeptide by binding a PS108 polypeptide, or in some cases the antagonist may be an oligonucleotide. Examples of small molecule inhibitors include, but are not limited to, small peptides or peptide-like molecules.

The antagonists and inhibitors may be employed as a composition with a pharmaceutically acceptable carrier including, but not limited to, saline, buffered saline, dextrose, water, glycerol, ethanol and combinations thereof. Administration of PS108 polypeptide inhibitors is preferably systemic. The present invention also provides an antibody which inhibits the action of such a polypeptide.

Antisense technology can be used to reduce gene expression through triple-helix formation or antisense DNA or RNA, both of which methods are based on binding of a polynucleotide to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription, thereby preventing transcription and the production of the PS108 polypeptide. For triple helix, see, for example, Lee et al, *Nuc. Acids Res.* 6:3073 (1979); Cooney et al, *Science* 241:456 (1988); and Dervan et al, *Science* 251:1360 (1991) The antisense RNA oligonucleotide hybridizes to the mRNA in vivo and blocks translation of a mRNA molecule into the PS108 polypeptide. For antisense, see, for example, Okano, *J. Neurochem.* 56:560 (1991); and "Oligodeoxynucleotides as Antisense Inhibitors of Gene Expression," CRC Press, Boca Raton, Fla. (1988). Antisense oligonucleotides act with greater efficacy when modified to contain artificial internucleotide linkages which render the molecule resistant to nucleolytic cleavage. Such artificial internucleotide linkages include, but are not limited to, methylphosphonate, phosphorothiolate and phosphoroamydate internucleotide linkages.

Recombinant Technology.

The present invention provides host cells and expression vectors comprising PS108 polynucleotides of the present invention and methods for the production of the polypeptide(s) they encode. Such methods comprise culturing the host cells under conditions suitable for the expression of the PS108 polynucleotide and recovering the PS108 polypeptide from the cell culture.

The present invention also provides vectors which include PS108 polynucleotides of the present invention, host cells which are genetically engineered with vectors of the present invention and the production of polypeptides of the present invention by recombinant techniques.

Host cells are genetically engineered (transfected, transduced or transformed) with the vectors of this invention which may be cloning vectors or expression vectors. The vector may be in the form of a plasmid, a viral particle, a phage, etc. The engineered host cells can be cultured in conventional nutrient media modified as appropriate for activating promoters, selecting transfected cells, or amplifying PS108 gene(s). The culture conditions, such as temperature, pH and the like, are those previously used with the host cell selected for expression, and will be apparent to the ordinarily skilled artisan.

The polynucleotides of the present invention may be employed for producing a polypeptide by recombinant techniques. Thus, the polynucleotide sequence may be included in any one of a variety of expression vehicles, in particular, vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include, but are not limited to, the LTR or the SV40 promoter, the *E. coli* lac or trp, the phage lambda P sub L promoter and other promoters known to control expression of genes in prokaryotic or eukaryotic cells or their viruses. The expression vector also contains a ribosome binding site for translation initiation and transcription terminator. The vector may also include appropriate sequences for amplifying expression. In addition, the expression vectors preferably contain a gene to provide a phenotypic trait for selection of transfected host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transfect an appropriate host to permit the host to express the protein. As representative examples of appropriate hosts, there may be mentioned: bacterial cells, such as *E. coli, Salmonella typhimurium;* Streptomyces sp.; fungal cells, such as yeast; insect cells, such as Drosophila and Sf9; animal cells, such as CHO, COS or Bowes melanoma; plant cells, etc. The selection of an appropriate host is deemed to be within the scope of those skilled in the art from the teachings provided herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences including, for example, a promoter, operably linked to the sequence. Large numbers of suitable vectors and promoters are known to those of skill in the art and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia); Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Plasmid pINCY is generally identical to the plasmid pSPORT1 (available from Life Technologies, Gaithersburg, Md.) with the exception that it has two modifications in the polylinker (multiple cloning site). These modifications are (1) it lacks a HindIII restriction site and (2) its EcoRI restriction site lies at a different location. pINCY is created from pSPORT1 by cleaving pSPORT1 with both HindIII and EcoRI and replacing the excised fragment of the polylinker with synthetic DNA fragments (SEQUENCE ID NO 17 and SEQUENCE ID NO 18). This replacement may be made in any manner known to those of ordinary skill in the art. For example, the two nucleotide sequences, SEQUENCE ID NO 17 and SEQUENCE ID NO 18, may be generated synthetically with 5' terminal phosphates, mixed together, and then ligated under standard conditions for performing staggered end ligations into the pSPORT1 plasmid cut with HindIII and EcoRI. Suitable host cells (such as *E. coli* DH5$\mu$ cells) then are transfected with the ligated DNA and recombinant clones are selected for ampicillin resistance. Plasmid DNA then is prepared from individual clones and subjected to restriction enzyme analysis or DNA sequencing in order to confirm the presence of insert sequences in the proper orientation. Other cloning strategies known to the ordinary artisan also may be employed.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retroviruses and mouse metallothionein-I. Selection of the appropriate vector and promoter is well within the level of ordinary skill in the art.

In a further embodiment, the present invention provides host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (L. Davis et al., "Basic Methods in Molecular Biology," 2nd edition, Appleton and Lang, Paramount Publishing, East Norwalk, Conn. (1994)).

The constructs in host cells can be used in a conventional manner to produce the gene product encoded by the recombinant sequence. Alternatively, the polypeptides of the invention can be synthetically produced by conventional peptide synthesizers.

Recombinant proteins can be expressed in mammalian cells, yeast, bacteria, or other cells, under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual,* Second Edition, (Cold Spring Harbor, N.Y., 1989), which is hereby incorporated by reference.

Transcription of a DNA encoding the polypeptide(s) of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin and adenovirus enhancers.

Generally, recombinant expression vectors will include origins of replication and selectable markers permitting transfection of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transfection include *E. coli, Bacillus subtilis, Salmonella typhimurium* and various species within the genera Pseudomonas, Streptomyces and Staphylococcus, although others may also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transfection of a suitable host and growth of the host to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method including freeze-thaw cycling, sonication, mechanical disruption, or use of cell lysing agents. Such methods are well-known to the ordinary artisan.

Various mammalian cell culture systems can also be employed to express recombinant protein. Examples of mammalian expression systems include the COS-7 lines of monkey kidney fibroblasts described by Gluzman, *Cell* 23:175 (1981), and other cell lines capable of expressing a compatible vector, such as the C 127, HEK-293, 3T3, CHO, HeLa and BHK cell lines. Mammalian expression vectors will comprise an origin of replication, a suitable promoter and enhancer and also any necessary ribosome binding sites, polyadenylation sites, splice donor and acceptor sites, transcriptional termination sequences and 5' flanking nontranscribed sequences. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

PS108 polypeptides are recovered and purified from recombinant cell cultures by known methods including affinity chromatography, ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification (Price, et al., *J. Biol. Chem.* 244:917 (1969)). Protein refolding steps can be used, as necessary, in completing configuration of the polypeptide. Finally, high performance liquid chromatography (HPLC) can be employed for final purification steps.

Thus, polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue.

The starting plasmids can be constructed from available plasmids in accord with published, known procedures. In addition, equivalent plasmids to those described are known in the art and will be apparent to one of ordinary skill in the art.

The following is the general procedure for the isolation and analysis of cDNA clones. In a particular embodiment disclosed herein, mRNA was isolated from prostate tissue and used to generate the cDNA library. Prostate tissue was obtained from patients by surgical resection and was classified as tumor or non-tumor tissue by a pathologist.

The cDNA inserts from random isolates of the prostate tissue libraries were sequenced in part, analyzed in detail as set forth in the Examples, and are disclosed in the Sequence Listing as SEQUENCE ID NOS 1–14. Also analyzed in detail as set forth in the Examples, and disclosed in the Sequence Listing, is the full-length sequence of clone 1711346 (referred to as clone 1711346IH, (SEQUENCE ID NO 15)). The consensus sequence of these inserts is presented as SEQUENCE ID NO 16. These polynucleotides may contain an entire open reading frame with or without associated regulatory sequences for a particular gene, or they may encode only a portion of the gene of interest. This is attributed to the fact that many genes are several hundred and sometimes several thousand bases in length and, with current technology, cannot be cloned in their entirety because of vector limitations, incomplete reverse transcription of the first strand, or incomplete replication of the second strand. Contiguous, secondary clones containing additional nucleotide sequences may be obtained using a variety of methods known to those of skill in the art.

Methods for DNA sequencing are well known in the art. Conventional enzymatic methods employ DNA polymerase, Klenow fragment, Sequenase (US Biochemical Corp, Cleveland, Ohio) or Taq polymerase to extend DNA chains from an oligonucleotide primer annealed to the DNA template of interest. Methods have been developed for the use of both single-stranded and double-stranded templates. The chain termination reaction products may be electrophoresed on urea/polyacrylamide gels and detected either by autoradiography (for radionucleotide labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Applied Biosystems 377 DNA Sequencers (Applied Biosystems, Foster City, Calif.).

The reading frame of the nucleotide sequence can be ascertained by several types of analyses. First, reading frames contained within the coding sequence can be analyzed for the presence of start codon ATG and stop codons TGA, TAA or TAG. Typically, one reading frame will continue throughout the major portion of a cDNA sequence while other reading frames tend to contain numerous stop codons. In such cases, reading frame determination is straightforward. In other more difficult cases, further analysis is required.

Algorithms have been created to analyze the occurrence of individual nucleotide bases at each putative codon triplet. See, for example J. W. Fickett, Nuc. Acids Res. 10:5303 (1982). Coding DNA for particular organisms (bacteria, plants and animals) tends to contain certain nucleotides within certain triplet periodicities, such as a significant preference for pyrimidines in the third codon position. These preferences have been incorporated into widely available software which can be used to determine coding potential (and frame) of a given stretch of DNA. The algorithm-derived information combined with start/stop codon information can be used to determine proper frame with a high degree of certainty. This, in turn, readily permits cloning of the sequence in the correct reading frame into appropriate expression vectors.

The nucleic acid sequences disclosed herein may be joined to a variety of other polynucleotide sequences and vectors of interest by means of well-established recombinant DNA techniques. See J. Sambrook et al., supra. Vectors of interest include cloning vectors, such as plasmids, cosmids, phage derivatives, phagemids, as well as sequencing, replication and expression vectors, and the like. In general, such vectors contain an origin of replication functional in at least one organism, convenient restriction endonuclease digestion sites and selectable markers appropriate for particular host cells. The vectors can be transferred by a variety of means known to those of skill in the art into suitable host cells which then produce the desired DNA, RNA or polypeptides.

Occasionally, sequencing or random reverse transcription errors will mask the presence of the appropriate open reading frame or regulatory element. In such cases, it is possible to determine the correct reading frame by attempting to express the polypeptide and determining the amino acid sequence by standard peptide mapping and sequencing techniques. See, F. M. Ausubel et al., Current Protocols in Molecular Biology, John Wiley & Sons, New York, N.Y. (1989). Additionally, the actual reading frame of a given nucleotide sequence may be determined by transfection of host cells with vectors containing all three potential reading frames. Only those cells with the nucleotide sequence in the correct reading frame will produce a peptide of the predicted length.

The nucleotide sequences provided herein have been prepared by current, state-of-the-art, automated methods and, as such, may contain unidentified nucleotides. These will not present a problem to those skilled in the art who wish to practice the invention. Several methods employing standard recombinant techniques, described in J. Sambrook (supra) or periodic updates thereof, may be used to complete the missing sequence information. The same techniques used for obtaining a full length sequence, as described herein, may be used to obtain nucleotide sequences.

Expression of a particular cDNA may be accomplished by subcloning the cDNA into an appropriate expression vector and transfecting this vector into an appropriate expression host. The cloning vector used for the generation of the prostate tissue cDNA library can be used for transcribing mRNA of a particular cDNA and contains a promoter for beta-galactosidase, an amino-terminal met and the subsequent seven amino acid residues of beta-galactosidase. Immediately following these eight residues is an engineered bacteriophage promoter useful for artificial priming and transcription, as well as a number of unique restriction sites, including EcoRI, for cloning. The vector can be transfected into an appropriate host strain of E. coli.

Induction of the isolated bacterial strain with isopropylthiogalactoside (IPTG) using standard methods will produce a fusion protein which contains the first seven residues of beta-galactosidase, about 15 residues of linker and the peptide encoded within the cDNA. Since cDNA clone inserts are generated by an essentially random process, there is one chance in three that the included cDNA will lie in the correct frame for proper translation. If the cDNA is not in the proper reading frame, the correct frame can be obtained by deletion or insertion of an appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide primers containing cloning sites and segments of DNA sufficient to hybridize to stretches at both ends of the target cDNA can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include, but are not limited to, mammalian cells, such as Chinese Hamster Ovary (CHO) and human embryonic kidney (HEK) 293 cells, insect cells, such as Sf9 cells, yeast cells, such as *Saccharomyces cerevisiae* and bacteria, such as *E. coli*. For each of these cell systems, a useful expression vector may also include an origin of replication to allow propagation in bacteria and a selectable marker such as the beta-lactamase antibiotic resistance gene to allow selection in bacteria. In addition, the vectors may include a second selectable marker, such as the neomycin phosphotransferase gene, to allow selection in transfected eukaryotic host cells. Vectors for use in eukaryotic expression hosts may require the addition of 3' poly A tail if the sequence of interest lacks poly A.

Additionally, the vector may contain promoters or enhancers which increase gene expression. Such promoters are host specific and include, but are not limited to, MMTV, SV40, or metallothionine promoters for CHO cells; trp, lac, tac or T7 promoters for bacterial hosts; or alpha factor, alcohol oxidase or PGH promoters for yeast. Adenoviral vectors with or without transcription enhancers, such as the Rous sarcoma virus (RSV) enhancer, may be used to drive protein expression in mammalian cell lines. Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transfection of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

Immunoassays.

PS108 polypeptides, including fragments, derivatives, and analogs thereof, or cells expressing such polypeptides, can be utilized in a variety of assays, many of which are described herein, for the detection of antibodies to prostate tissue. They also can be used as immunogens to produce antibodies. These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

For example, antibodies generated against a polypeptide comprising a sequence of the present invention can be obtained by direct injection of the polypeptide into an animal or by administering the polypeptide to an animal such as a mouse, rabbit, goat or human. A mouse, rabbit or goat is preferred. The polypeptide is selected from the group consisting of SEQUENCE ID NO 36, SEQUENCE ID NO 37, SEQUENCE ID NO 38, SEQUENCE ID NO 39, and fragments thereof. The antibody so obtained then will bind the polypeptide itself. In this manner, even a sequence encoding only a fragment of the polypeptide can be used to generate antibodies that bind the native polypeptide. Such antibodies then can be used to isolate the polypeptide from test samples such as tissue suspected of containing that polypeptide. For preparation of monoclonal antibodies, any technique which provides antibodies produced by continuous cell line cultures can be used. Examples include the hybridoma technique as described by Kohler and Milstein, *Nature* 256:495–497 (1975), the trioma technique, the human B-cell hybridoma technique as described by Kozbor et al, *Immun. Today* 4:72 (1983) and the EBV-hybridoma technique to produce human monoclonal antibodies as described by Cole et al., in *Monoclonal Antibodies and Cancer Therapy*, Alan R. Liss, Inc, New York, N.Y., pp. 77–96 (1985). Techniques described for the production of single chain antibodies can be adapted to produce single chain antibodies to immunogenic polypeptide products of this invention. See, for example, U.S. Pat. No. 4,946,778, which is incorporated herein by reference.

Various assay formats may utilize the antibodies of the present invention, including "sandwich" immunoassays and probe assays. For example, the antibodies of the present invention, or fragments thereof, can be employed in various assay systems to determine the presence, if any, of PS108 antigen in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of PS108 antigen in the test sample and captured on the solid phase, if any, is determined by detecting the measurable signal generated by the signal generating compound. The amount of PS108 antigen present in the test sample is proportional to the signal generated.

In an alternative assay format, a mixture is formed by contacting: (1) a polyclonal antibody, monoclonal antibody, or fragment thereof, which specifically binds to PS108 antigen, or a combination of such antibodies bound to a solid support; (2) the test sample; and (3) an indicator reagent comprising a monoclonal antibody, polyclonal antibody, or fragment thereof, which specifically binds to a different PS108 antigen (or a combination of these antibodies) to which a signal generating compound is attached. This mixture is incubated for a time and under conditions sufficient to form antibody/antigen/antibody complexes. The presence, if any, of PS108 antigen present in the test sample and captured on the solid phase is determined by detecting the measurable signal generated by the signal generating compound. The amount of PS108 antigen present in the test sample is proportional to the signal generated.

In another assay format, one or a combination of at least two monoclonal antibodies of the invention can be employed as a competitive probe for the detection of antibodies to PS108 antigen. For example, PS108 polypeptides such as the recombinant antigens disclosed herein, either alone or in combination, are coated on a solid phase. A test sample suspected of containing antibody to PS108 antigen then is incubated with an indicator reagent comprising a signal generating compound and at least one monoclonal antibody of the invention for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, each of the monoclonal or polyclonal antibodies of the present invention can be employed in the detection of PS108 antigens in tissue sections, as well as in cells, by immunohistochemical analysis. The tissue sections can be cut from either frozen or chemically fixed samples of tissue. If the antigens are to be detected in cells, the cells can be isolated from blood, urine, breast aspirates, or other bodily fluids. The cells may be obtained by biopsy, either surgical or by needle. The cells can be isolated by centrifugation or magnetic attraction after labeling with magnetic particles or ferrofluids so as to enrich a particular fraction of cells for staining with the antibodies of the present invention. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific PS108 polypeptides from cell cultures or biological tissues such as to purify recombinant and native PS108 proteins.

The monoclonal antibodies of the invention also can be used for the generation of chimeric antibodies for therapeutic use, or other similar applications.

The monoclonal antibodies or fragments thereof can be provided individually to detect PS108 antigens. Combinations of the monoclonal antibodies (and fragments thereof) provided herein also may be used together as components in a mixture or "cocktail" of at least one PS108 antibody of the invention, along with antibodies which specifically bind to other PS108 regions, each antibody having different binding specificities. Thus, this cocktail can include the monoclonal antibodies of the invention which are directed to PS108 polypeptides disclosed herein and other monoclonal antibodies specific to other antigenic determinants of PS108 antigens or other related proteins.

The polyclonal antibody or fragment thereof which can be used in the assay formats should specifically bind to a PS108 polypeptide or other PS108 polypeptides additionally used in the assay. The polyclonal antibody used preferably is of mammalian origin such as, human, goat, rabbit or sheep polyclonal antibody which binds PS108 polypeptide. Most preferably, the polyclonal antibody is of rabbit origin. The polyclonal antibodies used in the assays can be used either alone or as a cocktail of polyclonal antibodies. Since the cocktails used in the assay formats are comprised of either monoclonal antibodies or polyclonal antibodies having different binding specificity to PS108 polypeptides, they are useful for the detecting, diagnosing, staging, monitoring, prognosticating, in vivo imaging, preventing or treating, or determining the predisposition to, diseases and conditions of the prostate, such as prostate cancer.

It is contemplated and within the scope of the present invention that PS108 antigen may be detectable in assays by use of a recombinant antigen as well as by use of a synthetic peptide or purified peptide, which peptide comprises an amino acid sequence of PS108. The amino acid sequence of such a polypeptide is selected from the group consisting of SEQUENCE ID NO 36, SEQUENCE ID NO 37, SEQUENCE ID NO 38, SEQUENCE ID NO 39, and fragments thereof. It also is within the scope of the present invention that different synthetic, recombinant or purified peptides, identifying different epitopes of PS108, can be used in combination in an assay for the detecting, diagnosing, staging, monitoring, prognosticating, in vivo imaging, preventing or treating, or determining the predisposition to diseases and conditions of the prostate, such as prostate cancer. In this case, all of these peptides can be coated onto one solid phase; or each separate peptide may be coated onto separate solid phases, such as microparticles, and then combined to form a mixture of peptides which can be later used in assays. Furthermore, it is contemplated that multiple peptides which define epitopes from different antigens may be used for the detection, diagnosis, staging, monitoring, prognosis, prevention or treatment of, or determining the predisposition to, diseases and conditions of the prostate, such as prostate cancer. Peptides coated on solid phases or labeled with detectable labels are then allowed to compete with those present in a patient sample (if any) for a limited amount of antibody. A reduction in binding of the synthetic, recombinant, or purified peptides to the antibody (or antibodies) is an indication of the presence of PS108 antigen in the patient sample. The presence of PS108 antigen indicates the presence of prostate tissue disease, especially prostate cancer, in the patient. Variations of assay formats are known to those of ordinary skill in the art and many are discussed herein below.

In another assay format, the presence of anti-PS108 antibody and/or PS108 antigen can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens derived from the expression systems disclosed herein may be utilized, as well as monoclonal antibodies produced from the proteins derived from the expression systems as disclosed herein. For example, in this assay system, PS108 antigen can be the first analyte. Such assay systems are described in greater detail in EP Publication No. 0473065.

In yet other assay formats, the polypeptides disclosed herein may be utilized to detect the presence of antibody against PS108 antigen in test samples. For example, a test sample is incubated with a solid phase to which at least one polypeptide such as a recombinant protein or synthetic peptide has been attached. The polypeptide is selected from the group consisting of SEQUENCE ID NO 36, SEQUENCE ID NO 37, SEQUENCE ID NO 38, SEQUENCE ID NO 39, and fragments thereof. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached, and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of antibody against PS108 antigen. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as E. coli is used as a capture antigen on a solid phase, a test sample is added to the so-prepared solid phase, and following standard incubation and washing steps as deemed or required, a recombinant protein derived from a different source (i.e., non-E. coli) is utilized as a part of an indicator reagent which subsequently is detected. Likewise, combinations of a recombinant antigen on a solid phase and synthetic peptide in the indicator phase also are possible. Any assay format which utilizes an antigen specific for PS108 produced or derived from a first source as the capture antigen and an antigen specific for PS108 from a different second source is contemplated. Thus, various combinations of recombinant antigens, as well as the use of synthetic peptides, purified proteins and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication 0326100 and EP publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in EPO Publication No. 0 273,115.

Also, the methods of the present invention can be adapted for use in systems which utilize microparticle technology including automated and semi-automated systems wherein the solid phase comprises a microparticle (magnetic or non-magnetic). Such systems include those described in, for example, published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, particularly in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

It is contemplated that the reagent employed for the assay can be provided in the form of a test kit with one or more containers such as vials or bottles, with each container containing a separate reagent such as a probe, primer, monoclonal antibody or a cocktail of monoclonal antibodies, or a polypeptide (e.g. recombinantly, synthetically produced or purified) employed in the assay. The polypeptide is selected from the group consisting of SEQUENCE ID NO 36, SEQUENCE ID NO 37, SEQUENCE ID NO 38, SEQUENCE ID NO 39, and fragments thereof. Other components such as buffers, controls and the like, known to those of ordinary skill in art, may be included in such test kits. It also is contemplated to provide test kits which have means for collecting test samples comprising accessible body fluids, e.g., blood, urine, saliva and stool. Such tools useful for collection ("collection materials") include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens. Test kits designed for the collection, stabilization and preservation of test specimens obtained by surgery or needle biopsy are also useful. It is contemplated that all kits may be configured in two components which can be provided separately; one component for collection and transport of the specimen and the other component for the analysis of the specimen. The collection component, for example, can be provided to the open market user while the components for analysis can be provided to others such as laboratory personnel for determination of the presence, absence or amount of analyte. Further, kits for the collection, stabilization and preservation of test specimens may be configured for use by untrained personnel and may be available in the open market for use at home with subsequent transportation to a laboratory for analysis of the test sample.

In Vivo Antibody Use.

Antibodies of the present invention can be used in vivo; that is, they can be injected into patients suspected of having or having diseases of the prostate for diagnostic or therapeutic uses. The use of antibodies for in vivo diagnosis is well known in the art. Sumerdon et al, Nucl. Med. Biol, 17, 247–254 (1990) have described an optimized antibody-chelator for the radioimmunoscintographic imaging of carcinoembryonic antigen (CEA) expressing tumors using Indium-111 as the label. Griffin et al, J Clin Onc, 9, 631–640 (1991) have described the use of this agent in detecting tumors in patients suspected of having recurrent colorectal cancer. The use of similar agents with paramagnetic ions as labels for magnetic resonance imaging is know in the art (R. B. Lauffer, Magnetic Resonance in Medicine, 22, 339–342 (1991). It is anticipated that antibodies directed against PS108 antigen can be injected into patients suspected of having a disease of the prostate such as prostate cancer for the purpose of diagnosing or staging the disease status of the patient. The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used. Localization of the label within the prostate or external to the prostate may allow determination of spread of the disease. The amount of label within the prostate may allow determination of the presence or absence of cancer of the prostate.

For patients known to have a disease of the prostate, injection of an antibody directed against PS108 antigen may halve therapeutic benefit. The antibody may exert its effect without the use of attached agents by binding to PS108 antigen expressed on or in the tissue or organ. Alternatively, the antibody may be conjugated to cytotoxic agents such as drugs, toxins, or radionuclides to enhance its therapeutic effect. Garnett and Baldwin, Cancer Research, 46, 2407–2412 (1986) have described the preparation of a drug-monoclonal antibody conjugate. Pastan et al, Cell, 47, 641–648 (1986) have reviewed the use of toxins conjugated to monoclonal antibodies for the therapy of various cancers. Goodwin and Meares, Cancer Supplement, 80, 2675–2680 (1997) have described the use of Yttrium-90 labeled monoclonal antibodies in various strategies to maximize the dose to tumor while limiting normal tissue toxicity. Other known cytotoxic radionuclides include Copper-67, Iodine-131, and Rhenium-186 all of which can be used to label monoclonal antibodies directed against PS108 antigen for the treatment of cancer of the prostate.

E. coli bacteria (clone 1711346) was deposited on Jan. 14, 1997 with the American Type Culture Collection (A.T.C.C.), 12301 Parklawn Drive, Rockville, Md. 20852. The deposit was made under the terms of the Budapest Treaty and will be maintained for a period of thirty (30) years from the date of deposit, or for five (5) years after the last request for the deposit, or for the enforceable period of the U.S. patent, whichever is longer. The deposit and any other deposited material described herein are provided for convenience only, and are not required to practice the present invention in view of the teachings provided herein. The cDNA sequence in all of the deposited material is incorporated herein by reference. Clone 1711346 was accorded A.T.C.C. Deposit No. 98276.

The present invention will now be described by way of examples, which are meant to illustrate, but not to limit, the scope of the present invention.

EXAMPLES

Example 1

Identification of Prostate Tissue Library PS108 Gene-Specific Clones

A. Library Comparison of Expressed Sequence Tags (EST's) or Transcript Images. Partial sequences of cDNA clone inserts, so-called "expressed sequence tags" (EST's), were derived from cDNA libraries made from prostate tumor tissues, prostate non-tumor tissues and numerous other tissues (both tumorous and non-tumorous) and entered into a database (LIFESEQ™ database, available from Incyte Pharmaceuticals, Palo Alto, Calif.) as gene transcript images. See International Publication No. WO 95/20681. (A transcript image is a listing of the number of EST's for each of the represented genes in a given tissue library. EST's sharing regions of mutual sequence overlap are classified into clusters. A cluster is assigned a clone number from a representative 5' EST. Often, a cluster of interest can be extended by comparing its consensus sequence with sequences of other EST's which did not meet the criteria for automated clustering. The alignment of all available clusters and single EST's represent a contig from which a consensus sequence is derived.) The transcript images then were evaluated to identify EST sequences that were representative primarily of the prostate tissue libraries. These target clones then were ranked according to their abundance (occurrence) in the target libraries and their absence from background libraries. Higher abundance clones with low background occurrence were given higher study priority. EST's corresponding to the consensus sequence of PS108 were found in 82.3% (28 of 34) of prostate tissue libraries. EST's corresponding to the consensus sequence SEQUENCE ID NO 16 (or fragments thereof) were found in 3.4% (21 of 618) of the other, non-prostate, libraries of the data base. Therefore, the consensus sequence or fragment thereof was found more than 24 times more often in prostate than non-prostate tissues. Overlapping clones 1864683 (SEQUENCE ID NO 1), 1711346 (SEQUENCE ID NO 2), 1913982 (SEQUENCE ID NO 3), 825779 (SEQUENCE ID NO 4), 2626650 (SEQUENCE ID NO 5), 1808389 (SEQUENCE ID NO 6), 1651121 (SEQUENCE ID NO 7), 3520833

(SEQUENCE ID NO 8), 2188949 (SEQUENCE ID NO 9), 3497504 (SEQUENCE ID NO 10), 3964174 (SEQUENCE ID NO 11), 3705332 (SEQUENCE ID NO 12), 2270646 (SEQUENCE ID NO 13), and 1810610 (SEQUENCE ID NO 14) were identified for further study. These represented the minimum number of clones that were needed to form the contig and from which, along with the full-length sequence of clone 1711346IH (SEQUENCE ID NO 15), the consensus sequence provided herein (SEQUENCE ID NO 16) was derived.

B. Generation of a Consensus Sequence. The nucleotide sequences of clones 1864683 (SEQUENCE ID NO 1), 1711346 (SEQUENCE ID NO 2), 1913982 (SEQUENCE ID NO 3), 825779 (SEQUENCE ID NO 4), 2626650 (SEQUENCE ID NO 5), 1808389 (SEQUENCE ID NO 6), 1651121 (SEQUENCE ID NO 7), 3520833 (SEQUENCE ID NO 8), 2188949 (SEQUENCE ID NO 9), 3497504 (SEQUENCE ID NO 10), 3964174 (SEQUENCE ID NO 11), 3705332 (SEQUENCE ID NO 12), 2270646 (SEQUENCE ID NO 13), 1810610 (SEQUENCE ID NO 14), and 1711346IH (SEQUENCE ID NO 15), were entered in the Sequencher™ Program (available from Gene Codes Corporation, Ann Arbor, Mich.) in order to generate a nucleotide alignment (contig map) and then generate their consensus sequence (SEQUENCE ID NO 16). FIGS. 1A–1E show the nucleotide sequence alignment of these clones and their resultant nucleotide consensus sequence (SEQUENCE ID NO 16). FIG. 2 presents the contig map depicting the clones 1864683 (SEQUENCE ID NO 1), 1711346 (SEQUENCE ID NO 2), 1913982 (SEQUENCE ID NO 3), 825779 (SEQUENCE ID NO 4), 2626650 (SEQUENCE ID NO 5), 1808389 (SEQUENCE ID NO 6),1651121 (SEQUENCE ID NO 7), 3520833 (SEQUENCE ID NO 8), 2188949 (SEQUENCE ID NO 9), 3497504 (SEQUENCE ID NO 10), 3964174 (SEQUENCE ID NO 11), 3705332 (SEQUENCE ID NO 12), 2270646 (SEQUENCE ID NO 13), 1810610 (SEQUENCE ID NO 14) and 1711346IH (SEQUENCE ID NO 15) which form overlapping regions of the PS108 gene, and the resultant consensus nucleotide sequence (SEQUENCE ID NO 16) of these clones in a graphic display. Following this, a three-frame translation was performed on the consensus sequence (SEQUENCE ID NO 16). The first forward frame was found to have an open reading frame encoding a 255 residue amino acid sequence which is presented as SEQUENCE ID NO 36.

Analysis of the LIFESEQ™ database indicates a possible C/T polymorphism at position 823 in the consensus nucleotide sequence (SEQUENCE ID NO 16). There were ten occurrences of the C nucleotide variant and three occurrences of the T nucleotide variant in the database. The site of the potential polymorphism is in the 3' untranslated region of the gene and does not affect the amino acid composition of the protein product.

Example 2

Sequencing of PS108 EST-Specific Clones

The full-length DNA sequence of clone 1711346IH of the PS108 gene contig was determined (SEQUENCE ID NO 15) using dideoxy termination sequencing with dye terminators following known methods (F. Sanger et al., *PNAS U.S.A.* 74:5463 (1977).

Because the pINCY vector (available from Incyte Pharmaceuticals, Inc., Palo Alto, Calif.) contains universal priming sites just adjacent to the 3' and 5' ligation junctions of the inserts, approximately 300 bases of the insert were sequenced in both directions using two universal primers (SEQUENCE ID NO 19 and SEQUENCE ID NO 20, available from New England Biolabs, Beverly, Mass., and Applied Biosystems Inc, Foster City, Calif., respectively). The sequencing reactions were run on a polyacrylamide denaturing gel, and the sequences were determined by an Applied Biosystems 377 Sequencer (available from Applied Biosystems, Foster City, Calif.). Additional sequencing primers (SEQUENCE ID NOS 21–33) were designed from sequence information of the consensus sequence (SEQUENCE ID NO 16). These primers then were used to determine the remaining DNA sequence of the cloned insert from each DNA strand, as previously described.

Example 3

Nucleic Acid

A. RNA Extraction from Tissue. Total RNA was isolated from prostate tissues and from non-prostate tissues. Various methods were utilized, including, but not limited to, the lithium chloride/urea technique, known in the art and described by Kato et al. (*J. Virol.* 61:2182–2191, 1987), and TRIzol™ (Gibco-BRL, Grand Island, N.Y.).

Briefly, tissue was placed in a sterile conical tube on ice, and 10–15 volumes of 3 M LiCl, 6 M urea, 5 mM EDTA, 0.1 M β-mercaptoethanol, 50 mM Tris-HCl (pH 7.5) were added. The tissue was homogenized with a Polytron® homogenizer (Brinkman Instruments, Inc., Westbury, N.Y.) for 30–50 sec on ice. The solution was transferred to a 15 ml plastic centrifuge tube and placed overnight at −20° C. The tube was centrifuged for 90 min at 9,000×g at 0–4° C. and the supernatant was immediately decanted. Ten ml of 3 M LiCl were added and the tube was vortexed for 5 sec. The tube was centrifuged for 45 min at 11,000×g at 0–4° C. The decanting, resuspension in LiCl, and centrifugation was repeated and the final pellet was air dried and suspended in 2 ml of 1 mM EDTA, 0.5% SDS, 10 mM Tris (pH 7.5). Twenty microliters (20 μl) of Proteinase K (20 mg/ml) were added, and the solution was incubated for 30 min at 37° C. with occasional mixing. One-tenth volume (0.22–0.25 ml) of 3 M NaCl was added, and the solution was vortexed before transfer into another tube containing 2 ml of phenol/chloroform/isoamyl alcohol (PCI). The tube was vortexed for 1–3 sec and centrifuged for 20 min at 3,000×g at 10° C. The PCI extraction was repeated and followed by two similar extractions with chloroform/isoamyl alcohol (CI). The final aqueous solution was transferred to a prechilled 15 ml Corex glass tube containing 6 ml of absolute ethanol, the tube was covered with parafilm, and placed at −20° C. overnight. The tube was centrifuged for 30 min at 10,000×g at 0–4° C. and the ethanol supernatant was decanted immediately. The RNA pellet was washed four times with 10 ml of 75% ice-cold ethanol and the final pellet was air dried for 15 min at room temperature. The RNA was suspended in 0.5 ml of 10 mM TE (pH 7.6, 1 mM EDTA) and its concentration was determined spectrophotometrically. RNA samples were aliquoted and stored at −70° C. as ethanol precipitates.

The quality of the RNA was determined by agarose gel electrophoresis (see Example 5, Northern Blot Analysis) and staining with 0.5 μg/ml ethidium bromide for one hour. RNA samples that did not contain intact rRNAs were excluded from the study.

Alternatively, for RT-PCR analysis, 1 ml of Ultraspec RNA reagent was added to 120 mg of pulverized tissue in a 2.0 ml polypropylene microfuge tube, homogenized with a Polytron® homogenizer (Brinkman Instruments, Inc., Westbury, N.Y.) for 50 sec and placed on ice for 5 min. Then, 0.2 ml of chloroform was added to each sample, followed by vortexing for 15 sec. The sample was placed on ice for another 5 min, followed by centrifugation at 12,000×g for 15 min at 4° C. The upper layer was collected and transferred to another RNase-free 2.0 ml microfuge tube. An equal volume of isopropanol was added to each sample, and the solution was placed on ice for 10 min. The sample was centrifuged at 12,000×g for 10 min at 4° C., and the supernatant was discarded. The remaining pellet was washed twice with cold 75% ethanol, resuspended by vortexing, and the resuspended material was then pelleted by centrifugation at 7500×g for 5 min at 4° C. Finally, the RNA pellet was dried in a Speedvac (Savant, Farmingdale, N.Y.) for 5 min and reconstituted in RNase-free water.

B. RNA Extraction from Blood Mononuclear Cells. Mononuclear cells are isolated from blood samples from patients by centrifugation using Ficoll-Hypaque as follows. A 10 ml volume of whole blood is mixed with an equal volume of RPMI Medium (Gibco-BRL, Grand Island, N.Y.). This mixture is then underlayed with 10 ml of Ficoll-Hypaque (Pharmacia, Piscataway, N.J.) and centrifuged for 30 minutes at 200×g. The buffy coat containing the mononuclear cells is removed, diluted to 50 ml with Dulbecco's PBS (Gibco-BRL, Grand Island, N.Y.) and the mixture centrifuged for 10 minutes at 200×g. After two washes, the resulting pellet is resuspended in Dulbecco's PBS to a final volume of 1 ml.

RNA is prepared from the isolated mononuclear cells as described by N. Kato et al., *J. Virology* 61: 2182–2191 (1987). Briefly, the pelleted mononuclear cells are brought to a final volume of 1 ml and then are resuspended in 250 μL of PBS and mixed with 2.5 ml of 3 M LiCl, 6 M urea, 5 mM EDTA, 0.1 M 2-mercaptoethanol, 50 mM Tris-HCl (pH 7.5). The resulting mixture is homogenized and incubated at -20° C. overnight. The homogenate is centrifuged at 8,000 RPM in a Beckman J2-21M rotor for 90 minutes at 0–4° C. The pellet is resuspended in 10 ml of 3 M LiCl by vortexing and then centrifuged at 10,000 RPM in a Beckman J2-21 M rotor centrifuge for 45 minutes at 0–4° C. The resuspending and pelleting steps are then repeated. The pellet is resuspended in 2 ml of I mM EDTA, 0.5% SDS, 10 mM Tris (pH 7.5) and 400 μg Proteinase K with vortexing and then it is incubated at 37° C. for 30 minutes with shaking. One tenth volume of 3 M NaCl then is added and the mixture is vortexed. Proteins are removed by two cycles of extraction with phenol/chloroform/isoamyl alcohol (PCI) followed by one extraction with chloroform/isoamyl alcohol (CI). RNA is precipitated by the addition of 6 ml of absolute ethanol followed by overnight incubation at -20° C. After the precipitated RNA is collected by centrifugation, the pellet is washed 4 times in 75% ethanol. The pelleted RNA is then dissolved in solution containing 1 mM EDTA, 10 mM Tris-HCl (pH 7.5).

Non-GI tract tissues are used as negative controls. The mRNA can be further purified from total RNA by using commercially available kits such as oligo dT cellulose spin columns (RediCol™ from Pharmacia, Uppsala, Sweden) for the isolation of poly-adenylated RNA. Total RNA or mRNA can be dissolved in lysis buffer (5 M guanidine thiocyanate, 0.1 M EDTA, pH 7.0) for analysis in the ribonuclease protection assay.

C. RNA Extraction from polysomes. Tissue is minced in saline at 4° C. and mixed with 2.5 volumes of 0.8 M sucrose in a $TK_{150}M$ (150 mM KCl, 5 mM $MgCl_2$, 50 mM Tris-HCl, pH 7.4) solution containing 6 mM 2-mercaptoethanol. The tissue is homogenized in a Teflon-glass Potter homogenizer with five strokes at 100–200 rpm followed by six strokes in a Dounce homogenizer, as described by B. Mechler, *Methods in Enzymology* 152:241–248 (1987). The homogenate then is centrifuged at 12,000×g for 15 min at 4° C. to sediment the nuclei. The polysomes are isolated by mixing 2 ml of the supernatant with 6 ml of 2.5 M sucrose in $TK_{150}M$ and layering this mixture over 4 ml of 2.5 M sucrose in $TK_{150}M$ in a 38 ml polyallomer tube. Two additional sucrose $TK_{150}M$ solutions are successively layered onto the extract fraction; a first layer of 13 ml 2.05 M sucrose followed by a second layer of 6 ml of 1.3 M sucrose. The polysomes are isolated by centrifuging the gradient at 90,000×g for 5 hr at 4° C. The fraction then is taken from the 1.3 M sucrose/2.05 M sucrose interface with a siliconized pasteur pipette and diluted in an equal volume of TE (10 mM Tris-HCl, pH 7.4, 1 mM EDTA). An equal volume of 90° C. SDS buffer (1% SDS, 200 mM NaCl, 20 mM Tris-HCl, pH 7.4) is added and the solution is incubated in a boiling water bath for 2 min. Proteins next are digested with a Proteinase-K digestion (50 mg/ml) for 15 min at 37° C. The mRNA is purified with 3 equal volumes of phenol-chloroform extractions followed by precipitation with 0.1 volume of 2 M sodium acetate (pH 5.2) and 2 volumes of 100% ethanol at -20° C. overnight. The precipitated RNA is recovered by centrifugation at 12,000×g for 10 min at 4° C. The RNA is dried and resuspended in TE (pH 7.4) or distilled water. The resuspended RNA then can be used in a slot blot or dot blot hybridization assay to check for the presence of PS108 mRNA (see Example 6).

The quality of nucleic acid and proteins is dependent on the method of preparation used. Each sample may require a different preparation technique to maximize isolation efficiency of the target molecule. These preparation techniques are within the skill of the ordinary artisan.

Example 4

Ribonuclease Protection Assay

A. Synthesis of Labeled Complementary RNA (cRNA) Hybridization Probe and Unlabeled Sense Strand. Labeled antisense and unlabeled sense riboprobes are transcribed from the PS108 gene cDNA sequence which contains a 5' RNA polymerase promoter such as SP6 or 17. The sequence may be from a vector containing the appropriate PS108 cDNA insert, or from a PCR-generated product of the insert using PCR primers which incorporate a 5' RNA polymerase promoter sequence. For example, the described plasmid (clone 1281865), or another comparable clone containing the PS108 gene cDNA sequence flanked by opposed SP6 and T7 polymerase promoters, is purified using Qiagen Plasmid Purification Kit (Qiagen, Chatsworth, Calif.). Then 10 μg of the plasmid are linearized by cutting with 10 U DdeI restriction enzyme for 1 hr at 37° C. The linearized plasmid is purified using QIAprep kits (Qiagen, Chatsworth, Calif.) and used for the synthesis of antisense transcript from the appropriate SP6 or T7 promoter using the Riboprobe® in vitro Transcription System (Promega Corporation, Madison, Wis.), as described by the supplier's instructions, incorporating either 6.3 μM (alpha$^{32}$P) CTP (Amersham Life Sciences, Inc. Arlington Heights, Ill.) or 100–500 μM biotinylated CTP as a label. To generate the sense strand, 10 μg of the purified plasmid are cut with restriction enzymes 10U XbaI and 10 U NotI, and transcribed as above from the appropriate SP6 or T7 promoter. Both sense and antisense strands are isolated by spin column chromatography. Unlabeled sense strand is quantitated by UV absorption at 260 nm.

B. Hybridization of Labeled Probe to Target. Frozen tissue is pulverized to powder under liquid nitrogen and 100–500 mg are dissolved in 1 ml of lysis buffer, available as a component of the Direct Protect™ Lysate RNase Protection kit (Ambion, Inc., Austin, Tex.). Further dissolution can be achieved using a tissue homogenizer. In addition, a dilution series of a known amount of sense strand in mouse liver lysate is made for use as a positive control. Finally, 45 µl of solubilized tissue or diluted sense strand is mixed directly with either: (1) 1×10$^5$ cpm of radioactively labeled probe; or (2) 250 µg of non-isotopically labeled probe in 5 µl of lysis buffer. Hybridization is allowed to proceed overnight at 37° C. See, T. Kaabache et al., *Anal. Biochem.* 232:225–230 (1995).

C. RNase Digestion. RNA that is not hybridized to probe is removed from the reaction as per the Direct Protect™ protocol using a solution of RNase A and RNase T1 for 30 min at 37° C., followed by removal of RNase by Proteinase-K digestion in the presence of sodium sarcosyl. Hybridized fragments protected from digestion are then precipitated by the addition of an equal volume of isopropanol and placed at −70° C. for 3 hr. The precipitates are collected by centrifugation at 12,000×g for 20 min.

D. Fragment Analysis. The precipitates are dissolved in denaturing gel loading dye (80% formamide, 10 mM EDTA (pH 8.0), 1 mg/ml xylene cyanol, 1 mg/ml bromophenol blue), heat denatured, and electrophoresed in 6% polyacrylamide TBE, 8 M urea denaturing gels. The gels are imaged and analyzed using the STORM™ storage phosphor autoradiography system (Molecular Dynamics, Sunnyvale, Calif.). Quantitation of protected fragment bands, expressed in femtograms (fg), is achieved by comparing the peak areas obtained from the test samples to those from the known dilutions of the positive control sense strand (see Section B, supra). The results are expressed in molecules of PS108 RNA/cell and as a image rating score. In cases where non-isotopic labels are used, hybrids are transferred from the gels to membranes (nylon or nitrocellulose) by blotting and then analyzed using detection systems that employ streptavidin alkaline phosphatase conjugates and chemiluminesence or chemifluoresence reagents.

Detection of a product comprising a sequence selected from the group consisting of SEQUENCE ID NOS 1–16 and fragments or complements thereof, is indicative of the presence of PS108 mRNAs, suggesting a diagnosis of a prostate tissue disease or condition, such as prostate cancer.

Example 5

Northern Blotting

The northern blot technique is used to identify a specific size RNA fragment from a complex population of RNA using gel electrophoresis and nucleic acid hybridization. Northern blotting is a technique well-known in the art. Briefly, 5–10 µg of total RNA (see Example 3) are incubated in 15 µl of a solution containing 40 mM morphilinopropanesulfonic acid (MOPS) (pH 7.0), 10 mM sodium acetate, 1 mM EDTA, 2.2 M formaldehyde, 50% v/v formamide for 15 min at 65° C. The denatured RNA is mixed with 2 µl of loading buffer (50% glycerol, 1 mM EDTA, 0.4% bromophenol blue, 0.4% xylene cyanol) and loaded into a denaturing 1.0% agarose gel containing 40 mM MOPS (pH 7.0), 10 mM sodium acetate, 1 mM EDTA and 2.2 M formaldehyde. The gel is electrophoresed at 60 V for 1.5 h and rinsed in RNAse free water. RNA is transferred from the gel onto nylon membranes (Brightstar-Plus, Ambion, Inc., Austin, Tex.) for 1.5 hours using the downward alkaline capillary transfer method (Chomczynski, *Anal. Biochem.* 201:134–139, 1992). The filter is rinsed with 1×SSC, and RNA is crosslinked to the filter using a Stratalinker (Stratagene, Inc., La Jolla, Calif.) on the autocrosslinking mode and dried for 15 min. The membrane is then placed into a hybridization tube containing 20 ml of preheated prehybridization solution (5×SSC, 50% formamide, 5×Denhardt's solution, 100 µg/ml denatured salmon sperm DNA) and incubated in a 42° C. hybridization oven for at least 3 hr. While the blot is prehybridizing, a $^{32}$P-labeled random-primed probe is generated using the PS108 insert fragment (obtained by digesting clone 1711346 or another comparable clone with XbaI and NotI) using Random Primer DNA Labeling System (Life Technologies, Inc., Gaithersburg, Md.) according to the manufacturer's instructions. Half of the probe is boiled for 10 min, quick chilled on ice and added to the hybridization tube. Hybridization is carried out at 42° C. for at least 12 hr. The hybridization solution is discarded and the filter is washed in 30 ml of 3×SSC, 0.1% SDS at 42° C. for 15 min, followed by 30 ml of 3×SSC, 0.1% SDS at 42° C. for 15 min. The filter is wrapped in Saran Wrap and exposed to Kodak XAR-Omat film for 8–96 hr and the film is developed for analysis.

Detection of a product comprising a sequence selected from the group consisting of SEQUENCE ID NOS 1–16 and fragments or complements thereof, is indicative of the presence of PS108 mRNAs, suggesting a diagnosis of a prostate tissue disease or condition, such as prostate cancer.

Example 6

Dot Blot/Slot Blot

Dot and slot blot assays are quick methods to evaluate the presence of a specific nucleic acid sequence in a complex mix of nucleic acid. To perform such assays, up to 50 µg of RNA are mixed in 50 µl of 50% formamide, 7% formaldehyde, 1×SSC, incubated 15 min at 68° C., and then cooled on ice. Then, 100 µl of 20×SSC are added to the RNA mixture and loaded under vacuum onto a manifold apparatus that has a prepared nitrocellulose or nylon membrane. The membrane is soaked in water, 20×SSC for 1 hour, placed on two sheets of 20×SSC prewet Whatman #3 filter paper, and loaded into a slot blot or dot blot vacuum manifold apparatus. The slot blot is analyzed with probes prepared and labeled as described in Example 4, supra. Detection of mRNA corresponding to a sequence selected from the group consisting of SEQUENCE ID NOS 1–16 and fragments or complements thereof, is indicative of the presence of PS108 mRNAs, suggesting a diagnosis of a prostate tissue disease or condition, such as prostate cancer.

Other methods and buffers which can be utilized in the methods described in Examples 5 and 6, but not specifically detailed herein, are known in the art and are described in J. Sambrook et al, supra which is incorporated herein by reference.

Example 7

In Situ Hybridization

This method is useful to directly detect specific target nucleic acid sequences in cells using detectable nucleic acid hybridization probes.

Tissues are prepared with cross-linking fixative agents such as paraformaldehyde or glutaraldehyde for maximum cellular RNA retention. See, L. Angerer et al., *Methods in Cell Biol.* 35:37–71 (1991). Briefly, the tissue is placed in greater than 5 volumes of 1% glutaraldehyde in 50 mM sodium phosphate, pH 7.5 at 4° C. for 30 min. The solution is changed with fresh glutaraldehyde solution (1% glutaraldehyde in 50 mM sodium phosphate, pH 7.5) for a further 30 min fixing. The fixing solution should have an osmolality of approximately 0.375% NaCl. The tissue is washed once in isotonic NaCl to remove the phosphate.

The fixed tissues then are embedded in paraffin as follows. The tissue is dehydrated though a series of increasing ethanol concentrations for 15 mill each: 50% (twice), 70% (twice), 85%, 90% and then 100% (twice). Next, the tissue is soaked in two changes of xylene for 20 min each at room temperature. The tissue is then soaked in two changes of a 1:1 mixture of xylene and paraffin for 20 min each at 60° C.; and then in three final changes of paraffin for 15 min each.

Next, the tissue is cut in 5 µm sections using a standard microtome and placed on a slide previously treated with a tissue adhesive such as 3-aminopropyltriethoxysilane.

Paraffin is removed from the tissue by two 10 min xylene soaks and rehydrated in a series of decreasing ethanol concentrations: 99% (twice), 95%, 85%, 70%, 50%, 30%, and then in distilled water (twice). The sections are pretreated with 0.2 M HCl for 10 min and permeabilized with 2 µg/ml Proteinase-K at 37° C. for 15 min.

Labeled Riboprobes transcribed from the PS108 gene plasmid (see Example 4) are hybridized to the prepared tissue sections and incubated overnight at 56° C. in 3×standard saline extract and 50% formamide. Excess probe is removed by washing in 2×standard saline citrate and 50% formamide followed by digestion with 100 µg/ml RNase A at 37° C. for 30 min. Fluorescence probe is visualized by illumination with ultraviolet (UV) light under a microscope. Fluorescence in the cytoplasm is indicative of PS108 mRNA. Alternatively, the sections can be visualized by autoradiography.

Detection of a product comprising a sequence selected from the group consisting of SEQUENCE ID NOS 1–16 and fragments or complements thereof, is indicative of the presence of PS108 mRNAs, suggesting a diagnosis of a prostate tissue disease or condition, such as prostate cancer.

Example 8

Reverse Transcription PCR

A. One Step RT-PCR Assay. Target-specific primers are designed to detect the above-described target sequences by reverse transcription PCR using methods known in the art. One step RT-PCR is a sequential procedure that performs both RT and PCR in a single reaction mixture. The procedure is performed in a 200 µl reaction mixture containing 50 mM (N,N,-bis[2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 µM each of dNTP, 0.25 µM each primer, 5U rTth polymerase, 3.25 mM Mn(OAc)$_2$ and 5 µl of target RNA (see Example 3). Since RNA and the rTth polymerase enzyme are unstable in the presence of Mn(OAc)$_2$, the Mn(OAc)$_2$ should be added just before target addition. Optimal conditions for cDNA synthesis and thermal cycling readily can be determined by those skilled in the art. The reaction is incubated in a Perkin-Elmer Thermal Cycler 480. Optimal conditions for cDNA synthesis and thermal cycling can readily be determined by those skilled in the art. Conditions which may be found useful include cDNA synthesis at 60°–70° C. for 15–45 min and 30–45 amplification cycles at 94° C., 1 min; 55°–70° C., 1 min; 72° C., 2 min. One step RT-PCR also may be performed by using a dual enzyme procedure with Taq polymerase and a reverse transcriptase enzyme, such as MMLV or AMV RT enzymes.

B. Traditional RT-PCR. A traditional two-step RT-PCR reaction was performed, as described by K. Q. Hu et al., *Virology* 181:721–726 (1991). Briefly, 1.0 µg of extracted mRNA (see Example 3) was reverse transcribed in a 20 µl reaction mixture containing 1×PCR II buffer (Perkin-Elmer), 5 mM MgCl$_2$, 1 mM dNTP, 20 U RNasin, 2.5 µM random hexamers, and 50 U MMLV (Moloney murine leukemia virus) reverse transcriptase (RT). Reverse transcription was performed at room temperature for 10 min, 42° C. for 30 min in a PE-480 thermal cycler, followed by further incubation at 95° C. for 5 min to inactivate the RT. PCR was performed using 2 µl of the cDNA reaction in a final PCR reaction volume of 50 µl containing 10 mM Tris-HCl (pH 8.3),50 mM KCl, 1.5 mM MgCl$_2$, 200 µM dNTP, 0.4 µM of each sense and antisense primer (SEQUENCE ID NO 34 and SEQUENCE ID NO 35, respectively), and 2.5 U of Taq polymerase. The reaction was incubated in an MJ Research Model PTC-200 as follows: Denaturation at 94° C. for 2 min. followed by 35 cycles of amplification (94° C., 45 sec; 62 ° C., 45 sec; 72° C., 2 min ); a final extension (72° C., 5 min); and a soak at 4° C.

Figure 3B:
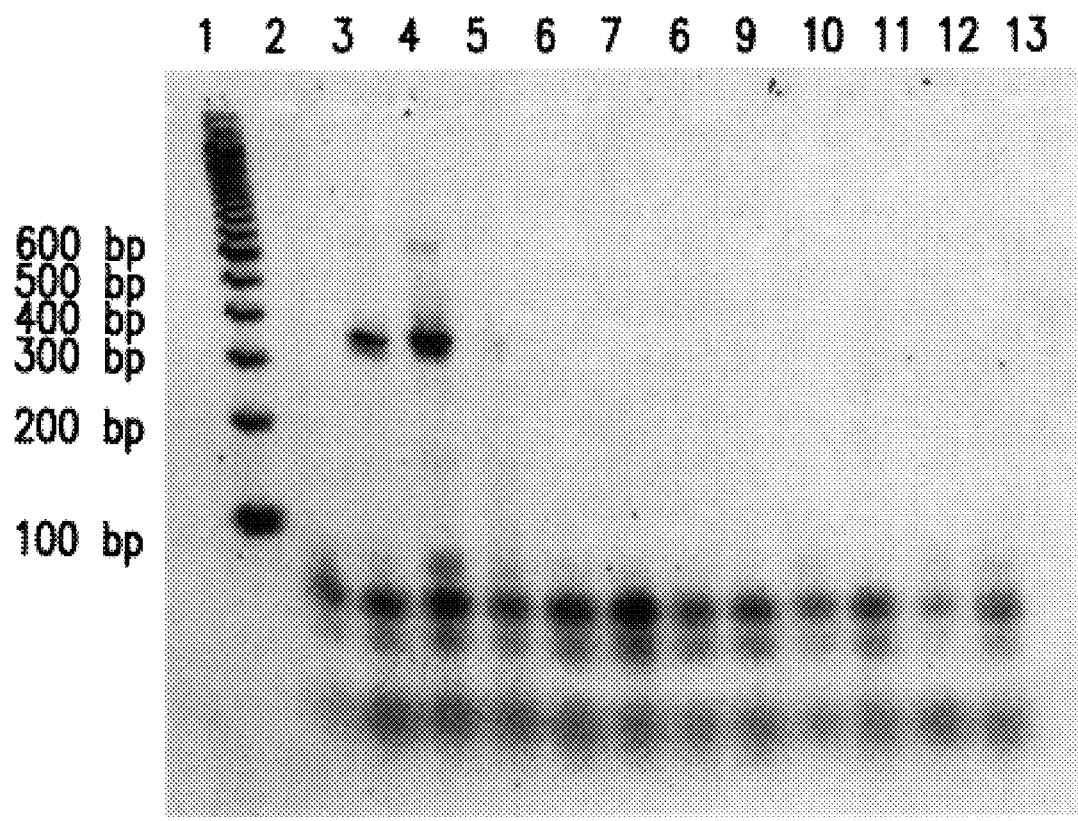
FIG. 3B is a scan of a SYBR® Green-stained agarose gel of PS108 RNA-specific RT-PCR amplification products of RNAs from normal or cancerous placenta, colon, breast, prostate, and lung tissues.

C. PCR Fragment Analysis. The correct products were verified by size determination using gel electrophoresis with a SYBR® Green I nucleic acid gel stain (Molecular Probes, Eugene, Oreg.). Gels were stained with SYBR® Green I at a 1:10,000 dilution in 1×TBE for 30 minutes. Gels were imaged using a STORM imaging system (FIGS. 3A–3B). More particularly, FIG. 3A shows a 344 bp PS108-specific PCR amplification product in lanes 3–6 and lanes 9–10. The 344 hp PS108-specific amplicon was present in 2 of 4 prostate cancer tissue RNAs (lanes 5 and 9) and in 3 of 3 BPH prostate tissue RNAs (lanes 3, 4, and 6). (The BPH sample in lane 10 was a diluted duplicate of the sample in lane 6.) The human placental DNA control (lane 2) was negative in the analysis, suggesting that the amplicons in lanes 3–6 and lanes 9–10 were the result of amplification of mRNA and not DNA. As shown in FIG. 3B, the 344 bp amplicon was detected in RNAs from BPH and prostate cancer tissues (lanes 3 and 4, respectively) and in one of two colon cancer tissues (lane 5). This RNA-specific product was not observed in human placental DNA (lane 2). Further, this RNA-specific product was not observed in RNAs isolated from a different colon cancer tissue sample (lane 6), a normal colon tissue sample (lane 7), breast cancer tissue samples (lanes 8–9), a normal breast tissue sample (lane 10), normal lung tissue samples (lane 11–12) or a lung cancer tissue sample (lane 13).

Detection of a product comprising a sequence selected from the group consisting of SEQUENCE ID NOS 1–16 and fragments or complements thereof, is indicative of the presence of PS108 mRNAs, suggesting a diagnosis of a prostate tissue disease or condition, such as prostate cancer.

Example 9

OH-PCR

A. Probe selection and Labeling. Target-specific primers and probes are designed to detect the above-described target sequences by oligonucleotide hybridization PCR. International Publication Nos WO 92/10505, published Jun. 25, 1992, and WO 92/11388, published Jul. 9, 1992, teach methods for labeling oligonucleotides at their 5' and 3' ends, respectively. According to one known method for labeling an oligonucleotide, a label-phosphoramidite reagent is prepared and used to add the label to the oligonucleotide during its synthesis. For example, see N. T. Thuong et al., *Tet. Letters* 29(46):5905–5908 (1988); or J. S. Cohen et al., published U.S. patent application Ser. No. 07/246,688 (NTIS ORDER No. PAT-APPL-7-246,688) (1989). Preferably, probes are labeled at their 3' end to prevent participation in PCR and the formation of undesired extension products. For one step OH-PCR, the probe should have a $T_M$ at least 15° C. below the $T_M$ of the primers. The primers and probes are utilized as specific binding members, with or without detectable labels, using standard phosphoramidite chemistry and/or post-synthetic labeling methods which are well-known to one skilled in the art.

B. One Step Oligo Hybridization PCR. OH-PCR is performed on a 200 µl reaction containing 50 mM (N,N,-bis[2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 µM each of dNTP, 0.25 µM each primer, 3.75 nM probe, 5U rTth polymerase, 3.25 mM Mn(OAc)$_2$ and 5 µl blood equivalents of target (see Example 3). Since RNA and the rTth polymerase enzyme are unstable in the presence of Mn(OAc)$_2$, the Mn(OAc)$_2$ should be added just before target addition. The reaction is incubated in a Perkin-Elmer Thermal Cycler 480. Optimal conditions for cDNA synthesis and thermal cycling can be readily determined by those skilled in the art. Conditions which may be found useful include cDNA synthesis (60° C., 30 min), 30–45 amplification cycles (94° C., 40 sec; 55–70° C., 60 sec), oligo-hybridization (97° C., 5 min; 15° C., 5 min; 15° C. soak). The correct reaction product contains at least one of the strands of the PCR product and an internally hybridized probe.

C. OH-PCR Product Analysis. Amplified reaction products are detected on an LCx® analyzer system (available from Abbott Laboratories, Abbott Park, Ill.). Briefly, the correct reaction product is captured by an antibody labeled microparticle at a capturable site on either the PCR product strand or the hybridization probe, and the complex is detected by binding of a detectable antibody conjugate to either a detectable site on the probe or the PCR strand. Only a complex containing a PCR strand hybridized with the internal probe is detectable. The detection of this complex then is indicative of the presence of PS108 mRNA, suggesting a diagnosis of a prostate disease or condition, such as prostate cancer.

Many other detection formats exist which can be used and/or modified by those skilled in the art to detect the presence of amplified or non-amplified PS108-derived nucleic acid sequences including, but not limited to, ligase chain reaction (LCR, Abbott Laboratories, Abbott Park, Ill.); Q-beta replicase (Gene-Trak™, Naperville, Ill.), branched chain reaction (Chiron, Emeryville, Calif.) and strand displacement assays (Becton Dickinson, Research Triangle Park, N.C.).

Detection of a product comprising a sequence selected from the group consisting of SEQUENCE ID NOS 1–16 and fragments or complements thereof, is indicative of the presence of PS108 mRNAs, suggesting a diagnosis of a prostate tissue disease or condition, such as prostate cancer.

Example 10

Synthetic Peptide Production

Synthetic peptides were modeled and then prepared based upon the predicted amino acid sequence of the PS108 polypeptide consensus sequence (see Example 1). In particular, a number of PS108 peptides derived from SEQUENCE ID NO 36 were prepared, including the peptides of SEQUENCE ID NO 37, SEQUENCE ID NO 38, and SEQUENCE ID NO 39. All peptides were synthesized on a Symphony Peptide Synthesizer (available from Rainin Instrument Co, Emeryville, Calif.) using FMOC chemistry, standard cycles and in-situ HBTU activation. Cleavage and deprotection conditions were as follows: a volume of 2.5 ml of cleavage reagent (77.5% v/v trifluoroacetic acid, 15% v/v ethanedithiol, 2.5% v/v water, 5% v/v thioanisole, 1–2% w/v phenol) was added to the resin, and agitated at room temperature for 2–4 hours. Then the filtrate was removed and the peptide was precipitated from the cleavage reagent with cold diethyl ether. Each peptide was filtered, purified via reverse-phase preparative HPLC using a water/acetonitrile/0.1% TFA gradient, and lyophilized. The product was confirmed by mass spectrometry.

The purified peptides were used to immunize animals (see Example 14).

Example 11a

Expression of Protein in a Cell Line Using Plasmid 577

A. Construction of a PS108 Expression Plasmid. Plasmid 577, described in U.S. patent application Ser. No. 08/478, 073, filed Jun. 7, 1995 and incorporated herein by reference, has been constructed for the expression of secreted antigens in a permanent cell line. This plasmid contains the following DNA segments: (a) a 2.3 Kb fragment of pBR322 containing bacterial beta-lactamase and origin of DNA replication; (b) a 1.8 Kb cassette directing expression of a neomycin resistance gene under control of HSV-1 thymidine kinase promoter and poly-A addition signals; (c) a 1.9 Kb cassette directing expression of a dihydrofolate reductase gene under the control of an SV-40 promoter and poly-A addition signals; (d) a 3.5 Kb cassette directing expression of a rabbit immunoglobulin heavy chain signal sequence fused to a modified hepatitis C virus (HCV) E2 protein under the control of the Simian Virus 40 T-Ag promoter and transcription enhancer, the hepatitis B virus surface antigen (HBsAg) enhancer I followed by a fragment of Herpes Simplex Virus-1 (HSV-1) genome providing poly-A addition signals; and (e) a residual 0.7 Kb fragment of Simian Virus 40 genome late region of no function in this plasmid. All of the segments of the vector were assembled by standard methods known to those skilled in the art of molecular biology.

Plasmids for the expression of secretable PS108 proteins are constructed by replacing the hepatitis C virus E2 protein coding sequence in plasmid 577 with that of a PS108 polynucleotide sequence selected from the group consisting of SEQUENCE ID NOS 1–16 and fragments or complements thereof, as follows. Digestion of plasmid 577 with XbaI releases the hepatitis C virus E2 gene fragment. The resulting plasmid backbone allows insertion of the PS108 cDNA insert downstream of the rabbit immunoglobulin heavy chain signal sequence which directs the expressed proteins into the secretory pathway of the cell. The PS108 cDNA fragment is generated by PCR using standard procedures. Encoded in the sense PCR primer sequence is an XbaI site, immediately followed by a 12 nucleotide sequence that encodes the amino acid sequence Ser-Asn-Glu-Leu ("SNEL") to promote signal protease processing, efficient secretion and final product stability in culture fluids. Immediately following this 12 nucleotide sequence, the primer contains nucleotides complementary to template sequences encoding amino acids of the PS108 gene. The antisense primer incorporates a sequence encoding the following eight amino acids just before the stop codons: Asp-Tyr-Lys-Asp-Asp-Asp-Asp-Lys (SEQUENCE ID NO 40). Within this sequence is incorporated a recognition site to aid in analysis and purification of the PS108 protein product. A recognition site (termed "FLAG") that is recognized by a commercially available monoclonal antibody designated anti-FLAG M2 (Eastman Kodak, Co., New Haven, Conn.) can be utilized, as well as other comparable sequences and their corresponding antibodies. For example, PCR is performed using Gene-Amp® reagents obtained from Perkin-Elmer-Cetus, as directed by the supplier's instructions. PCR primers are used at a final concentration of 0.5 µM. PCR is performed on the PS108 plasmid template in a 100 µl reaction for 35 cycles (94° C., 30 seconds; 55° C., 30 seconds; 72° C., 90 seconds) followed by an extension cycle of 72° C. for 10 min.

B. Transfection of Dihydrofolate Reductase Deficient Chinese Hamster Ovary Cells. The plasmid described supra is transfected into CHO/dhfr-cells (DXB-111, Uriacio et al., PNAS 77:4451–4466 (1980)). These cells are available from the A.T.C.C., 12301 Parklawn Drive, Rockville, Md. 20852, under Accession No. CRL 9096. Transfection is carried out using the cationic liposome-mediated procedure described by P. L. Feigner et al., PNAS 84:7413–7417 (1987). Particularly, CHO/dhfr-cells are cultured in Ham's F-12 media supplemented with 10% fetal calf serum, L-glutamine (1 mM) and freshly seeded into a flask at a density of $5-8 \times 10^5$ cells per flask. The cells are grown to a confluency of between 60 and 80% for transfection. Twenty micrograms (20 µg) of plasmid DNA is added to 1.5 ml of Opti-MEM I medium and 100 µl of Lipofectin Reagent (Gibco-BRL; Grand Island, N.Y.) are added to a second 1.5 ml portion of Opti-MEM I media. The two solutions are mixed and incubated at room temperature for 20 min. After the culture medium is removed from the cells, the cells are rinsed 3 times with 5 ml of Opti-MEM I medium. The Opti-MEM I-Lipofection-plasmid DNA solution then is overlaid onto the cells. The cells are incubated for 3 h at 37° C., after which time the Opti-MEM I-Lipofectin-DNA solution is replaced with culture medium for an additional 24 h prior to selection.

C. Selection and Amplification. One day after transfection, cells are passaged 1:3 and incubated with dhfr/G418 selection medium (hereafter, "F-12 minus medium G"). Selection medium is Ham's F-12 with L-glutamine and without hypoxanthine, thymidine and glycine (JRH Biosciences, Lenexa, Kans.) and 300 µg ml G418 (Gibco-BRL; Grand Island, N.Y.). Media volume-to-surface area ratios of 5 ml per 25 cm² are maintained. After approximately two weeks, DHFR/G418 cells are expanded to allow passage and continuous maintenance in F-12 minus medium G.

Amplification of each of the transfected PS108 cDNA sequences is achieved by stepwise selection of DHFR⁺, G418⁺ cells with methotrexate [reviewed by R. Schimke, Cell 37:705–713 (1984)]. Cells are incubated with F-12 minus medium G containing 150 nM methotrexate (MTX) (Sigma, St. Louis, Mo.) for approximately two weeks until resistant colonies appear. Further gene amplification is achieved by selection of 150 nM adapted cells with 5 µM MTX.

D. Antigen Production. F-12 minus medium G supplemented with 5 µM MTX is overlaid onto just confluent monolayers for 12 to 24 h at 37° C. in 5% $CO_2$. The growth medium is removed and the cells are rinsed 3 times with Dulbecco's phosphate buffered saline (PBS) (with calcium and magnesium) (Gibco-BRL; Grand Island, N.Y.) to remove the remaining media/serum which may be present. Cells then are incubated with VAS custom medium (VAS custom formulation with L-glutamine with HEPES without phenol red, available from JRH Bioscience; Lenexa, Kans., product number 52-08678P), for 1 h at 37° C. in 5% $CO_2$. Cells then are overlaid with VAS for production at 5 ml per T flask. Medium is removed after seven days of incubation, retained, and then frozen to await purification with harvests 2, 3 and 4. The monolayers are overlaid with VAS for 3 more seven day harvests.

E. Analysis of Prostate Tissue Gene PS108 Antigen Expression. Aliquots of VAS supernatants from the cells expressing the PS108 protein construct are analyzed, either by SDS-polyacrylamide gel electrophoresis (SDS-PAGE) using standard methods and reagents known in the art (Laemmli discontinuous gels), or by mass spectrometry.

F. Purification. Purification of the PS108 protein containing the FLAG sequence is performed by immunoaffinity chromatography using an affinity matrix comprising anti-FLAG M2 monoclonal antibody covalently attached to agarose by hydrazide linkage (Eastman Kodak Co., New Haven, Conn.). Prior to affinity purification, protein in pooled VAS medium harvests from roller bottles is exchanged into 50 mM Tris-HCl (pH 7.5), 150 mM NaCl buffer using a Sephadex G-25 (Pharmacia Biotech Inc., Uppsala, Sweden) column. Protein in this buffer is applied to the anti-FLAG M2 antibody affinity column. Non-binding protein is eluted by washing the column with 50 mM Tris-HCl (pH 7.5), 150 mM NaCl buffer. Bound protein is eluted using an excess of FLAG peptide in 50 mM Tris-HCl (pH 7.5), 150 mM NaCl. The excess FLAG peptide can be removed from the purified PS108 protein by gel electrophoresis or HPLC.

Although plasmid 577 is utilized in this example, it is known to those skilled in the art that other comparable expression systems, such as CMV, can be utilized herein with appropriate modifications in reagent and/or techniques and are within the skill of the ordinary artisan.

The largest cloned insert containing the coding region of the PS108 gene is then sub-cloned into either (i) a eukaryotic expression vector which may contain, for example, a cytomegalovirus (CMV) promoter and/or protein fusible sequences which aid in protein expression and detection, or (ii) a bacterial expression vector containing a superoxide-dismutase (SOD) and CMP-KDO synthetase (CKS) or other protein fusion gene for expression of the protein sequence. Methods and vectors which are useful for the production of polypeptides which contain fusion sequences of SOD are described in EPO 0196056, published Oct. 1, 1986, which is incorporated herein by reference and those containing fusion sequences of CKS are described in EPO Publication No. 0331961, published Sep. 13, 1989, which publication is also incorporated herein by reference. This so-purified protein can be used in a variety of techniques, including, but not limited to animal immunization studies, solid phase immunoassays, etc.

Example 11b

Expression of Protein in a Cell Line Using pcDNA3.1/Myc-His

A. Construction of a PS108 Expression Plasmid. Plasmid pcDNA3.1/Myc-His (Cat. #V855-20, Invitrogen, Carlsbad, Calif.) was developed for the expression of secreted antigens by most mammalian cell lines. Expressed protein inserts are fused to a myc-his peptide tag. The myc-his tag is a 21 residue amino acid sequence having the following sequence: Glu-Gln-Lys-Leu-Ile-Ser-Glu-Glu-Asp-Leu-Asn-Met-His-Thr-Glu-His-His-His-His-His-His (SEQUENCE ID NO 41) and comprises a c-myc oncoprotein epitope and a polyhistidine sequence which are useful for the purification of an expressed fusion protein by using either anti-myc or anti-his affinity columns, or metalloprotein binding columns.

Plasmids for the expression of secretable PS108 proteins are constructed by inserting a PS108 polynucleotide sequence selected from the group consisting of SEQUENCE ID NOS 1–16 and fragments or complements thereof. Prior to construction of a PS108 expression plasmid, the PS108 cDNA sequence is first cloned into a pCR®-Blunt vector as follows.

The PS108 cDNA fragment is generated by PCR using standard procedures. For example, PCR is performed using Stratagene® reagents obtained from Stratagene, as directed by the supplier's instructions. PCR primers are used at a final concentration of 0.5 $\mu$M. PCR using 5 U of pfu polymerase (Stratagene, La Jolla, Calif.) is performed on the PS108 plasmid template (see Example 2) in a 50 $\mu$l reaction for 30 cycles (94° C., 1 min; 65° C., 1.5 min; 72° C., 3 min) followed by an extension cycle of 72° C. for 8 min. (The sense PCR primer sequence comprises nucleotides which are either complementary to the pINCY vector directly upstream of the PS108 gene insert or which incorporate a 5' EcoRI restriction site, an adjacent downstream protein translation consensus initiator, and a 3' nucleic acid sequence which is the same sense as the 5'-most end of the PS108 cDNA insert. The antisense primer incorporates a 5' NotI restriction sequence and a sequence complementary to the 3' end of the PS108 cDNA insert just upstream of the 3'-most, in-frame stop codon.) Five microliters (5 $\mu$l) of the resulting blunted-ended PCR product are ligated into 25 ng of linearized pCR®-Blunt vector (Invitrogen, Carlsbad, Calif.) interrupting the lethal ccdB gene of the vector. The resulting ligated vector is transformed into TOP10 *E. coli* (Invitrogen, Carlsbad, Calif.) using a One Shot™ transformation kit (Invitrogen, Carlsbad, Calif.) following supplier's directions. The transformed cells are grown on LB-Kan (50 $\mu$g/ml kanamycin) selection plates at 37° C. Only cells containing a plasmid with an interrupted ccdB gene will grow after transformation (Grant, S. G. N., *PNAS* 87:4645–4649 (1990)). Transformed colonies are picked and grown up in 3 ml of LB-Kan broth at 37° C. Plasmid DNA is isolated by using a QIAprep® (Qiagen Inc., Santa Clarita, Calif.) procedure, as directed by the supplier's instructions. The DNA is cut with EcoRI or SnaBI, and NotI restriction enzymes to release the PS108 insert fragment. The fragment is run on 1% Seakem® LE agarose/0.5 $\mu$g/ml ethidium bromide/TE gel, visualized by UV irradiation, excised and purified using QIAquick™ (Qiagen Inc., Santa Clarita, Calif.) procedures, as directed by the supplier's instructions.

The pcDNA3.1/Myc-His plasmid DNA is linearized by digestion with EcoRI or SnaBI, and NotI in the polylinker region of the plasmid DNA. The resulting plasmid DNA backbone allows insertion of the PS108 purified cDNA fragment, supra, downstream of a CMV promoter which directs expression of the proteins in mammalian cells. The ligated plasmid is transformed into DH5 alpha™ cells (GibcoBRL Gaithersburg, Md.), as directed by the supplier's instructions. Briefly, 10 ng of pcDNA3.1/Myc-His containing a PS108 insert are added to 50 $\mu$l of competent DH5 alpha cells, and the contents are mixed gently. The mixture is incubated on ice for 30 min, heat shocked for 20 sec at 37° C., and placed on ice for an additional 2 min. Upon addition of 0.95 ml of LB medium, the mixture is incubated for 1 h at 37° C. while shaking at 225 rpm. The transformed cells then are plated onto 100 mm LB/Amp (50 $\mu$g/ml ampicillin) plates and grown at 37° C. Colonies are picked and grown in 3 ml of LB/Amp broth. Plasmid DNA is purified using a QIAprep kit. The presence of the insert is confirmed using techniques known to those skilled in the art, including, but not limited to restriction digestion and gel analysis. (J. Sambrook et al., supra.)

B. Transfection of Human Embryonic Kidney Cell 293 Cells. The PS108 expression plasmid described in section A, supra, is retransformed into DH5 alpha cells, plated onto LB/ampicillin agar, and grown up in 10 ml of LB/ampicillin broth, as described hereinabove. The plasmid is purified using a QIAfilter™ Maxi kit (Qiagen, Chatsworth, Calif.) and is transfected into HEK293 cells (F. L. Graham et al., *J. Gen. Vir.* 36:59–72 (1977)). These cells are available from the A.T.C.C., 12301 Parklawn Drive, Rockville, Md. 20852, under Accession No. CRL 1573. Transfection is carried out using the cationic lipofectamine-mediated procedure described by P. Hawley-Nelson et al., Focus 15.73 (1993). Particularly, HEK293 cells are cultured in 10 ml DMEM media supplemented with 10% fetal bovine serum (FBS), L-glutamine (2 mM) and freshly seeded into 100 mm culture plates at a density of $9 \times 10^6$ cells per plate. The cells are grown at 37 ° C. to a confluency of between 70% and 80% for transfection. Eight micrograms (8 $\mu$g) of plasmid DNA are added to 800 $\mu$l of Opti-MEM I® medium (Gibco-BRL, Grand Island, N.Y.), and 48–96 $\mu$l of Lipofectamine™ Reagent (Gibco-BRL, Grand Island, N.Y.) are added to a second 800 $\mu$l portion of Opti-MEM I media. The two solutions are mixed and incubated at room temperature for 15–30 min. After the culture medium is removed from the cells, the cells are washed once with 10 ml of serum-free DMEM. The Opti-MEM I-Lipofectamine-plasmid DNA solution is diluted with 6.4 ml of serum-free DMEM and then overlaid onto the cells. The cells are incubated for 5 h at 37° C., after which time, an additional 8 ml of DMEM with 20% FBS are added. After 18–24 h, the old medium is aspirated, and the cells are overlaid with 5 ml of fresh DMEM with 5% FBS. Supernatants and cell extracts are analyzed for PS108 gene activity 72 h after transfection.

C. Analysis of Prostate Tissue Gene PS108 Antigen Expression. The culture supernatant, supra, is transferred to cryotubes and stored on ice. HEK293 cells are harvested by washing twice with 10 ml of cold Dulbecco's PBS and lysing by addition of 1.5 ml of CAT lysis buffer (Boehringer Mannheim, Indianapolis, Ind.), followed by incubation for 30 min at room temperature. Lysate is transferred to 1.7 ml polypropylene microfuge tubes and centrifuged at 1000×g for 10 min. The supernatant is transferred to new cryotubes and stored on ice. Aliquots of supernatants from the cells and the lysate of the cells expressing the PS108 protein construct are analyzed for the presence of recombinant PS108 protein. The aliquots can be run on SDS-polyacrylamide gel electrophoresis (SDS-PAGE) using standard methods and reagents known in the art. (J. Sambrook et al., supra). These gels can then be blotted onto a solid medium such as nitrocellulose, nytran, etc., and the PS108 protein band can be visualized using western blotting techniques with anti-myc epitope or anti-histidine monoclonal antibodies (Invitrogen, Carlsbad, Calif.) or anti-PS108 polyclonal serum (see Example 14). Alternatively, the expressed PS108 recombinant protein can be analyzed by mass spectrometry (see Example 12).

D. Purification. Purification of the PS108 recombinant protein containing the myc-his sequence is performed using the Xpress® affinity chromatography system (Invitrogen, Carlsbad, Calif.) containing a nickel-charged agarose resin which specifically binds polyhistidine residues. Supernatants from 10×100 mm plates, prepared as described supra, are pooled and passed over the nickel-charged column. Non-binding protein is eluted by washing the column with 50 mM Tris-HCl (pH 7.5)/150 mM NaCl buffer, leaving only the myc-his fusion proteins. Bound PS108 recombinant protein then is eluted from the column using either an excess of imidazole or histidine, or a low pH buffer. Alternatively, the recombinant protein can also be purified by binding at the myc-his sequence to an affinity column consisting of either anti-myc or anti-histidine monoclonal antibodies conjugated through a hydrazide or other linkage to an agarose resin and eluting with an excess of myc peptide or histidine, respectively.

The purified recombinant protein can then be covalently cross-linked to a solid phase, such as N-hydroxysuccinimide-activated sepharose columns (Pharmacia Biotech, Piscataway, N.J.), as directed by supplier's instructions. These columns containing covalently linked PS108 recombinant protein, can then be used to purify anti-PS108 antibodies from rabbit or mouse sera (see Examples 13 and 14).

E. Coating Microtiter Plates with PS108 Expressed Proteins. Supernatant from a 100 mm plate, as described supra, is diluted 1:3 in PBS. Then, 100 µl of the resulting mixture are placed into each well of a Reacti-Bind™ metal chelate microtiter plate (Pierce, Rockford, Ill.), incubated at room temperature while shaking, and is followed by four washes with deionized water. The prepared microtiter plate can then be used to screen polyclonal antisera for the presence of PS108 antibodies (see Example 17).

Although pcDNA3.1/Myc-His is utilized in this example, it is known to those skilled in the art that other comparable expression systems can be utilized herein with appropriate modifications in reagent and/or techniques and are within the skill of one of ordinary skill in the art. The largest cloned insert containing the coding region of the PS108 gene is sub-cloned into either (i) a eukaryotic expression vector which may contain, for example, a cytomegalovirus (CMV) promoter and/or protein fusible sequences which aid in protein expression and detection, or (ii) a bacterial expression vector containing a superoxide-dismutase (SOD) and CMP-KDO synthetase (CKS) or other protein fusion gene for expression of the protein sequence. Methods and vectors which are useful for the production of polypeptides which contain fusion sequences of SOD are described in published EPO application No. EP 0 196 056, published Oct. 1, 1986, which is incorporated herein by reference, and vectors containing fusion sequences of CKS are described in published EPO application No. EP 0 331 961, published Sep. 13, 1989, which publication is also incorporated herein by reference. The purified protein can be used in a variety of techniques, including, but not limited to animal immunization studies, solid phase immunoassays, etc.

Example 12

Chemical Analysis of Prostate Tissue Proteins

A. Analysis of Tryptic Peptide Fragments Using MS. Sera from patients with prostate disease, such as prostate cancer, sera from patients with no prostate disease, extracts of prostate tissues or cells from patients with prostate disease, such as prostate cancer, extracts of prostate tissues or cells from patients with no prostate disease, and extracts of tissues or cells from other non-diseased or diseased organs of patients, are run on a polyacrylamide gel using standard procedures and stained with Coomassie Blue. Sections of the gel suspected of containing the unknown polypeptide are excised and subjected to an in-gel reduction, acetamidation and tryptic digestion. P. Jeno et al, *Anal. Bio.* 224:451–455 (1995) and J. Rosenfeld et al, *Anal. Bio.* 203:173–179 (1992). The gel sections are washed with 100 mM $NH_4HCO_3$ and acetonitrile. The shrunken gel pieces are swollen in digestion buffer (50 mM $NH_4HCO_3$, 5 mM $CaCl_2$ and 12.5 µg/ml trypsin) at 4° C. for 45 min. The supernatant is aspirated and replaced with 5 to 10 µl of digestion buffer without trypsin and allowed to incubate overnight at 37° C. Peptides are extracted with 3 changes of 5% formic acid and acetonitrile and evaporated to dryness. The peptides are adsorbed to approximately 0.1 µl of POROS R2 sorbent (Perseptive Biosystems, Framingham, Mass.) trapped in the tip of a drawn gas chromatography capillary tube by dissolving them in 10 µl of 5% formic acid and passing it through the capillary. The adsorbed peptides are washed with water and eluted with 5% formic acid in 60% methanol. The eluant is passed directly into the spraying capillary of an API III mass spectrometer (Perkin-Elmer Sciex, Thornhill, Ontario, Canada) for analysis by nano-electrospray mass spectrometry. M. Wilm et al., *Int. J. Mass Spectrom. Ion Process* 136:167–180 (1994) and M. Wilm et al., *Anal. Chem.* 66:1–8 (1994). The masses of the tryptic peptides are determined from the mass spectrum obtained off the first quadrupole. Masses corresponding to predicted peptides can be further analyzed in MS/MS mode to give the amino acid sequence of the peptide.

B. Peptide Fragment Analysis Using LC/MS. The presence of polypeptides predicted from mRNA sequences found in hyperplastic disease tissues also can be confirmed using liquid chromatography/tandem mass spectrometry (LC/MS/MS). D. Hess et al., *METHODS. A Companion to Methods in Enzymology* 6:227–238 (1994). The serum specimen or tumor extract from the patient is denatured with SDS and reduced with dithiothreitol (1.5 mg/ml) for 30 min at 90° C. followed by alkylation with iodoacetamide (4 mg/ml) for 15 min at 25° C. Following acrylamide electrophoresis, the polypeptides are electroblotted to a cationic membrane and stained with Coomassie Blue. Following staining, the membranes are washed and sections thought to contain the unknown polypeptides are cut out and dissected into small pieces. The membranes are placed in 500 µl microcentrifuge tubes and immersed in 10 to 20 µl of proteolytic digestion buffer (100 mM Tris-HCl, pH 8.2, containing 0.1 M NaCl, 10% acetonitrile, 2 mM $CaCl_2$ and 5 µg/ml trypsin) (Sigma, St. Louis, Mo.). After 15 h at 37° C., 3 µl of saturated urea and 1 µl of 100 µg/ml trypsin are added and incubated for an additional 5 h at 37° C. The digestion mixture is acidified with 3 µl of 10% trifluoroacetic acid and centrifuged to separate supernatant from membrane. The supernatant is injected directly onto a microbore, reverse phase HPLC column and eluted with a linear gradient of acetonitrile in 0.05% trifluoroacetic acid. The eluate is fed directly into an electrospray mass spectrometer, after passing though a stream splitter if necessary to adjust the volume of material. The data is analyzed following the procedures set forth in Example 12, Section A.

Example 13

Gene Immunization Protocol

A. In Vivo Antigen Expression. Gene immunization circumvents protein purification steps by directly expressing an antigen in vivo after inoculation of the appropriate expression vector. Also, production of antigen by this method may allow correct protein folding and glycosylation since the protein is produced in mammalian tissue. The method utilizes insertion of the gene sequence into a plasmid which contains a CMV promoter, expansion and purification of the plasmid and injection of the plasmid DNA into the muscle tissue of an animal. Preferred animals include mice and rabbits. See, for example, H. Davis et al., *Human Molecular Genetics* 2:1847–1851 (1993). After one or two booster immunizations, the animal can then be bled, ascites fluid collected, or the animal's spleen can be harvested for production of hybridomas.

B. Plasmid Preparation and Purification. PS108 cDNA sequences are generated from the PS108 cDNA-containing vector using appropriate PCR primers containing suitable 5' restriction sites following the procedures described in Example 11. The PCR product is cut with appropriate restriction enzymes and inserted into a vector which contains the CMV promoter (for example, pRc/CMV or pcDNA3 vectors from Invitrogen, San Diego, Calif.). This plasmid then is expanded in the appropriate bacterial strain and purified from the cell lysate using a CsCl gradient or a Qiagen plasmid DNA purification column. All these techniques are familiar to one of ordinary skill in the art of molecular biology.

C. Immunization Protocol. Anesthetized animals are immunized intramuscularly with 0.1–100 µg of the purified plasmid diluted in PBS or other DNA uptake enhancers (Cardiotoxin, 25% sucrose). See, for example, H. Davis et al, *Human Gene Therapy* 4:733–740 (1993); and P. W. Wolff et al, *Biotechniques* 11:474–485 (1991). One to two booster injections are given at monthly intervals.

D. Testing and Use of Antiserum. Animals are bled and the resultant sera tested for antibody using peptides synthesized from the known gene sequence (see Example 16) using techniques known in the art, such as western blotting or EIA techniques. Antisera produced by this method can then be used to detect the presence of the antigen in a patient's tissue or cell extract or in a patient's serum by ELISA or Western blotting techniques, such as those described in Examples 15 through 18.

Example 14

Production of Antibodies Against PS108

A. Production of Polyclonal Antisera. Antiserum against PS108 was prepared by injecting rabbits with peptides whose sequences were derived from that of the predicted amino acid sequence (SEQUENCE ID NO 36) of the PS108 consensus nucleotide sequence. The synthesis of PS108 peptides (SEQUENCE ID NO 37, SEQUENCE ID NO 38, and SEQUENCE ID NO 39) is described in Example 10. Peptides used as immunogens were not conjugated to a carrier such as keyhole limpet hemocyanine, KLH, (i.e., they were unconjugated.).

Animal Immunization. Female white New Zealand rabbits weighing 2 kg or more were used for raising polyclonal antiserum. One animal was immunized per unconjugated peptide (SEQUENCE ID NO 37, SEQUENCE ID NO 38, and SEQUENCE ID NO 39). One week prior to the first immunization, 5 to 10 ml blood samples were obtained from each animal to serve as a non-immune prebleed sample.

The unconjugated PS108 peptides of SEQUENCE ID NO 37, SEQUENCE ID NO 38, and SEQUENCE ID NO 39, were used to prepare the primary immunogen by emulsifying 0.5 ml of the peptide at a concentration of 2 mg/ml in PBS (pH 7.2) which contained 0.5 ml of complete Freund's adjuvant (CFA) (Difco, Detroit, Mich.). The immunogen was injected into several sites of the animal via subcutaneous, intraperitoneal, and intramuscular routes of administration. Four weeks following the primary immunization, a booster immunization was administered. The immunogen used for the booster immunization dose was prepared by emulsifying 0.5 ml of the same unconjugated peptides used for the primary immunogen, except that the peptide now was diluted to 1 mg/ml with 0.5 ml of incomplete Freund's adjuvant (IFA) (Difco, Detroit, Mich.). Again, the booster dose was administered into several sites via subcutaneous, intraperitoneal and intramuscular types of injections. The animals were bled (5 ml) two weeks after the booster immunizations and each serum was tested for immunoreactivity to the peptide as described below. The booster and bleed schedules were repeated at 4 week intervals until an adequate titer was obtained. The titer or concentration of antiserum was determined by using unconjugated peptides in a microtiter EIA as described in Example 17, below. An antibody titer of 1:500 or greater was considered an adequate titer for further use and study.

TABLE 1

Titer of rabbit anti-PS108 peptide antisera (11 week bleed)

| Peptide Immunogen | Titer |
| --- | --- |
| SEQUENCE ID NO 37 | 250,000 |
| SEQUENCE ID NO 38 | 56,000 |
| SEQUENCE ID NO 39 | 53,000 |

B. Production of Monoclonal Antibody.

1. Immunization Protocol. Mice are immunized using peptides which can either be conjugated to a carrier such as KLH [prepared as described hereinbelow, or unconjugated (i.e., not conjugated to a carrier such as KLH)], except that the amount of the unconjugated or conjugated peptide for monoclonal antibody production in mice is one-tenth the amount used to produce polyclonal antisera in rabbits. Thus, the primary immunogen consists of 100 µg of unconjugated or conjugated peptide in 0.1 ml of CFA emulsion while the immunogen used for booster immunizations consists of 50 µg of unconjugated or conjugated peptide in 0.1 ml of IFA. Hybridomas for the generation of monoclonal antibodies are prepared and screened using standard techniques. The methods used for monoclonal antibody development follow procedures known in the art such as those detailed in Kohler and Milstein, *Nature* 256:494 (1975) and reviewed in J. G. R. Hurrel, ed., *Monoclonal Hybridoma Antibodies: Techniques and Applications,* CRC Press, Inc., Boca Raton, Fla. (1982). Another method of monoclonal antibody development which is based on the Kohler and Milstein method is that of L. T. Mimms et al., *Virology* 176:604–619 (1990), which is incorporated herein by reference.

The immunization regimen (per mouse) consists of a primary immunization with additional booster immunizations. The primary immunogen used for the primary immunization consists of 100 µg of unconjugated or conjugated peptide in 50 µl of PBS (pH 7.2) previously emulsified in 50 µl of CFA. Booster immunizations performed at approximately two weeks- and four weeks-post primary immunization consist of 50 µg of unconjugated or conjugated peptide in 50 µl of PBS (pH 7.2) emulsified with 50 µl IFA. A total of 100 µl of this immunogen are inoculated intraperitoneally and subcutaneously into each mouse. Individual mice are screened for immune response by microtiter plate enzyme immunoassay (EIA) as described in Example 17 approximately four weeks after the third immunization. Mice are inoculated either intravenously, intrasplenically or intraperitoneally with 50 μg of unconjugated or conjugated peptide in PBS (pH 7.2) approximately fifteen weeks after the third immunization.

Three days after this intravenous boost, splenocytes are fused with, for example, Sp2/0-Ag14 myeloma cells (Milstein Laboratories, England) using the polyethylene glycol (PEG) method. The fusions are cultured in Iscove's Modified Dulbecco's Medium (IMDM) containing 10% fetal calf serum (FCS), plus 1% hypoxanthine, aminopterin and thymidine (HAT). Bulk cultures are screened by microtiter plate EIA following the protocol in Example 17. Clones reactive with the peptide used as an immunogen and non-reactive with other peptides (i.e., peptides of PS108 not used as the immunogen) are selected for final expansion. Clones thus selected are expanded, aliquoted and frozen in IMDM containing 10% FCS and 10% dimethyl sulfoxide, (DMSO).

2. Peptide Conjugation. Peptide is conjugated to maleimide activated KLH (commercially available as Imject®, available from Pierce Chemical Company, Rockford, Ill.). Imject® contains about 250 moles of reactive maleimide groups per mole of hemocyanine. The activated KLH is dissolved in phosphate buffered saline (PBS, pH 8.4) at a concentration of about 7.7 mg/ml. The peptide is conjugated through cysteines occurring in the peptide sequence, or to a cysteine previously added, to the synthesized peptide in order to provide a point of attachment. The peptide is dissolved in DMSO (Sigma Chemical Company, St. Louis, Mo.) and reacted with the activated KLH at a mole ratio of about 1.5 moles of peptide per mole of reactive maleimide attached to the KLH. A procedure for the conjugation of peptide is provided hereinbelow. It is known to the ordinary artisan that the amounts, times and conditions of such a procedure can be varied to optimize peptide conjugation.

The conjugation reaction described hereinbelow is based on obtaining 3 mg of KLH peptide conjugate ("conjugated peptide"), which contains about 0.77 μmoles of reactive maleimide groups. This quantity of peptide conjugate usually is adequate for one primary injection and four booster injections for production of polyclonal antisera in a rabbit. Briefly, peptide is dissolved in DMSO at a concentration of 1.16 μmoles/100 μl of DMSO. One hundred microliters (100 μl) of the DMSO solution are added to 380 μl of the activated KLH solution prepared as described hereinabove, and 20 μl of PBS (pH 8.4) are added to bring the volume to 500 μl. The reaction is incubated overnight at room temperature with stirring. The extent of reaction is determined by measuring the amount of unreacted thiol in the reaction mixture. The difference between the starting concentration of thiol and the final concentration is assumed to be the concentration of peptide which has coupled to the activated KLH. The amount of remaining thiol is measured using Ellman's reagent (5,5'-dithiobis(2-nitrobenzoic acid), Pierce Chemical Company, Rockford, Ill.). Cysteine standards are made at a concentration of 0, 0.1, 0.5, 2, 5 and 20 mM by dissolving 35 mg of cysteine HCl (Pierce Chemical Company, Rockford, Ill.) in 10 ml of PBS (pH 7.2) and diluting the stock solution to the desired concentrations. The photometric determination of the concentration of thiol is accomplished by placing 200 μl of PBS (pH 8.4) in each well of an Immulon 2® microwell plate (Dynex Technologies, Chantilly, Va.). Next, 10 μl of standard or reaction mixture are added to each well. Finally, 20 μl of Ellman's reagent at a concentration of 1 mg/ml in PBS (pH 8.4) are added to each well. The wells are incubated for 10 minutes at room temperature, and the absorbance of all wells is read at 415 nm with a microplate reader (such as the BioRad Model 3550, BioRad, Richmond, Calif.). The absorbance of the standards is used to construct a standard curve and the thiol concentration of the reaction mixture is determined from the standard curve. A decrease in the concentration of free thiol is indicative of a successful conjugation reaction. Unreacted peptide is removed by dialysis against PBS (pH 7.2) at room temperature for 6 hours. The conjugate is stored at 2–8° C. if it is to be used immediately; otherwise, it is stored at –20° C. or colder.

3. Production of Ascites Fluid Containing Monoclonal Antibodies. Frozen hybridoma cells prepared as described hereinabove are thawed and placed into expansion culture. Viable hybridoma cells are inoculated intraperitoneally into Pristane treated mice. Ascitic fluid is removed from the mice, pooled, filtered through a 0.2μ filter and subjected to an immunoglobulin class G (IgG) analysis to determine the volume of the Protein A column required for the purification.

4. Purification of Monoclonal Antibodies From Ascites Fluid. Briefly, filtered and thawed ascites fluid is mixed with an equal volume of Protein A sepharose binding buffer (1.5 M glycine, 3.0 M NaCl, pH 8.9) and refiltered through a 0.2μ filter. The volume of the Protein A column is determined by the quantity of IgG present in the ascites fluid. The eluate then is dialyzed against PBS (pH 7.2) overnight at 2–8° C. The dialyzed monoclonal antibody is sterile filtered and dispensed in aliquots. The immunoreactivity of the purified monoclonal antibody is confirmed by determining its ability to specifically bind to the peptide used as the immunogen by use of the EIA microtiter plate assay procedure of Example 17. The specificity of the purified monoclonal antibody is confirmed by determining its lack of binding to irrelevant peptides such as peptides of PS108 not used as the immunogen. The purified anti-PS108 monoclonal thus prepared and characterized is placed at either 2–8° C. for short term storage or at –80° C. for long term storage.

5. Further Characterization of Monoclonal Antibody. The isotype and subtype of the monoclonal antibody produced as described hereinabove can be determined using commercially available kits (available from Amersham. Inc., Arlington Heights, Ill.). Stability testing also can be performed on the monoclonal antibody by placing an aliquot of the monoclonal antibody in continuous storage at 2–8° C. and assaying optical density (OD) readings throughout the course of a given period of time.

C. Use of Recombinant Proteins as immunogens. It is within the scope of the present invention that recombinant proteins made as described herein can be utilized as immunogens in the production of polyclonal and monoclonal antibodies, with corresponding changes in reagents and techniques known to those skilled in the art.

Example 15

Purification of Serum Antibodies Which Specifically Bind to PS108 Peptides

Immune sera, obtained as described hereinabove in Examples 13 and/or 14, is affinity purified using immobilized synthetic peptides prepared as described in Example 10, or recombinant proteins prepared as described in Example 11. An IgG fraction of the antiserum is obtained by passing the diluted, crude antiserum over a Protein A column (Affi-Gel protein A, Bio-Rad, Hercules, Calif.). Elution with a buffer (Binding Buffer, supplied by the manufacturer)

removes substantially all proteins that are not immunoglobulins. Elution with 0.1 M buffered glycine (pH 3) gives an immunoglobulin preparation that is substantially free of albumin and other serum proteins.

Immunoaffinity chromatography is performed to obtain a preparation with a higher fraction of specific antigen-binding antibody. The peptide used to raise the antiserum is immobilized on a chromatography resin, and the specific antibodies directed against its epitopes are adsorbed to the resin. After washing away non-binding components, the specific antibodies are eluted with 0.1 M glycine buffer, pH 2.3. Antibody fractions are immediately neutralized with 1.0 M Tris buffer (pH 8.0) to preserve immunoreactivity. The chromatography resin chosen depends on the reactive groups present in the peptide. If the peptide has an amino group, a resin such as Affi-Gel 10 or Affi-Gel 15 is used (Bio-Rad, Hercules, Calif.). If coupling through a carboxy group on the peptide is desired, Affi-Gel 102 can be used (Bio-Rad, Hercules, Calif.). If the peptide has a free sulf-hydryl group, an organomercurial resin such as Affi-Gel 501 can be used (Bio-Rad, Hercules, Calif.).

Alternatively, spleens can be harvested and used in the production of hybridomas to produce monoclonal antibodies following routine methods known in the art as described hereinabove.

Example 16

Western Blotting of Tissue Samples

Protein extracts were prepared by homogenizing tissue samples in 0.1 M Tris-HCl (pH 7.5), 15% (w/v) glycerol, 0.2 mM EDTA, 1.0 mM 1,4-dithiothreitol, 10 μg/ml leupeptin and 1.0 mM phenylmethylsulfonylfluoride (S. R. Kain et al., *Biotechniques* 17:982 (1994). Following homogenization, the homogenates were centrifuged at 4° C. for 5 minutes to separate supernatant from debris. For protein quantitation, 3–10 μl of supernatant were added to 1.5 ml of bicinchoninic acid reagent (Sigma, St. Louis, Mo.), and the resulting absorbance at 562 nm were measured.

For SDS-PAGE, samples were adjusted to desired protein concentration with Tricine Buffer (Novex, San Diego, Calif.), mixed with an equal volume of 2×Tricine sample buffer (Novex, San Diego, Calif.), and heated for 5 minutes at 100° C. in a thermal cycler. Samples were then applied to a Novex 10–20% Precast Tricine Gel for electrophoresis. Following electrophoresis, samples were transferred from the gels to nitrocellulose membranes in Novex Tris-Glycine Transfer buffer. Membranes were then probed with specific anti-peptide antibodies using the reagents and procedures provided in the Western Lights Plus or Western Lights (Tropix, Bedford, Mass.) chemiluminescence detection kits. Chemiluminescent bands were visualized by exposing the developed membranes to Hyperfilm ECL (Amersham, Arlington Heights, Ill.).

Figure 4:
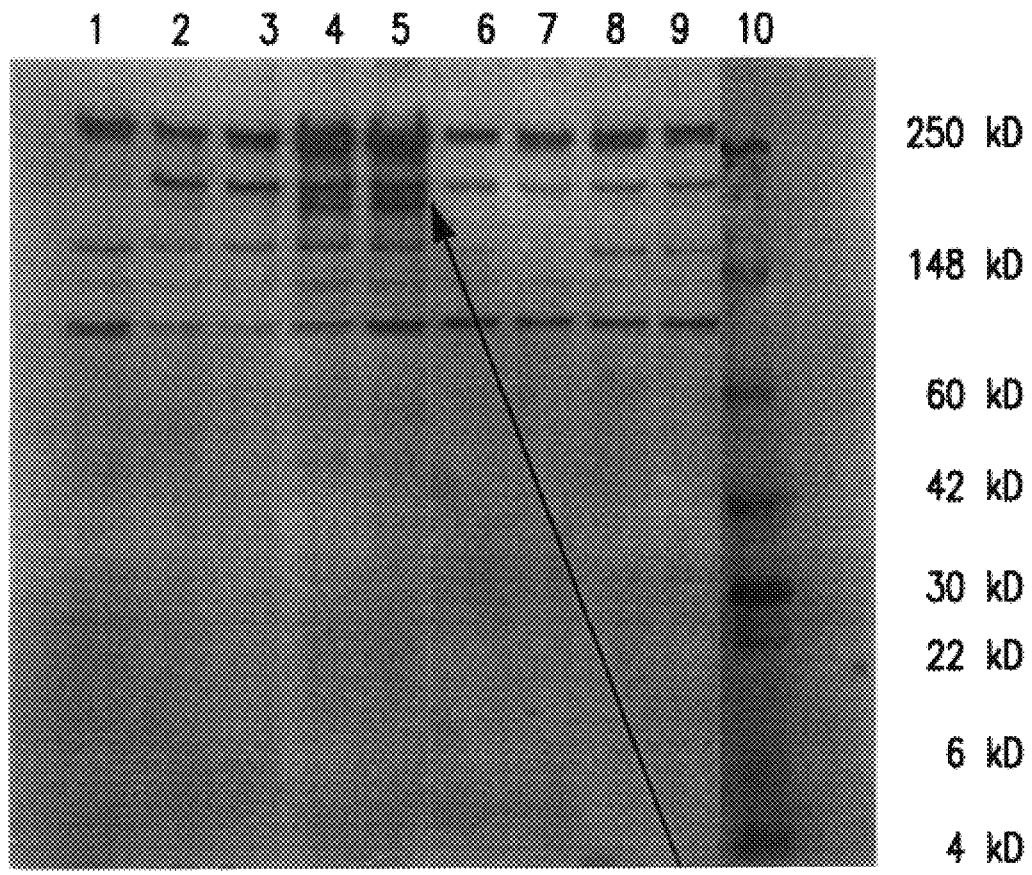
FIG. 4 shows the results of a Western blot performed on a panel of tissue protein extracts detected with antiserum against the PS108 synthetic peptide of SEQUENCE ID NO 37.

FIG. 4 shows the results of the Western blot performed on a panel of tissue extracts using antiserum prepared against the PS108 peptide of SEQUENCE ID NO 37 (see Example 14). Each lane of FIG. 4 represents a different tissue protein extract: (1) colon cancer; (2–4) BPH; (5) prostate cancer; (6 and 7) lung; (8 and 9) breast cancer; and (10) markers. A band above 200 kD (identified by the arrow in FIG. 4), as determined by protein size markers (lane 10), was detected in the prostate cancer tissue extract (lane 5) and one of the three BPH tissue extracts (lane 4).

Competition experiments were performed in an analogous manner as above with the following exception: the primary antibodies (anti-peptide polyclonal antisera) were pre-incubated overnight at 4° C. with varying concentrations of peptide immunogen prior to exposure to the nitrocellulose filter. Development of the Western was continued as above. Antibody binding to the band above 200 kD was inhibited at a concentration of 2.09 μM of the synthetic peptide (SEQUENCE ID NO 37).

After visualization of the bands on film, the bands were also visualized directly on the membranes by the addition and development of chromogenic substrate 5-bromo-4-chloro-3-indolyl phosphate (BCIP). This chromogenic solution contained 0.016% BCIP in a solution containing 100 mM NaCl, 5 mM $MgCl_2$ and 100 mM Tris-HCl, pH 9.5. The filter was incubated in the solution at room temperature until the bands developed to the desired intensity. An image was generated by transillumination of the blot on an Alpha Innotech Corporation (San Leandro, Calif.) lightbox and captured with an Alpha Imager 2000 Documentation and Analysis system. Molecular mass determination was made based upon the mobility of pre-stained molecular weight standards (Novex, San Diego, Calif.) and biotinylated molecular weight standards (Tropix, Bedford, Mass.).

Example 17

EIA Microtiter Plate Assay

The immunoreactivity of antiserum obtained from rabbits as described in Example 14 was determined by means of a microtiter plate EIA, as follows. Briefly, synthetic peptides, SEQUENCE ID NO 37, SEQUENCE ID NO 38, and SEQUENCE ID NO 39, prepared as described in Example 10, were dissolved in carbonate buffer (50 mM, pH 9.6) to a final concentration of 2 μg/ml. Next, 100 μl of the peptide or protein solution were placed in each well of an Immulon 2® microtiter plate (Dynex Technologies, Chantilly, Va.). The plate was incubated overnight at room temperature and then washed four times with deionized water. The wells were blocked by adding 125 μl of a suitable protein blocking agent, such as Superblock® (Pierce Chemical Company, Rockford, Ill.), to each well and then immediately discarding the solution. This blocking procedure was performed three times. Antiserum obtained from immunized rabbits or mice, prepared as previously described, was diluted in a protein blocking agent (e.g., a 3% Superblock® solution) in PBS containing 0.05% Tween-20® (monolaurate polyoxyethylene ether) (Sigma Chemical Company, St. Louis, Mo.) and 0.05% sodium azide at dilutions of 1:100, 1:500, 1:2500, 1:12,500, and 1:62,500 and placed in each well of the coated microtiter plate. The wells then were incubated for three hours at room temperature. Each well was washed four times with deionized water. One hundred microliters of alkaline phosphatase-conjugated goat anti-rabbit IgG or goat anti-mouse IgG antiserum (Southern Biotech, Birmingham, Ala.) diluted 1:2000 in 3% Superblock® solution in phosphate buffered saline containing 0.05% Tween 20® and 0.05% sodium azide, were added to each well. The wells were incubated for two hours at room temperature. Next, each well was washed four times with deionized water. One hundred microliters of paranitrophenyl phosphate substrate (Kirkegaard and Perry Laboratories, Gaithersburg, Md.) then were added to each well. The wells were incubated for thirty minutes at room temperature. The absorbance at 405 nm was read in each well. Positive reactions were identified by an increase in absorbance at 405 nm in the test well above that absorbance given by a non-immune serum (negative control). A positive reaction was indicative of the presence of detectable anti-PS108 antibodies. Titers of the anti-peptide antisera were calculated from the previously described dilutions of antisera and defined as the calculated dilution, where $A_{405nm}$=0.5 OD.

Example 18

Coating of Solid Phase Particles

A. Coating of Microparticles with Antibodies Which Specifically Bind to PS108 Antigen. Affinity purified antibodies which specifically bind to PS108 protein (see Example 15) are coated onto microparticles of polystyrene, carboxylated polystyrene, polymethylacrylate or similar particles having a radius in the range of about 0.1 to 20 μm. Microparticles may be either passively or actively coated. One coating method comprises coating EDAC (1-(3-dimethylaminopropyl)-3-ethylcarbodiimide hydrochloride (Aldrich Chemical Co., Milwaukee, Wis.) activated carboxylated latex microparticles with antibodies which specifically bind to PS108 protein, as follows. Briefly, a final 0.375% solid suspension of resin washed carboxylated latex microparticles (available from Bangs Laboratories, Carmel, Ind. or Serodyn, Indianapolis, Ind.) are mixed in a solution containing 50 mM MES buffer, pH 4.0 and 150 μg/ml of affinity purified anti-PS108 antibody (see Example 14) for 15 min in an appropriate container. EDAC coupling agent is added to a final concentration of 5.5 μg/ml to the mixture and mixed for 2.5 h at room temperature.

The microparticles then are washed with 8 volumes of a Tween 20®/sodium phosphate wash buffer (pH 7.2) by tangential flow filtration using a 0.2 μm Microgon Filtration module. Washed microparticles are stored in an appropriate buffer which usually contains a dilute surfactant and irrelevant protein as a blocking agent, until needed.

B. Coating of ¼ Inch Beads. Antibodies which specifically bind to PS108-antigen also may be coated on the surface of ¼ inch polystyrene beads by routine methods known in the art (Snitman et al, U.S. Pat. No. 5,273,882, incorporated herein by reference) and used in competitive binding or EIA sandwich assays.

Polystyrene beads first are cleaned by ultrasonicating them for about 15 seconds in 10 mM $NaHCO_3$ buffer at pH 8.0. The beads then are washed in deionized water until all fines are removed. Beads then are immersed in an antibody solution in 10 mM carbonate buffer, pH 8 to 9.5. The antibody solution can be as dilute as 1 μg/ml in the case of high affinity monoclonal antibodies or as concentrated as about 500 μg/ml for polyclonal antibodies which have not been affinity purified. Beads are coated for at least 12 hours at room temperature, and then they are washed with deionized water. Beads may be air dried or stored wet (in PBS, pH 7.4). They also may be overcoated with protein stabilizers (such as sucrose) or protein blocking agents used as non-specific binding blockers (such as irrelevant proteins, Carnation skim milk, Superblock®, or the like).

Example 19

Microparticle Enzyme Immunoassay (MEIA)

PS108 antigens are detected in patient test samples by performing a standard antigen competition EIA or antibody sandwich EIA and utilizing a solid phase such as microparticles (MEIA). The assay can be performed on an automated analyzer such as the IMx® Analyzer (Abbott Laboratories, Abbott Park, Ill.).

A. Antibody Sandwich EIA. Briefly, samples suspected of containing PS108 antigen are incubated in the presence of anti-PS108 antibody-coated microparticles (prepared as described in Example 17) in order to form antigen/antibody complexes. The microparticles then are washed and an indicator reagent comprising an antibody conjugated to a signal generating compound (i.e., enzymes such as alkaline phosphatase or horseradish peroxidase) is added to the antigen/antibody complexes or the microparticles and incubated. The microparticles are washed and the bound antibody/antigen/antibody complexes are detected by adding a substrate (e.g., 4-methyl umbelliferyl phosphate (MUP), or OPD/peroxide, respectively), that reacts with the signal generating compound to generate a measurable signal. An elevated signal in the test sample, compared to the signal generated by a negative control, detects the presence of PS108 antigen. The presence of PS108 antigen in the test sample is indicative of a diagnosis of a prostate disease or condition, such as prostate cancer.

B. Competitive Binding Assay. The competitive binding assay uses a peptide or protein that generates a measurable signal when the labeled peptide is contacted with an anti-peptide antibody coated microparticle. This assay can be performed on the IMx® Analyzer (available from Abbott Laboratories, Abbott Park, Ill.). The labeled peptide is added to the PS108 antibody-coated microparticles (prepared as described in Example 17) in the presence of a test sample suspected of containing PS108 antigen, and incubated for a time and under conditions sufficient to form labeled PS108 peptide (or labeled protein)/bound antibody complexes and/or patient PS108 antigen/bound antibody complexes. The PS108 antigen in the test sample competes with the labeled PS108 peptide (or PS108 protein) for binding sites on the microparticle. PS108 antigen in the test sample results in a lowered binding of labeled peptide and antibody coated microparticles in the assay since antigen in the test sample and the PS108 peptide or PS108 protein compete for antibody binding sites. A lowered signal (compared to a control) indicates the presence of PS108 antigen in the test sample. The presence of PS108 antigen suggests the diagnosis of a prostate disease or condition, such as prostate cancer.

The PS108 polynucleotides and the proteins encoded thereby which are provided and discussed hereinabove are useful as markers of prostate tissue disease, especially prostate cancer. Tests based upon the appearance of this marker in a test sample such as blood, plasma or serum can provide low cost, non-invasive, diagnostic information to aid the physician to make a diagnosis of cancer, to help select a therapy protocol, or to monitor the success of a chosen therapy. This marker may appear in readily accessible body fluids such as blood, urine or stool as antigens derived from the diseased tissue which are detectable by immunological methods. This marker may be elevated in a disease state, altered in a disease state, or be a normal protein of the prostate which appears in an inappropriate body compartment.

Example 20

Immunohistochemical Detection of PS108 Protein

Antiserum against the PS108 peptide of SEQUENCE ID NO 37, prepared as described in Example 14, supra, was used to immunohistochemically stain a variety of normal and diseased tissues using standard procedures. Briefly, frozen blocks of tissue were cut into 6 micron sections, and placed on microscope slides. After fixation in cold acetone, the sections were dried at room temperature, then washed with phosphate buffered saline and blocked. The slides were incubated with the peptide of SEQUENCE ID NO 37 at a dilution of 1 to 500, washed, incubated with biotinylated goat anti-rabbit antibody, washed again, and incubated with avidin labeled with horse radish peroxidase. After a final wash, the slides were incubated with 3-amino-9-ethylcarbazole substrate which gives a red stain. The slides were counterstained with hematoxylin, mounted, and examined under a microscope by a pathologist.

Anti-PS108 antibody gives intense cytoplasmic immunoreactivity in the epithelium of all prostate specimens (benign and malignant). Secretory cells of benign glands showed strongest immunoreactivity in the supranuclear cytoplasm. Basal cells and atrophic glands were virtually all negative. Cancer cells showed more extensive immunoreactivity compared to benign epithelium. High grade prostate cancer showed extensive and intense immunoreactivity. There was almost no background staining in the stroma. For all other tissue specimens (colon, lung, liver, bladder, and breast) the immunoreactivity was weak and equivocal.

Results of all tissues examined are tabulated in Table 2. The column labeled "#pos/total" refers to the number of specimens positive out of the total number of specimens. The column labeled "%" reports the percent of cells which are positive averaged over all tissues examined.

TABLE 2

Tissue Staining by Anti-PS108

| TISSUE | #POS/ TOTAL | % | COMMENTS |
| --- | --- | --- | --- |
| Colon, normal | 4/4 | 53 | Weak immunoreactivity only on superficial cells. Equivocal in one case. |
| Colon, cancer | 3/3 | 37 | Weak immunoreactivity. Patchy in one case. |
| Lung, normal | 0/4 | 0 | Weak immunoreactivity in 10% of minor salivary glands in one case. |
| Lung, bronchial epithelium | 0/4 | 0 | No immunoreactive cells |
| Liver, normal hepatocytes | 0/2 | 0 | Intracytoplasmic background |
| Liver, normal bile duct epithelium | 0/2 | 0 | |
| Bladder, normal epithelium | 2/3 | 10 | Weak, equivocal immunoreactivity only on superficial urothelial cells. |
| Bladder, normal wall | 0/5 | 0 | Smooth muscle cells negative. |
| Breast, benign tissue | 2/2 | 90 | Weak, cytoplasmic immunoreactivity |
| Breast, fibrocystic changes | 1/1 | 60 | Weak, equivocal epithelial immunoreactivity |
| Prostate, benign | 16/16 | 66 | Intense, granular, supranuclear cytoplasmic immunoreactivity of secretory cells. |
| Prostate, cancer | 15/15 | 87 | Intense cytoplasmic immunoreactivity in cancer cells. High grade cancer shows extensive and intense immunoreactivity |

We claim:

1. A polypeptide with an amino acid sequence selected from the group consisting of SEQUENCE ID NO 36; SEQUENCE ID NO 37; SEQUENCE ID NO 38; SEQUENCE ID NO 39.

2. The polypeptide of claim 1, wherein said polypeptide is produced by recombinant techniques.

3. The polypeptide of claim 1, wherein said polypeptide is produced by synthetic techniques.

4. An antibody which specifically binds to at least one epitope, wherein said epitope has an amino acid sequence selected from the group consisting of SEQUENCE ID NO 36, SEQUENCE ID NO 37, SEQUENCE ID NO 38, SEQUENCE ID NO 39.

5. An assay kit for determining the presence of an antigen or antibody in a test sample, said assay kit comprising a container containing a polypeptide having an amino acid sequence selected from the group consisting of SEQUENCE ID NO 36, SEQUENCE ID NO 37, SEQUENCE ID NO 38, SEQUENCE ID NO 39.

6. The assay kit of claim 5, wherein said polypeptide is attached to a solid phase.

7. The assay kit of claim 5 further comprising a container with tools useful for collection of said sample, wherein the tools are selected from the group consisting of lancets, absorbent paper, cloth, swabs and cups.

8. The test kit of claim 5 further comprising a container with tools useful for collection of said sample, wherein the tools are selected from the group consisting of lancets, absorbent paper, cloth, swabs and cups.

* * * * *

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
      (A) LENGTH: 258 base pairs
      (B) TYPE: nucleic acid
      (C) STRANDEDNESS: single
      (D) TOPOLOGY: linear (xi) SEQUENCE DESCRIPTION: SEQ ID NO:1:

```
GGGGCTGTAC CAGGGCGTGC CCAGAGCTGA GCCGGGCACC GAGGCCCGGA GACACTATGA      60

TGAAGGCGTT CGGATGGGCA GCCTGGGGCT GTTCCTGCAG TGCGCCATCT CCCTGGTCTT     120

CTCTCTGGTC ATGGACCGGC TGGTGCAGCG ATTCGGCACT CGAGCAGTCT ATTTGGCCAG     180

TGTGGCAGCT TTCCCTGTGG CTGCCGGTGC CACATGCCTG TCCCACAGTG TGGCCGTGGT     240

GACAGCTTCA GCCGCCTT                                                   258
```

(2) INFORMATION FOR SEQ ID NO:2:

(i) SEQUENCE CHARACTERISTICS:
      (A) LENGTH: 217 base pairs
      (B) TYPE: nucleic acid
      (C) STRANDEDNESS: single
      (D) TOPOLOGY: linear (xi) SEQUENCE DESCRIPTION: SEQ ID NO:2:

```
ACCAGGGCGT GCCCAGAGCT GAGCCGGGCA CCGAGGCCCG GAGACACTAT GATGAAGGCG      60

TTCGGATGGG CAGCCTGGGG CTGTTCCTGC AGTGCGCCAT CTCCCTGGTC TTCTCTCTGG     120

TCATGGACCG GCTGGTGCAG CGATTCGGCA CTCGAGCAGT CTATTTGGCC AGTGTGGCAG     180

CTTTCCCTGT GGCTGCCGGT GCCACATGCC TGTCCCA                              217
```

(2) INFORMATION FOR SEQ ID NO:3:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 215
        (D) OTHER INFORMATION: /note= " N' represents an A or G or
           T or C polymorphism at this position"

(xi) SEQUENCE DESCRIPTION: SEQ ID NO:3:

```
GACAGCTTCA GCCGCCCTCA CCGGGTTCAC CTTCTCAGCC CTGCAGATCC TGCCCTACAC      60

ACTGGCCTCC CTCTACCACC GGGAGAAGCA GGTGTTCCTG CCCAAATACC GAGGGGACAC     120

TGGAGGTGCT AGCAGTGAGG ACAGCCTGAT GACCAGCTTC CTGCCAGGCC CTAAGCCTGG     180

AGCTCCCTTC CCTAATGGAC ACGTGGGTGC TGGANGCAGT GGCCTGCTCC CACCTCCACC     240

CGCGCTCTGC GGGGC                                                      255
```

(2) INFORMATION FOR SEQ ID NO:4:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (xi) SEQUENCE DESCRIPTION: SEQ ID NO:4:

```
GCTCCCTTCC CTAATGGACA CGTGGGTGCT GGAGGCAGTG GCCTGCTCCC ACCTCCACCC      60

GCGCTCTGCG GGGCCTCTGC CTGTGATGTC TCCGTACGTG TGGTGGTGGG TGAGCCCACC     120

GAGGCCAGGG TGGTTCCGGG CCGGGGCATC TGCCTGGACC TCGCCATCCT GGATAGTGCC     180

TTCCTGCTGT CCCAGGTGGC CCCATCCCTG TTTATGGGCT CCATTGTCCA GCTCAGCCAG     240

TCTGTCA                                                               247
```

(2) INFORMATION FOR SEQ ID NO:5:

(i) SEQUENCE CHARACTERISTICS:
        (A) LENGTH: 231 base pairs
        (B) TYPE: nucleic acid
        (C) STRANDEDNESS: single
        (D) TOPOLOGY: linear (xi) SEQUENCE DESCRIPTION: SEQ ID NO:5:

```
TGGATAGTGC CTTCCTGCTG TCCCAGGTGG CCCCATCCCT GTTTATGGGC TCCATTGTCC      60

AGCTCAGCCA GTCTGTCACT GCCTATATGG TGTCTGCCGC AGGCTGGGTC TGGTCGCCAT     120

TTACTTTGCT ACACAGGTAG TATTTGACAA GAGCGACTTG GCCAAATACT CAGCGTAGAA     180

AACTTCCAGC ACATTGGGGT GGAGGGCCTG CCTCACTGGG TCCCAGCTCC C              231
```

(2) INFORMATION FOR SEQ ID NO:6:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 178
        (D) OTHER INFORMATION: /note= " N' represents an A or G or
            T or C polymorphism at this position"

(xi) SEQUENCE DESCRIPTION: SEQ ID NO:6:

```
CTTGGCCAAA TACTCAGCGT AGAAAACTTC CAGCACATTG GGGTGGAGGG CCTGCCTCAC      60

TGGGTCCCAG CTCCCCGCTC CTGTTAGCCC CATGGGGCTG CCGGGCTGGC CGCCAGTTTC     120

TGTTGCTGCC AAAGTAATGT GGCTCTCTGC TGCCACCCTG TGCTGCTGAG GTGCGTANTG     180

CACAGCTGGG GGCTG                                                      195
```

(2) INFORMATION FOR SEQ ID NO:7:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 67
        (D) OTHER INFORMATION: /note= " N' represents an A or G or
            T or C polymorphism at this position"

(ix) FEATURE:
        (A) NAME/KEY: base_polymorphism
        (B) LOCATION: 222
        (D) OTHER INFORMATION: /note= " N' represents an A or G or
            T or C polymorphism at this position"

(xi) SEQUENCE DESCRIPTION: SEQ ID NO:7:

```
GCCAGTTTCT GTTGCTGCCA AAGTAATGTG GCTCTCTGCT GCCACCCTGT GCTGCTGAGG      60

TGCGTANTGC ACAGCTGGGG GCTGGGGCGT CCCTCTCCTC TCTCCCCAGT CTCTAGGGCT     120

GCCTGACTGG AGGCCTTCCA AGGGGGTTTC AGTCTGGACT TATACAGGGA GGCCAGAAGG     180

GCTCCATGCA CTGGAATGCG GGACTCTGC AGGTGGATTA CNC                        223
```

(2) INFORMATION FOR SEQ ID NO:8:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 323
        (D) OTHER INFORMATION: /note= " N' represents an A or G or
            T or C polymorphism at this position"

(xi) SEQUENCE DESCRIPTION: SEQ ID NO:8:

```
GCCAGAAGGG CTCCATGCAC TGGAATGCGG GGACTCTGCA GGTGGATTAC CCAGGCTCAG      60

GGTTAACAGC TAGCCTCCTA GTTGAGACAC ACCTAGAGAA GGGTTTTTGG GAGCTGAATA     120

AACTCAGTCA CCTGGTTTCC CATCTCTAAG CCCCTTAACC TGCAGCTTCG TTTAATGTAG     180

CTCTTGCATG GGAGTTTCTA GGATGAAACA CTCCTCCATG GGATTTGAAC ATATGAAAGT     240
```

TATTTGTAGG GGAAGAGTCC TGAGGGGCAA CACACAAGAA CCAGGTCCCC TCAGCCCACA        300

GCACTGTCTT TTTGCTGATC CANCCCCCTC TTACTTTTAT CA                          342

(2) INFORMATION FOR SEQ ID NO:9:

(i) SEQUENCE CHARACTERISTICS:
        (A) LENGTH: 265 base pairs
        (B) TYPE: nucleic acid
        (C) STRANDEDNESS: single
        (D) TOPOLOGY: linear (xi) SEQUENCE DESCRIPTION: SEQ ID NO:9:

GGGGAAGAGT CCTGAGGGGC AACACACAAG AACCAGGTCC CCTCAGCCCA CAGCACTGTC        60

TTTTTGCTGA TCCACCCCCC TCTTACCTTT TATCAGGATG TGGCCTGTTG GTCCTTCTGT       120

TGCCATCACA GAGACACAGG CATTTAAATA TTTAACTTAT TTATTTAACA AAGTAGAAGG       180

GAATCCATTG CTAGCTTTTC TGTGTTGGTG TCTAATATTT GGGTAGGGTG GGGGATCCCC       240

AACAATCAGG TCCCCTGAGA TAGCT                                            265

(2) INFORMATION FOR SEQ ID NO:10:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 147
        (D) OTHER INFORMATION: /note= " N' represents an A or G or
            T or C polymorphism at this position"

(xi) SEQUENCE DESCRIPTION: SEQ ID NO:10:

CTCTTACCTT TTATCAGGAT GTGGCCTGTT GGTCCTTCTG TTGCCATCAC AGAGACACAG        60

GCATTTAAAT ATTTAACTTA TTTATTTAAC AAAGTAGAAG GGAATCCATT GCTAGCTTTT       120

CTGTGTTGGT GTCTAATATT TGGGTANGGT GGGGGATCCC CAACAATCAG GTCCCCTGAG       180

ATAGCTGGTC ATTGGGCTGA TCATTGCCAG AATCTTCTTC TCCTGGGGTC TGGCCCCCCA       240

AAATGCCTAA CCCAGGACCT TGGAAATTCT ACTCATCCCA AATGATAA                   288

(2) INFORMATION FOR SEQ ID NO:11:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 216
        (D) OTHER INFORMATION: /note= " N' represents an A or G or
            T or C polymorphism at this position"

(xi) SEQUENCE DESCRIPTION: SEQ ID NO:11:

AAATTCTACT CATCCCAAAT GATAATTCCA AATGCTGTTA CCCAAGGTTA GGGTGTTGAA        60

GGAAGGTAGA GGGTGGGGCT TCAGGTCTCA ACGGCTTCCC TAACCACCCC TCTTCTCTTG       120

GCCCAGCCTG GTTCCCCCCA CTTCCACTCC CCTCTACTCT CTCTAGGACT GGGCTGATGA       180

AGGCACTGCC CAAAATTTCC CCTACCCCCA ACTTTNCCCT ACCCCCAACT TTCCCCACCA       240

GCTCCACAAC CCTGTTTGGA GCTACTGCAG GT                                    272

(2) INFORMATION FOR SEQ ID NO:12:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 18
        (D) OTHER INFORMATION: /note= " N' represents an A or G or
            T or C polymorphism at this position"

(ix) FEATURE:
        (A) NAME/KEY: base_polymorphism
        (B) LOCATION: 19
        (D) OTHER INFORMATION: /note= " N' represents an A or G or
            T or C polymorphism at this position"

(ix) FEATURE:
        (A) NAME/KEY: base_polymorphism
        (B) LOCATION: 197
        (D) OTHER INFORMATION: /note= " N' represents an A or G or
            T or C polymorphism at this position"

(xi) SEQUENCE DESCRIPTION: SEQ ID NO:12:

```
AAGGCACTGC CCAAAATNNC CCCTACCCCC AACTTTCCCC TACCCCCAAC TTTCCCCACC      60

AGCTCCACAA CCCTGTTTGG AGCTACTGCA GGACCAGAAG CACAAAGTGC GGTTTCCCAA     120

GCCTTTGTCC ATCTCAGCCC CCAGAGTATA TCTGTGCTTG GGGAATCTCA CACAGAAACT    180

CAGGAGCACC CCCTGCNTGA GCTAAGGGAG GTCTTATCTC TCAGGGGGGG TTTAAGTGCC    240

GTTTGCAATA ATGTCGTCTT ATTTATTTAG CGGGGTGAAT ATTTTATACT GTAA           294
```

(2) INFORMATION FOR SEQ ID NO:13:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 113
        (D) OTHER INFORMATION: /note= " N' represents an A or G or
            T or C polymorphism at this position"

(ix) FEATURE:
        (A) NAME/KEY: base_polymorphism
        (B) LOCATION: 147
        (D) OTHER INFORMATION: /note= " N' represents an A or G or
            T or C polymorphism at this position"

(xi) SEQUENCE DESCRIPTION: SEQ ID NO:13:

```
CTCCACAACC CTGTTTGGAG CTACTGCAGG ACCAGAAGCA CAAAGTGCGG TTTCCCAAGC      60

CTTTGTCCAT CTCAGCCCCC AGAGTATATC TGTGCTTGGG GAATCTCACA CANAAACTCA    120

GGAGCACCCC CTGCCTGAGC TAAGGGNGGT C                                    151
```

(2) INFORMATION FOR SEQ ID NO:14:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (xi) SEQUENCE DESCRIPTION: SEQ ID NO:14:

```
CCCAGAGTAT ATCTGTGCTT GGGGAATCTC ACACAGAAAC TCAGGAGCAC CCCCTGCCTG      60

AGCTAAGGGA GGTCTTATCT CTCAGGGGGG GTTTAAGTGC CGTTTGCAAT AATGTCGTCT     120

TATTTATTTA GCGGGGTGAA TATTTTATAC TGTAAGTGAG CAATCAGAGT ATAATGTTTA     180

TGGTGACAAA ATTAAAGGCT TTCTTATATG TTT                                  213
```

(2) INFORMATION FOR SEQ ID NO:15:

(i) SEQUENCE CHARACTERISTICS:
        (A) LENGTH: 2143 base pairs
        (B) TYPE: nucleic acid
        (C) STRANDEDNESS: single
        (D) TOPOLOGY: linear (xi) SEQUENCE DESCRIPTION: SEQ ID NO:15:

```
ACCAGGGCGT GCCCAGAGCT GAGCCGGGCA CCGAGGCCCG GAGACACTAT GATGAAGGCG      60

TTCGGATGGG CAGCCTGGGG CTGTTCCTGC AGTGCGCCAT CTCCCTGGTC TTCTCTCTGG     120

TCATGGACCG GCTGGTGCAG CGATTCGGCA CTCGAGCAGT CTATTTGGCC AGTGTGGCAG     180

CTTTCCCTGT GGCTGCCGGT GCCACATGCC TGTCCCACAG TGTGGCCGTG GTGACAGCTT     240

CAGCCGCCCT CACCGGGTTC ACCTTCTCAG CCCTGCAGAT CCTGCCCTAC ACACTGGCCT     300

CCCTCTACCA CCGGGAGAAG CAGGTGTTCC TGCCCAAATA CCGAGGGGAC ACTGGAGGTG     360

CTAGCAGTGA GGACAGCCTG ATGACCAGCT TCCTGCCAGG CCCTAAGCCT GGAGCTCCCT     420

TCCCTAATGG ACACGTGGGT GCTGGAGGCA GTGGCCTGCT CCCACCTCCA CCCGCGCTCT     480

GCGGGGCCTC TGCCTGTGAT GTCTCCGTAC GTGTGGTGGT GGGTGAGCCC ACCGAGGCCA     540

GGGTGGTTCC GGGCCGGGGC ATCTGCCTGG ACCTCGCCAT CCTGGATAGT GCCTTCCTGC     600

TGTCCCAGGT GGCCCCATCC CTGTTTATGG GCTCCATTGT CCAGCTCAGC CAGTCTGTCA     660

CTGCCTATAT GGTGTCTGCC GCAGGCCTGG GTCTGGTCGC CATTTACTTT GCTACACAGG     720

TAGTATTTGA CAAGAGCGAC TTGGCCAAAT ACTCAGCGTA GAAAACTTCC AGCACATTGG     780

GGTGGAGGGC CTGCCTCACT GGGTCCCAGC TCCCCGCTCC TGTTAGCCCC ATGGGGCTGC     840

CGGGCTGGCC GCCAGTTTCT GTTGCTGCCA AAGTAATGTG GCTCTCTGCT GCCACCCTGT     900

GCTGCTGAGG TGCGTAGCTG CACAGCTGGG GGCTGGGGCG TCCCTCTCCT CTCTCCCCAG     960

TCTCTAGGGC TGCCTGACTG GAGGCCTTCC AAGGGGGTTT CAGTCTGGAC TTATACAGG    1020

AGGCCAGAAG GGCTCCATGC ACTGGAATGC GGGACTCTGC AGGTGGATTA CCCAGGCTC    1080

GGGTTAACAG CTAGCCTCCT AGTTGAGACA CACCTAGAGA AGGGTTTTTG GGAGCTGAA    1140

AAACTCAGTC ACCTGGTTTC CCATCTCTAA GCCCCTTAAC CTGCAGCTTC GTTTAATGT    1200

GCTCTTGCAT GGGAGTTTCT AGGATGAAAC ACTCCTCCAT GGGATTTGAA CATATGAAA    1260

TTATTTGTAG GGGAAGAGTC CTGAGGGGCA ACACACAAGA ACCAGGTCCC CTCAGCCCA    1320

AGCACTGTCT TTTTGCTGAT CCACCCCCCT CTTACCTTTT ATCAGGATGT GGCCTGTTG    1380

TCCTTCTGTT GCCATCACAG AGACACAGGC ATTTAAAATAT TTAACTTATT TATTTAACA    1440

AGTAGAAGGG AATCCATTGC TAGCTTTTCT GTGTTGGTGT CTAATATTTG GGTAGGGTG    1500

GGGATCCCCA ACAATCAGGT CCCCTGAGAT AGCTGGTCAT GGGCTGATC ATTGCCAGA    1560

TCTTCTTCTC CTGGGGTCTG GCCCCCCAAA ATGCCTAACC CAGGACCTTG GAAATTCTA    1620

TCATCCCAAA TGATAATTCC AAATGCTGTT ACCCAAGGTT AGGGTGTTGA AGGAAGGTA    1680

AGGGTGGGGC TTCAGGTCTC AACGGCTTCC CTAACCACCC CTCTTCTCTT GGCCCAGCC    1740

GGTTCCCCCC ACTTCCACTC CCCTCTACTC TCTCTAGGAC TGGGCTGATG AAGGCACTG    1800
```

| CCAAAATTTC | CCCTACCCCC | AACTTTCCCC | TACCCCCAAC | TTTCCCCACC | AGCTCCACA | 1860 |
| CCCTGTTTGG | AGCTACTGCA | GGACCAGAAG | CACAAAGTGC | GGTTTCCCAA | GCCTTTGTC | 1920 |
| ATCTCAGCCC | CCAGAGTATA | TCTGTGCTTG | GGGAATCTCA | CACAGAAACT | CAGGAGCAC | 1980 |
| CCCTGCCTGA | GCTAAGGGAG | GTCTTATCTC | TCAGGGGGGG | TTTAAGTGCC | GTTTGCAAT | 2040 |
| ATGTCGTCTT | ATTTTTTTAG | CGGGGTGAAT | ATTTTATACT | GTAAGTGAGC | AATCAGAGT | 2100 |
| TAATGTTTAT | GGTGACAAAA | TTAAAGGCTT | TCTTATATGT | TTA | | 2143 |

(2) INFORMATION FOR SEQ ID NO:16:

(i) SEQUENCE CHARACTERISTICS:
        (A) LENGTH: 2152 base pairs
        (B) TYPE: nucleic acid
        (C) STRANDEDNESS: single
        (D) TOPOLOGY: linear (xi) SEQUENCE DESCRIPTION: SEQ ID NO:16:

| GGGGCTGTAC | CAGGGCGTGC | CCAGAGCTGA | GCCGGGCACC | GAGGCCCGGA | GACACTATGA | 60 |
| TGAAGGCGTT | CGGATGGGCA | GCCTGGGGCT | GTTCCTGCAG | TGCGCCATCT | CCCTGGTCTT | 120 |
| CTCTCTGGTC | ATGGACCGGC | TGGTGCAGCG | ATTCGGCACT | CGAGCAGTCT | ATTTGGCCAG | 180 |
| TGTGGCAGCT | TTCCCTGTGG | CTGCCGGTGC | CACATGCCTG | TCCCACAGTG | TGGCCGTGGT | 240 |
| GACAGCTTCA | GCCGCCCTCA | CCGGGTTCAC | CTTCTCAGCC | CTGCAGATCC | TGCCCTACAC | 300 |
| ACTGGCCTCC | CTCTACCACC | GGGAGAAGCA | GGTGTTCCTG | CCCAAATACC | GAGGGGACAC | 360 |
| TGGAGGTGCT | AGCAGTGAGG | ACAGCCTGAT | GACCAGCTTC | CTGCCAGGCC | CTAAGCCTGG | 420 |
| AGCTCCCTTC | CCTAATGGAC | ACGTGGGTGC | TGGAGGCAGT | GGCCTGCTCC | CACCTCCACC | 480 |
| CGCGCTCTGC | GGGGCCTCTG | CCTGTGATGT | CTCCGTACGT | GTGGTGGTGG | GTGAGCCCAC | 540 |
| CGAGGCCAGG | GTGGTTCCGG | GCCGGGGCAT | CTGCCTGGAC | CTCGCCATCC | TGGATAGTGC | 600 |
| CTTCCTGCTG | TCCCAGGTGG | CCCCATCCCT | GTTTATGGGC | TCCATTGTCC | AGCTCAGCCA | 660 |
| GTCTGTCACT | GCCTATATGG | TGTCTGCCGC | AGGCCTGGGT | CTGGTCGCCA | TTTACTTTGC | 720 |
| TACACAGGTA | GTATTTGACA | AGAGCGACTT | GGCCAAATAC | TCAGCGTAGA | AAACTTCCAG | 780 |
| CACATTGGGG | TGGAGGGCCT | GCCTCACTGG | GTCCCAGCTC | CCCGCTCCTG | TTAGCCCCAT | 840 |
| GGGGCTGCCG | GGCTGGCCGC | CAGTTTCTGT | TGCTGCCAAA | GTAATGTGGC | TCTCTGCTGC | 900 |
| CACCCTGTGC | TGCTGAGGTG | CGTAGCTGCA | CAGCTGGGGG | CTGGGGCGTC | CCTCTCCTCT | 960 |
| CTCCCCAGTC | TCTAGGGCTG | CCTGACTGGA | GGCCTTCCAA | GGGGGTTTCA | GTCTGGACT | 1020 |
| ATACAGGGAG | GCCAGAAGGG | CTCCATGCAC | TGGAATGCGG | GGACTCTGCA | GGTGGATTA | 1080 |
| CCAGGCTCAG | GGTTAACAGC | TAGCCTCCTA | GTTGAGACAC | ACCTAGAGAA | GGGTTTTTG | 1140 |
| GAGCTGAATA | AACTCAGTCA | CCTGGTTTCC | CATCTCTAAG | CCCCTTAACC | TGCAGCTTC | 1200 |
| TTTAATGTAG | CTCTTGCATG | GGAGTTTCTA | GGATGAAACA | CTCCTCCATG | GGATTTGAA | 1260 |
| ATATGAAAGT | TATTTGTAGG | GGAAGAGTCC | TGAGGGGCAA | CACACAAGAA | CCAGGTCCC | 1320 |
| TCAGCCCACA | GCACTGTCTT | TTTGCTGATC | CACCCCCCTC | TTACCTTTTA | TCAGGATGT | 1380 |
| GCCTGTTGGT | CCTTCTGTTG | CCATCACAGA | GACACAGGCA | TTTAAATATT | TAACTTATT | 1440 |
| ATTTAACAAA | GTAGAAGGGA | ATCCATTGCT | AGCTTTTCTG | TGTTGGTGTC | TAATATTTG | 1500 |
| GTAGGGTGGG | GGATCCCCAA | CAATCAGGTC | CCCTGAGATA | GCTGGTCATT | GGGCTGATC | 1560 |
| TTGCCAGAAT | CTTCTTCTCC | TGGGGTCTGG | CCCCCCAAAA | TGCCTAACCC | AGGACCTTG | 1620 |
| AAATTCTACT | CATCCCAAAT | GATAATTCCA | AATGCTGTTA | CCCAAGGTTA | GGGTGTTGA | 1680 |

```
GGAAGGTAGA GGGTGGGGCT TCAGGTCTCA ACGGCTTCCC TAACCACCCC TCTTCTCTT      1740

GCCCAGCCTG GTTCCCCCCA CTTCCACTCC CCTCTACTCT CTCTAGGACT GGGCTGATG      1800

AGGCACTGCC CAAAATTTCC CCTACCCCCA ACTTTCCCCT ACCCCCAACT TTCCCCACC      1860

GCTCCACAAC CCTGTTTGGA GCTACTGCAG GACCAGAAGC ACAAAGTGCG GTTTCCCAA      1920

CCTTTGTCCA TCTCAGCCCC CAGAGTATAT CTGTGCTTGG GGAATCTCAC ACAGAAACT      1980

AGGAGCACCC CCTGCCTGAG CTAAGGGAGG TCTTATCTCT CAGGGGGGGT TTAAGTGCC      2040

TTTGCAATAA TGTCGTCTTA TTTATTTAGC GGGGTGAATA TTTTATACTG TAAGTGAGC      2100

ATCAGAGTAT AATGTTTATG GTGACAAAAT TAAAGGCTTT CTTATATGTT TA            2152

(2) INFORMATION FOR SEQ ID NO:17:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:17:

AGCTCGGAAT TCCGAGCTTG GATCCTCTAG AGCGGCCGCC GACTAGTGAG CTCGTCGACC      60

CGGGAATT                                                              68

(2) INFORMATION FOR SEQ ID NO:18:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:18:

AATTAATTCC CGGGTCGACG AGCTCACTAG TCGGCGGCCG CTCTAGAGGA TCCAAGCTCG      60

GAATTCCG                                                              68

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:19:

AGCGGATAAC AATTTCACAC AGGA                                            24

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

TGTAAAACGA CGGCCAGT                                                   18

(2) INFORMATION FOR SEQ ID NO:21:

(i) SEQUENCE CHARACTERISTICS:
        (A) LENGTH: 18 base pairs
        (B) TYPE: nucleic acid
```

(C) STRANDEDNESS: single
            (D) TOPOLOGY: linear (xi) SEQUENCE DESCRIPTION: SEQ ID NO:21:

TGTTCCTGCC CAAATACC                                                    18

(2) INFORMATION FOR SEQ ID NO:22:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:22:

GGTCTGGTCG CCATTTAC                                                    18

(2) INFORMATION FOR SEQ ID NO:23:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:23:

GGGGCAACAC ACAAGAAC                                                    18

(2) INFORMATION FOR SEQ ID NO:24:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:24:

TCAGCCCCCA GAGTATATC                                                   19

(2) INFORMATION FOR SEQ ID NO:25:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:25:

GCTCCATGCA CTGGAATG                                                    18

(2) INFORMATION FOR SEQ ID NO:26:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:26:

ACCCAGGACC TTGGAAAT                                                    18

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single (D) TOPOLOGY: linear (xi) SEQUENCE DESCRIPTION: SEQ ID NO:27:

ACACCCTAAC CTTGGGTAAC                                               20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

CCTAGAAACT CCCATGCAAG                                               20

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:29:

TGGCAGCAAC AGAAACTG                                                 18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:30:

ACTATCCAGG ATGGCGAG                                                 18

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:31:

TGATTGCTCA CTTACAGT                                                 18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:32:

TGGTTAGGGA AGCCGTTG                                                 18

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:33:

AGCCCAATGA CCAGCTAT                                                    18

(2) INFORMATION FOR SEQ ID NO:34:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:34:

TTCCAAATGC TGTTACCCAA GG                                               22

(2) INFORMATION FOR SEQ ID NO:35:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:35:

GGTGCTCCTG AGTTTCTGTG TGAG                                             24

(2) INFORMATION FOR SEQ ID NO:36:

(i) SEQUENCE CHARACTERISTICS:
       (A) LENGTH: 255 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:36:

```
Gly Leu Tyr Gln Gly Val Pro Arg Ala Glu Pro Gly Thr Glu Ala Arg
 1               5                  10                  15

Arg His Tyr Asp Glu Gly Val Arg Met Gly Ser Leu Gly Leu Phe Leu
            20                  25                  30

Gln Cys Ala Ile Ser Leu Val Phe Ser Leu Val Met Asp Arg Leu Val
        35                  40                  45

Gln Arg Phe Gly Thr Arg Ala Val Tyr Leu Ala Ser Val Ala Ala Phe
    50                  55                  60

Pro Val Ala Ala Gly Ala Thr Cys Leu Ser His Ser Val Ala Val Val
65                  70                  75                  80

Thr Ala Ser Ala Ala Leu Thr Gly Phe Thr Phe Ser Ala Leu Gln Ile
                85                  90                  95

Leu Pro Tyr Thr Leu Ala Ser Leu Tyr His Arg Glu Lys Gln Val Phe
            100                 105                 110

Leu Pro Lys Tyr Arg Gly Asp Thr Gly Gly Ala Ser Ser Glu Asp Ser
        115                 120                 125

Leu Met Thr Ser Phe Leu Pro Gly Pro Lys Pro Gly Ala Pro Phe Pro
    130                 135                 140

Asn Gly His Val Gly Ala Gly Gly Ser Gly Leu Leu Pro Pro Pro Pro
145                 150                 155                 160

Ala Leu Cys Gly Ala Ser Ala Cys Asp Val Ser Val Arg Val Val Val
                165                 170                 175

Gly Glu Pro Thr Glu Ala Arg Val Val Pro Gly Arg Gly Ile Cys Leu
            180                 185                 190
```

```
Asp Leu Ala Ile Leu Asp Ser Ala Phe Leu Leu Ser Gln Val Ala Pro
        195                 200                 205

Ser Leu Phe Met Gly Ser Ile Val Gln Leu Ser Gln Ser Val Thr Ala
        210                 215                 220

Tyr Met Val Ser Ala Ala Gly Leu Gly Leu Val Ala Ile Tyr Phe Ala
225                 230                 235                 240

Thr Gln Val Val Phe Asp Lys Ser Asp Leu Ala Lys Tyr Ser Ala
                245                 250                 255
```

(2) INFORMATION FOR SEQ ID NO:37:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:37:

```
Tyr His Arg Glu Lys Gln Val Phe Leu Pro Lys Tyr Arg Gly Asp Thr
1               5                   10                  15

Gly Gly Ala Ser Ser Glu Asp Ser Leu Met Thr Ser Phe Leu Pro Gly
                20                  25                  30

Pro Lys Pro Gly Ala Pro Phe Pro Asn Gly His Val
            35                  40
```

(2) INFORMATION FOR SEQ ID NO:38:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:38:

```
Arg Val Val Val Gly Glu Pro Thr Glu Ala Arg Val Val Pro Gly Arg
1               5                   10                  15

Gly Ile Cys Leu Asp Leu Ala Ile Leu Asp Ser
                20                  25
```

(2) INFORMATION FOR SEQ ID NO:39:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:39:

```
Gly Leu Tyr Gln Gly Val Pro Arg Ala Glu Pro Gly Thr Glu Ala Arg
1               5                   10                  15

Arg His Tyr Asp Glu Gly Val Arg Met Gly Ser
                20                  25
```

(2) INFORMATION FOR SEQ ID NO:40:

(i) SEQUENCE CHARACTERISTICS:
        (A) LENGTH: 8 amino acids
        (B) TYPE: amino acid -continued

```
        (C) STRANDEDNESS: single
        (D) TOPOLOGY: linear (ii) MOLECULE TYPE: None (xi) SEQUENCE DESCRIPTION: SEQ ID NO:40:

Asp Tyr Lys Asp Asp Asp Lys
1               5

(2) INFORMATION FOR SEQ ID NO:41:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:41:

Glu Gln Lys Leu Ile Ser Glu Glu Asp Leu Asn Met His Thr Glu His
1               5                   10                  15

His His His His His
            20
```